US012570759B2

(12) United States Patent
Sall et al.

(10) Patent No.: US 12,570,759 B2
(45) Date of Patent: *Mar. 10, 2026

(54) POLYPEPTIDES

(71) Applicant: ALLIGATOR BIOSCIENCE AB, Lund (SE)

(72) Inventors: Anna Sall, Lund (SE); Laura Von Schantz, Lund (SE); Anneli Nilsson, Lund (SE); Barnabas Nyesiga, Lund (SE); Jessica Petersson, Lund (SE); Mattias Levin, Lund (SE)

(73) Assignee: ALLIGATOR BIOSCIENCE AB, Lund (SE)

( * ) Notice: Subject to any disclaimer, the term of this patent is extended or adjusted under 35 U.S.C. 154(b) by 985 days.

This patent is subject to a terminal disclaimer.

(21) Appl. No.: 17/312,522

(22) PCT Filed: Dec. 17, 2019

(86) PCT No.: PCT/EP2019/085762
§ 371 (c)(1),
(2) Date: Jun. 10, 2021

(87) PCT Pub. No.: WO2020/127354
PCT Pub. Date: Jun. 25, 2020

(65) Prior Publication Data
US 2022/0056148 A1 Feb. 24, 2022

(30) Foreign Application Priority Data
Dec. 17, 2018 (GB) ...................................... 1820556

(51) Int. Cl.
*C07K 16/30* (2006.01)
*A61K 39/00* (2006.01)
*A61P 35/00* (2006.01)
*C07K 16/28* (2006.01)

(52) U.S. Cl.
CPC .............. *C07K 16/30* (2013.01); *A61P 35/00* (2018.01); *C07K 16/2878* (2013.01); *A61K 2039/505* (2013.01); *C07K 2317/21* (2013.01); *C07K 2317/31* (2013.01); *C07K 2317/35* (2013.01); *C07K 2317/41* (2013.01); *C07K 2317/55* (2013.01); *C07K 2317/77* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 2015/0086552 A1 | 3/2015 | Stevens et al. | |
| 2015/0368352 A1 | 12/2015 | Liu | |
| 2018/0194862 A1 | 7/2018 | Akamatsu et al. | |
| 2019/0367628 A1* | 12/2019 | Abujoub ............ | C07K 16/2866 |
| 2022/0064325 A1* | 3/2022 | Sall .................... | C07K 16/2851 |

FOREIGN PATENT DOCUMENTS

| | | | | |
|---|---|---|---|---|
| EP | 2443154 B1 | 12/2013 | | |
| WO | WO-2014081955 A1 * | 5/2014 | ........... | A61K 39/395 |
| WO | 2015/181805 A9 | 12/2015 | | |
| WO | 2016/044224 A1 | 3/2016 | | |
| WO | WO-2016172485 A2 * | 10/2016 | .............. | A61P 37/02 |
| WO | WO-2017049004 A1 * | 3/2017 | ............ | C07K 16/00 |
| WO | 2017/182672 A1 | 10/2017 | | |
| WO | WO-2018158719 A1 * | 9/2018 | ........... | C07K 16/244 |
| WO | 2018/176159 A1 | 10/2018 | | |
| WO | 2018/220216 A1 | 12/2018 | | |
| WO | 2019/093342 A1 | 5/2019 | | |

OTHER PUBLICATIONS

Liu et al. J Biol Chem. 2015. 290(12): 75357562 (Year: 2015).*
Zeboudj et al. J American College Cardiol. 2018. 71(2): 160-172. (Year: 2018).*
Lewis. Nature Biotech. 2014. 32(2):191-198 (Year: 2014).*
Altschul, S.F., "A Protein Alignment Scoring System Sensitive at All Evolutionary Distances" J. Mol. Evol. (1993) 36:290-300.
Karlin, et al., "Applications and statistics for multiple high-scoring segments in molecular sequences" Proc. Natl. Acad. Sci. (1993) 90:5873-5877.
Altschul, et al., "Basic Local Alignment Search Tool" J. Mol. Biol. (1090) 215:403-410.
Abbvie, "Remarkable Impact on Patients' Lives" (2016) Chicago, IL, available at investors.abbvie.com/static-files/4c774749-25a8-4c8d-939d-3a3cdc45c8d6.
Bonisch, et al., "Novel CH1:CL interfaces that enhance correct light chain pairing in heterodimeric bispecific antibodies" Protein Engineering, Design & Selection (2017) 30(9):685-696.
Brinkmann, et al., "The making of bispecific antibodies" MABS (2017) 9(2):182-212.
Caceci, et al., "Fitting Curves to Data" Byte (1984) 9:340-362.
Cooke, et al., "EFab domain substitution as a solution to the light-chain pairing problem of bispecific antibodies" MABS (2018) 10(8):1248-1259.
Devereux, et al., "A comprehensive set of sequence analysis programs for the VAX" Nuc. Acids Res. (1984) 12:387-395.
Eyvazi, et al., "Antibody Based EpCAM Targeted Therapy of Cancer, Review and Update" Curr. Cancer Drug Targets (2018) 18:857-868.
Golay, et al., "Design and Validation of a Novel Generic Platform for the Production of Tetravalent IgG1-like Bispecific Antibodies" Journal of Immunology (2016) 196:3199-3211.

(Continued)

*Primary Examiner* — Anne M. Gussow
*Assistant Examiner* — Brianna K Swartwout
(74) *Attorney, Agent, or Firm* — Robert C. Netter, Jr.; Dann, Dorfman, Herrell & Skillman

(57) ABSTRACT

The present invention provides bispecific antibodies of an antibody format, and which comprise one or more Fab fragments and an immunoglobulin molecule. The invention further provides compositions of said bispecific antibodies, as well as methods and uses of the same. The invention further provides a method of generating bispecific antibodies of the format.

14 Claims, 18 Drawing Sheets

Figure 1:
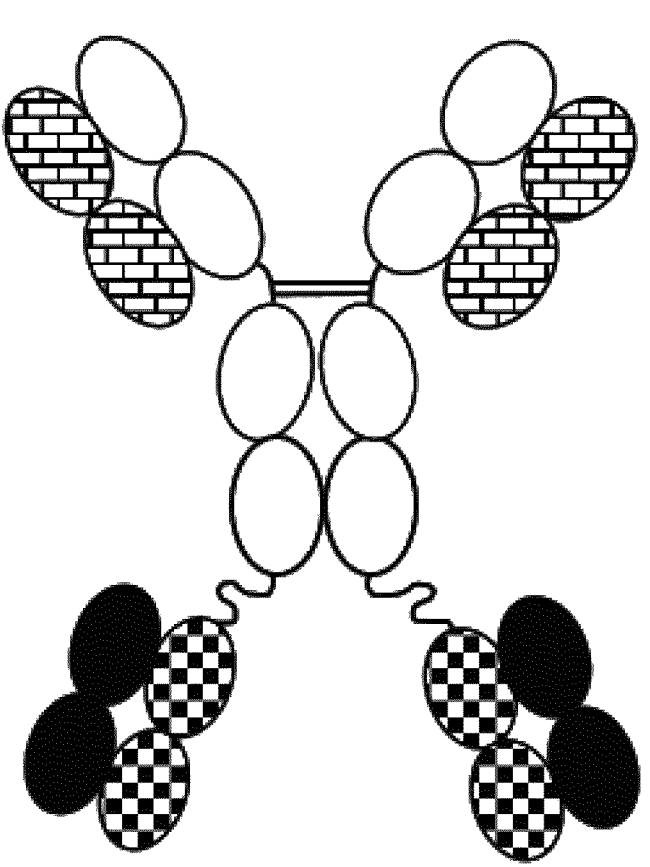

Specification includes a Sequence Listing.

(56)          References Cited

OTHER PUBLICATIONS

Henikoff, et al., "Amino acid substitution matrices from protein blocks" Proc. Natl. Acad. Sci. (1992) 89:10915-10919.

Husain, et al., "Expanding the Boundaries of Biotherapeutics with Bispecific Antibodies" BioDrugs (2018) 32:441-464.

Krah, et al., "Engineering IgG-Like Bispecific Antibodies—An Overview" Antibodies (2018) 7:28.

Liu, et al., "A Novel Antibody Engineering Strategy for Making Monovalent Bispecific Heterodimeric IgG Antibodies by Electrostatic Steering Mechanism" J. Biol. Chem. (2015) 290(12):7535-7562.

Mazor, et al., "Improving target cell specificity using a novel monovalent bispecific IgG design" MABS (2015) 7:377-389.

Stern, et al., "5T4 oncofoetal antigen: an attractive target for immune intervention in cancer" Cancer Immunol. Immunother. (2017) 66:415-426.

Thompson, et al., "CLUSTAL W: improving the sensitivity of progressive multiple sequence alignment through sequence weighting, position-specific gap penalties and weight matrix choice" Nucleic Acids Research (1994) 22(22):4673-4680.

Wong, et al., "A double-filter method for nitrocellulose-filter binding: Application to protein-nucleic acid interactions" Proc. Natl. Acad. Sci. (1993) 90:5428-5432.

Dahlen, et al., "Bispecific antibodies in cancer immunotherapy" Ther. Adv. Vaccines Immunother. (2018) 6(1):3-17.

Lewis, et al., "Generation of bispecific IgG antibodies by structure-based design of an orthogonal Fab interface".

Lefranc, et al., "IMGT unique numbering for immunoglobulin and T cell receptor constant domains and Ig superfamily C-like domains" Developmental and Comparative Immunology (2005) 29:185-203.

Lefranc, et al., "IMGT unique numbering for immunoglobulin and T cell receptor variable domains and Ig superfamily V-like domains" Developmental and Comparative Immunology (2003) 27:55-77.

* cited by examiner

A

- Combo 1 v6 day 7-BSA
- Combo 1 v6 day 7-Human serum
- Combo 1 v9' day 7-BSA
- Combo 1 v9' day 7-Human serum

B

- Combo 2 v9 day7-BSA
- Combo 2 v9 day7-Human serum
- Combo 2 v10 day7-BSA
- Combo 2 v10 day7-Human serum

- ●— Combo 2 Morrison CHO-Ag2
- ■— Combo 2 v9 CHO-Ag2
- -⊙· Combo 2 Morrison CHO-ctrl
- -◱· Combo 2 v9 CHO-ctrl

- ●— Combo 2 v10 CHO-Ag2
- ■— Combo 2 v19 CHO-Ag2
- -⊙· Combo 2 v10 CHO-ctrl
- -◱· Combo 2 v19 CHO-ctrl

POLYPEPTIDES

This application is a § 371 application of PCT/EP2019/085762, filed Dec. 17, 2019, which in turn claims priority to GB Application 1820556.7, filed Dec. 17, 2018. The entire disclosure of each of the foregoing applications is incorporated by reference herein.

Incorporated herein by reference in its entirety is the Sequence Listing being concurrently submitted via EFS-Web as a text file named SeqList.txt, created Jun. 10, 2021, and having a size of 36,210 bytes.

FIELD OF INVENTION

The present invention relates to bispecific antibodies of a new structural format, with specificity for two target antigens, and comprising an immunoglobulin and a Fab. In the bispecific antibody, the Fab is appended to the C-terminal end of the heavy chain of the immunoglobulin via the light chain of the Fab. The invention also provides a polypeptide, comprising an antigen binding fragment an antigen binding fragment with particular mutations that promote association of the heavy chain with the light chain.

BACKGROUND

Cancer is a leading cause of premature deaths in the developed world. Immunotherapy of cancer aims to mount an effective immune response against tumour cells. This may be achieved by, for example, breaking tolerance against tumour antigen, augmenting anti-tumour immune responses, and stimulating local cytokine responses at the tumour site. The key effector cell of a long lasting anti-tumour immune response is the activated tumour-specific effector T cell. Potent expansion of activated effector T cells can redirect the immune response towards the tumour. In this context, regulatory T cells (Treg) play a role in inhibiting the anti-tumour immunity. Depleting, inhibiting, reverting or inactivating Tregs may therefore provide anti-tumour effects and revert the immune suppression in the tumour microenvironment. Further, incomplete activation of effector T cells by, for example, dendritic cells can cause T cell anergy, which results in an inefficient anti-tumour response, whereas adequate induction by dendritic cells can generate a potent expansion of activated effector T cells, redirecting the immune response towards the tumour. In addition, natural killer (NK) cells play an important role in tumour immunology by attacking tumour cells with down-regulated human leukocyte antigen (HLA) expression and by inducing antibody-dependent cellular cytotoxicity (ADCC). Stimulation of NK cells may thus also reduce tumour growth.

Bispecific antibodies have utility in cancer treatment as they allow for dual targeting of cells. For example, bispecific antibodies may be capable of activating the host immune cells in the vicinity of tumour cells and are thus an alternative to existing monospecific drugs that target only one antigen.

Bispecific antibodies are more difficult to generate compared to monoclonal antibodies. Many different formats have been invented and all formats have different strengths and limitations. A format suitable for any application does not exist.

The number of formats engineered is vast and the formats can be grouped according to their general architecture. Brinkmann and Kontermann have proposed a classification of 19 groups (see Brinkmann & Kontermann, 2017, mAbs. 9:182-212). The major differences between the groups are in regard to their symmetry, their target valency, their components and the position of these.

Different properties are generally acknowledged for different bispecific format groups. Fragment-based formats that lack an Fc part have limited half-life and cannot mediate Fc effector functions. IgG-like formats display only monovalent binding to each target.

One major bioprocessing challenge when manufacturing bispecific antibodies carrying more than one heavy chain and one light chain is wrongly pairing of the chains (see Krah et al, 2018, Antibodies, 7). For IgG like bispecific antibodies this is often referred to as the light chain mispairing. Several mutational strategies have been reported to promote correct heavy chain and light chain pairing (see Lewis et al, 2014, Nat Biotechnol, 32:191-8; Liu et al, 2015, J Biol Chem, 290:7535-62; Mazor et al, 2015, mAbs, 7:377-89; Golay et al, 2016, J Immunol, 196:3199-211; Bönisch et al, 2017, Protein Eng Des Sel, 30:658-96).

In addition, other properties are generally acknowledged for different bispecific format groups. Fragment-based formats that lack an Fc part have limited half-life and cannot mediate Fc effector functions. Formats with single chain fragments (scFv) may suffer from poor stability. IgG-like formats display only monovalent binding to each target.

There is a need for a plug-and-play format that is tetravalent, carries an Fc domain, and does not give rise to light chain mispaired constructs.

BRIEF SUMMARY OF INVENTION

The following invention provides a new bispecific antibody format. The invention is of a format consisting of an immunoglobulin coupled to one or more Fab fragments, optionally connected via a polypeptide linker. The immunoglobulin and Fab fragment are connected via the C-terminal end of the immunoglobulin and the N-terminal end of the light chain of the Fab fragments (see, for example, FIG. 1). The constructs will thus consist of three separate chains, 1) a long chain that consists of the immunoglobulin heavy chain and the light chain of the additional Fab fragment, 2) a light chain that binds to the VH and CH1 domains of the immunoglobulin part, and 3) a short heavy chain that binds to the light chain appended to the immunoglobulin.

The invention also provides a polypeptide comprising an antigen binding fragment, wherein the antigen binding fragment comprises an antibody VL region and an antibody VH region, wherein the antigen binding fragment comprises four or more mutations to promote association of the heavy chain with the light chain, wherein the VL region comprises a mutation at position 44 (according to IMGT numbering), and wherein the VH region comprises a mutation at position 44 (according to IMGT numbering. The inventors have surprisingly identified that such an antibody is particularly stable, and can form with minimal mispairing.

Mutations between the VH-CH1 and VL-CKappa (or VL-CLambda) are introduced into the bispecific antibodies of the invention. These mutations create surfaces that limit formation of aggregates and by-product Fab fragments. The mutations can for example cause steric hindrance or charge incompatibility of wrong chains or promote interactions between correct chains for example by creating salt or disulphide bridges. As part of the invention, the inventors have found some particular combination of mutations that promote stability, binding and manufacturability, and which combination of mutations that would be most beneficial could not be predicted.

One of the most important advantages of the new invention is the format's plug-and-play capacity, which is uncommon for bispecific formats. This is partly due to the use of Fab fragments, instead of scFv, which gives stability and reduces the risk of having to perform lengthy lead optimization campaigns. Furthermore, the tetravalent architecture of bispecific antibodies of one embodiment of the claims provides avidity effects and reduces the risk of having to affinity maturate the antibodies. In addition, the invention presents a format that carries all domains of the Fc portion found in natural antibodies allowing for the use of standard CMC purification methodologies (such as the use of protein A) and longer half-life in vivo. An Fc portion will also allow biological functions which may be modulated by the presence of a variant Fc region including antibody-dependent cell cytotoxicity (ADCC), antibody-dependent cellular phagocytosis (ADCP), complement-dependent cytotoxicity (CDC), and/or apoptosis.

In the presented invention, the Fab fragments are attached to the immunoglobulin in a way that allows several benefits over other formats. For example, since the Fabs are appended to the Fc portion (the so-called C-terminal end), instead of on top of the immunoglobulin binding domains, no steric hindrance causing reduced affinities is observed. Furthermore, since the Fab fragments are appended via their light chains, no mispairing of light chains can occur. This is a very valuable feature as light chain mispairing can cause a severe change in the drug potency and is problematic to analyze, and wrongly paired by-products are difficult to get rid of during CMC manufacturing.

DETAILED DESCRIPTION OF INVENTION

A first aspect of the invention provides a bispecific antibody comprising:
  (a) an immunoglobulin molecule having specificity for a first antigen, the immunoglobulin molecule comprising a first heavy chain polypeptide and a first light chain polypeptide; and
  (b) at least one Fab fragment having specificity for a second antigen, the Fab fragment comprising a second heavy chain polypeptide and a second light chain polypeptide
  wherein the second light chain polypeptide is fused to the C-terminus of the first heavy chain polypeptide
  and wherein the bispecific antibody comprises one or more mutations to promote association of the first heavy chain polypeptide with the first light chain polypeptide and/or to promote association of the second heavy chain polypeptide with the second light chain polypeptide.

As used herein, the terms "antibody" or "antibodies" refer to molecules that contain an antigen binding site, e.g. immunoglobulin molecules and immunologically active fragments of immunoglobulin molecules that contain an antigen binding site. Immunoglobulin molecules can be of any type (e.g. IgG, IgE, IgM, IgD, IgA and IgY), class (e.g. IgG1, IgG2, IgG3, IgG4, IgA1 and IgA2) or a subclass of immunoglobulin molecule. Antibodies include, but are not limited to, synthetic antibodies, monoclonal antibodies, single domain antibodies, single chain antibodies, recombinantly produced antibodies, multi-specific antibodies (including bispecific antibodies), human antibodies, humanized antibodies, chimeric antibodies, intrabodies, scFvs (e.g.

including mono-specific and bi-specific, etc.), Fab fragments, F(ab') fragments, disulfide-linked Fvs (sdFv), anti-idiotypic (anti-Id) antibodies, and epitope-binding fragments of any of the above.

As already specified, the antibody of the invention is a bispecific antibody.

It will therefore be appreciated by persons skilled in the art that the term "immunoglobulin" includes immunoglobulin molecules and immunologically active fragments of immunoglobulin molecules that contain an antigen binding site, as described above.

As used herein, the term "antibody fragment" is a portion of an antibody such as $F(ab')_2$, $F(ab)_2$, Fab', Fab, Fv, scFv and the like. Regardless of structure, an antibody fragment binds with the same antigen that is recognized by the intact antibody. For example, an anti-OX40 antibody fragment binds to OX40. The term "antibody fragment" also includes isolated fragments consisting of the variable regions, such as the "Fv" fragments consisting of the variable regions of the heavy and light chains and recombinant single chain polypeptide molecules in which light and heavy variable regions are connected by a peptide linker ("scFv proteins"). As used herein, the term "antibody fragment" does not include portions of antibodies without antigen binding activity, such as Fc fragments or single amino acid residues.

By "Fab fragment", we include Fab fragments (comprising a complete light chain and the variable region and CH1 region of a heavy chain) which are capable of binding the same antigen that is recognized by the intact antibody. Fab fragment is a term known in the art, and Fab fragments comprise one constant and one variable domain of each of the heavy and the light chain.

The term "bispecific" as used herein means the polypeptide is capable of specifically binding two distinct target entities. Bispecific polypeptides, e.g. antibodies, targeting two targets, have the potential to induce specific activation of the immune system in locations where both targets are over expressed.

The term "polypeptide" is used herein in its broadest sense to refer to a compound of two or more subunit amino acids, amino acid analogues, or other peptidomimetics. The term "polypeptide" thus includes short peptide sequences and also longer polypeptides and proteins. As used herein, the term "amino acid" refers to either natural and/or unnatural or synthetic amino acids, including both D or L optical isomers, and amino acid analogues and peptidomimetics. In a particular embodiment, the polypeptide can comprise one or more peptide sequences (for example, one or more antibody chain).

Thus, a first heavy chain polypeptide is a polypeptide comprising or consisting of the heavy chain of a first antibody or antigen-binding fragment, and a first light chain polypeptide is a polypeptide comprising or consisting of the light chain of a first antibody or antigen-binding fragment.

Accordingly, a second heavy chain polypeptide is a polypeptide comprising or consisting of the heavy chain of a second antibody or antigen-binding fragment, and a second light chain polypeptide is a polypeptide comprising or consisting of the light chain of a second antibody or antigen-binding fragment.

The first and second antibodies or antigen-binding fragments have specificity for a first antigen and a second antigen, respectively.

The term antibody "having specificity for" refers to an antibody that is constructed to direct its binding specificity(ies) at a certain target/marker/epitope/antigen, i.e. an antibody that immunospecifically binds to a target/marker/ epitope/antigen. Also, the expressions antibodies "selective for", "directed to", "binding", "against" or "directed against" a certain target/marker/epitope/antigen may be used, having the same definition as "having specificity for". A bispecific antibody having specificity for two different targets/markers/epitopes/antigens binds immunospecifically to both targets/markers/epitopes/antigens. If an antibody is directed to a certain target antigen, such as CD40, it is thus assumed that said antibody could be directed to any suitable epitope present on said target antigen structure.

In one embodiment of the bispecific antibody of the invention, the immunoglobulin molecule comprises two copies of the first heavy chain polypeptide and/or two copies of the first light chain polypeptide.

Thus, in one embodiment the immunoglobulin molecule comprises two heavy chain polypeptides and two corresponding light chain polypeptides. By "corresponding" we mean that the heavy and light chains assemble into an antibody format, i.e. the heavy chains associate with the light chains via the CH1 and CKappa or CLambda regions, and the VH and VL regions, and the heavy chains are also linked together via the CH2 and CH3 regions.

In one embodiment the bispecific antibody comprises two Fab fragments according to (b), i.e. two Fab fragments according to having specificity for a second antigen, the Fab fragments each comprising a second heavy chain polypeptide and a second light chain polypeptide.

Thus, in one embodiment the bispecific antibody comprises (a) an immunoglobulin molecule with specificity for a first antigen, and comprising two heavy chain polypeptides and two light chain polypeptides, and (b) two Fab fragments (with specificity for a second antigen) and comprising a second heavy chain polypeptide and a second light chain polypeptide Accordingly, in one embodiment, the bispecific antibody comprises:

an immunoglobulin molecule comprising two copies of the first heavy chain polypeptide and two copies of the first light chain polypeptide, and the bispecific antibody further comprises two Fab fragments according to having specificity for a second antigen, the Fab fragments each comprising a second heavy chain polypeptide and a second light chain polypeptide, and the first Fab fragment is fused to the C-terminus of the first copy of the first heavy chain polypeptide via the light chain polypeptide of the Fab fragment, and the second Fab fragment is fused to the C-terminus of the second copy of the first heavy chain polypeptide via the light chain polypeptide of the Fab fragment.

In one embodiment of the bispecific antibody according to first aspect of the invention, the immunoglobulin molecule comprises a human Fc region or a variant of a said region, where the region is an IgG1, IgG2, IgG3 or IgG4 region, preferably an IgG1 or IgG4 region.

The constant (Fc) regions of the antibodies may mediate the binding of the immunoglobulin to host tissues or factors, including various cells of the immune system (e.g. effector cells) and the first component (C1q) of the classical complement system. The Fc region is preferably a human Fc region, or a variant of a said region. The Fc region may be an IgG1, IgG2, IgG3 or IgG4 region, preferably an IgG1 or IgG4 region. A variant of an Fc region typically binds to Fc receptors, such as FcgammaR and/or neonatal Fc receptor (FcRn) with altered affinity providing for improved function and/or half-life of the polypeptide. The biological function and/or the half-life may be either increased or decreased relative to the half-life of a polypeptide comprising a native Fc region. Examples of such biological functions which may be modulated by the presence of a variant Fc region include antibody-dependent cell cytotoxicity (ADCC), antibody-dependent cellular phagocytosis (ADCP), complement-dependent cytotoxicity (CDC), and/or apoptosis.

It will be appreciated by persons skilled in the art that in one embodiment the Fc region is a naturally occurring (i.e. wildtype) human Fc region. In an alternative embodiment the Fc region is a non-naturally occurring (e.g. mutated) human Fc region.

In one embodiment the Fc region of the immunoglobulin may have modified glycosylation. For example, the Fc region may be afucosylated.

By "afucosylated", "defucosylated" or "non-focusylated" antibodies we mean that the Fc region of the antibody does not have any fucose sugar units attached, or has a decreased content of fucose sugar units. Decreased content may be defined by the relative amount of fucose on the modified antibody compared to the fucosylated 'wild type' antibody, e.g. fewer fucose sugar units per immunoglobulin molecule compared to the equivalent antibody expressed in the absence of an inhibitor of mannosidase and/or in the presence of GDP-6-deoxy-D-lyxo-4-hexulose reductase.

Mutations

As described above, the bispecific antibody of the invention comprises one or more mutations to promote association of the first heavy chain polypeptide with the first light chain polypeptide and/or to promote association of the second heavy chain polypeptide with the second light chain polypeptide.

In one embodiment, the bispecific antibody comprises two mutations to 20 mutations, for example: two mutations to 19 mutations, two mutations to 18 mutations, two mutations to 17 mutations, two mutations to 16 mutations, two mutations to 15 mutations, two mutations to 14 mutations, two mutations to 13 mutations, two mutations to 12 mutations, two mutations to 11 mutations, and two mutations to 10 mutations, preferably two mutations to 17 mutations.

In a particular embodiment, the bispecific antibody comprises two mutations, four mutations, seven mutations, eight mutations, 10 mutations, 11 mutations, 12 mutations, 13 mutations, 15 mutations, or 17 mutations.

In one embodiment of the invention, the one or more mutations are in one or more of the following regions of the bispecific antibody:

(i) the CH1 region of the first heavy chain polypeptide, and/or (ii) the VH region of the first heavy chain polypeptide, and/or (iii) the CH1 region of the second heavy chain polypeptide, and/or (iv) the VH region of the second heavy chain polypeptide, and/or (v) the CKappa or CLambda region of the first light chain polypeptide, and/or (vi) the VL region of the first light chain polypeptide, and/or (vii) the CKappa or CLambda region of the second light chain polypeptide, and/or (viii) the VL region of the second light chain polypeptide.

In one embodiment of the invention the one or more mutations prevent the binding of the second heavy chain polypeptide to the first light chain polypeptide, i.e. the mutations prevent the formation of a Fab by-product, Alternatively, or additionally, the one or more mutations may prevent self-aggregation of the first heavy chain polypeptide fused to the second light chain polypeptide i.e. the mutations prevent the formation of aggregates.

It will be appreciated by persons skilled in the art, that in one embodiment the mutations may prevent the formation of aggregates and/or a Fab by-product by generating steric hindrance and/or incompatibility between charges.

By "steric hindrance" we mean the slowing of a reaction due to steric bulk, i.e. the size of an amino acid molecule prevents association of two protein surfaces that may otherwise occur if a smaller amino acid is present.

By "incompatibility between charges" we mean that an unwanted product will not form as the charges are incompatible and prevent the product from forming, e.g. there may be two negatively charged portions which repel and prevent an unwanted product from forming.

As described above, said mutations limit the formation of a Fab by-product and/or aggregates by, for example, creating surfaces that limit the formation of aggregates or by-product Fab fragments. In one embodiment, the mutations prevent formation of a Fab by-product by generating steric hindrance and/or incompatibility between charges (leading to charge incompatibility of wrong chains). The mutations may also promote interactions between correct chains (i.e. between the first heavy chain polypeptide and the first light chain polypeptide, and/or between the second heavy chain polypeptide and the second light chain polypeptide) by, for example, creating salt or disulphide bridges.

Thus, the mutations may favour formation of the bispecific antibody.

In one embodiment, the percentage of aggregates formed during manufacturing is less than or equal to 25%. Optionally the percentage of aggregates is less than or equal to 20%, 17.5%, 15%. 13.5% or 10%. Preferably the percentage of aggregates is less than 10%. Optionally these measurements are carried out when the chains of the bispecific antibody are transfected at equal ratios, e.g. at a ratio of 1:1:1 when 3 chains are used during production.

Alternatively, the chain transfection ratio may be optimised. Optionally the % of aggregates when the chain transfection ratio is optimised may be less than or equal to 3.5%, 3%, 2.5% or 2%.

In one embodiment, the bispecific antibody comprises one or more mutation pairs each comprising two functionally compatible mutations.

By "functionally compatible mutations" we mean the mutations have complementary functions, e.g. one mutation of the pair (in one chain) may be a mutation that forms a positively charged region, and the other mutation (in another chain) forms a negatively charged region. Together these mutations act in a functionally compatible way promoting association of the respective chains.

In one embodiment, the bispecific antibody comprises one or more mutation pairs in one or more of the following region groups:

(a) the CH1 and CKappa or CLambda region of the immunoglobulin; and/or (b) the CH1 and CKappa or CLambda region of the Fab; and/or (c) the VL and VH regions of the immunoglobulin; and/or (d) the VL and VH regions of the Fab.

Thus, in one embodiment, the mutation pairs are in the CH1 and CKappa or CLambda regions of the Fab and/or the immunoglobulin, and the mutation pairs are selected from:

(a) cavity and protruding surface mutations (i.e. steric mutations); and/or (b) hydrophobic swap mutations; and/or (c) charged mutations (i.e. salt mutations); and/or (d) mutations resulting in the formation of a disulphide bridge.

The mutation pairs may alternatively or additionally be in the VH and VL regions of the Fab and/or the immunoglobulin, the mutation pairs in the VH and VL regions are selected from:

(a) charged mutations (i.e. salt mutations); and/or (b) double charged mutations; and/or (c) mutations resulting in the formation of a disulphide bridge.

In one embodiment of the invention, the bispecific antibody comprises certain combinations of mutations pairs. Accordingly, the bispecific antibody comprises one or more mutation pair selected from:

(a) steric mutations in the CH1 and CKappa or CLambda regions of the immunoglobulin;

(b) steric mutations in the CH1 and CKappa or CLambda regions of the immunoglobulin, salt mutations in the VH and VL regions of the immunoglobulin, and salt mutations in the VH and VL regions of the Fab;

(c) steric mutations in the CH1 and CKappa or CLambda regions of the immunoglobulin, salt mutations in the VH and VL regions of the immunoglobulin, salt mutations and disulphide bridge-forming mutations in the VH and VL regions of the Fab;

(d) hydrophobic mutations in the CH1 and CKappa or CLambda regions of the immunoglobulin and salt mutations in the CH1 and CKappa or CLambda regions of the Fab;

(e) hydrophobic mutations in the CH1 and CKappa or CLambda regions of the immunoglobulin, salt mutations in the VH and VL regions of the immunoglobulin, salt mutations in the CH1 and CKappa or CLambda regions of the Fab, and salt mutations in the VH and VL regions of the Fab;

(f) hydrophobic mutations in the CH1 and CKappa or CLambda regions of the immunoglobulin, salt mutations in the VH and VL regions of the immunoglobulin, salt mutations in the CH1 and CKappa or CLambda regions of the Fab, and salt mutations and disulphide bridge-forming mutations in the VH and VL regions of the Fab;

(g) disulphide bridge-forming mutations in the CH1 and CKappa or CLambda regions of the Fab;

(h) steric mutations in the CH1 and CKappa or CLambda regions of the immunoglobulin, salt mutations in the VH and VL regions of the immunoglobulin, salt mutations in the CH1 and CKappa or CLambda regions of the Fab, and salt mutations in the VH and VL regions of the Fab;

(i) steric mutations in the CH1 and CKappa or CLambda regions of the immunoglobulin, salt mutations in the VH and VL regions of the immunoglobulin, salt mutations in the CH1 and CKappa or CLambda regions of the Fab, and salt mutations and disulphide bridge-forming mutations in the VH and VL regions of the Fab;

(j) salt mutations in the CH1 and CKappa or CLambda regions of the immunoglobulin, salt mutations in the VH and VL regions of the immunoglobulin, steric mutations in the CH1 and CKappa or CLambda regions of the Fab, and salt mutations in the VH and VL regions of the Fab;

(k) salt mutations in the CH1 and CKappa or CLambda regions of the immunoglobulin, salt mutations in the VH and VL regions of the immunoglobulin, steric mutations in the CH1 and CKappa or CLambda regions of the Fab, and salt mutations and disulphide bridge-forming mutations in the VH and VL regions of the Fab;

(l) salt mutations in the VH and VL regions of the immunoglobulin, steric mutations in the CH1 and CKappa or CLambda regions of the Fab, and salt mutations in the VH and VL regions of the Fab;

(m) salt mutations in the VH and VL regions of the immunoglobulin, steric mutations in the CH1 and CKappa or CLambda regions of the Fab, and salt mutations and disulphide bridge-forming mutations in the VH and VL regions of the Fab;

(n) hydrophobic mutations in the CH1 and CKappa or CLambda regions of the immunoglobulin, salt mutations in the VH and VL regions of the immunoglobulin, steric mutations and salt mutations in the CH1 and CKappa or CLambda regions of the Fab, and salt mutations in the VH and VL regions of the Fab;

(o) hydrophobic mutations in the CH1 and CKappa or CLambda regions of the immunoglobulin, salt mutations in the VH and VL regions of the immunoglobulin, steric mutations and salt mutations in the CH1 and CKappa or CLambda regions of the Fab, and salt mutations and disulphide bridge forming mutations in the VH and VL regions of the Fab;

(p) steric mutations and salt mutations in the CH1 and CKappa or CLambda regions of the immunoglobulin, salt mutations in the VH and VL regions of the immunoglobulin, hydrophobic mutations in the CH1 and CKappa or CLambda regions of the Fab, and salt mutations in the VH and VL regions of the Fab; or (q) steric mutations and salt mutations in the CH1 and CKappa or CLambda regions of the immunoglobulin, salt mutations in the VH and VL regions of the immunoglobulin, hydrophobic mutations in the CH1 and CKappa or CLambda regions of the Fab, and salt mutations and disulphide bridge-forming mutations in the VH and VL regions of the Fab.

(r) steric mutations in the CH1 and CKappa or CLambda regions of the immunoglobulin, salt mutations in the VH and VL regions of the immunoglobulin, salt mutation in the CH1 and alanine mutation in the CKappa or CLambda regions of the Fab, and salt mutations in the VH and VL regions of the Fab;

In one embodiment of the invention the mutations are at positions selected from the group consisting of:

(a) one or more of the following positions in the CH1 domain: H168, F170, L145, S183 and T187 (according to EU numbering); and/or (b) a position selected from the one or more of the following position ranges in the CKappa or CLambda domain: position 132 to 138, position 173 to 179, position 130 to 136, position 111 to 117 and position 134 to 140 (according to Kabat numbering); and/or (c) a position selected from one or more of the following position ranges in the VL: position 41 to 47, position 117 to 123 and position 46 to 52 (according to IMGT numbering); and/or (d) a position selected from one or more of the following position ranges in the VH: position 41 to 47, position 46 to 52 and position 117 to 123 (according to IMGT numbering).

One mutation in each of the ranges given above will be the relevant functional mutation as it will be a position that makes contact with the amino acid in the corresponding domain/chain, and is therefore the relevant interface between chains.

It will therefore be appreciated by persons skilled in the art that mutations in the position ranges given above are suitable, as the relevant functional feature is whether the position contacts a corresponding position on the other chain, i.e. a position in the VH chain that contacts a corresponding position in a VL chain is the relevant position, or a position in a CKappa or CLambda domain that contacts a position in a CH1 chain is the relevant position.

In one embodiment of the invention, the mutations are at positions selected from the group consisting of:

(a) one or more of the following positions in the CH1 domain: H168, F170, L145, S183 and T187 (according to EU numbering); and/or (b) one or more of the following positions in the CKappa or CLambda domain: L135, S176, V133, S114 and N137 (according to Kabat numbering); and/or (c) one or more of the following positions in the VL: Q44, Q120 and A49 (according to IMGT numbering); and/or (d) one or more of the following positions in the VH: Q44, G49 and Q120 (according to IMGT numbering).

For example, the mutations may be selected from the group consisting of:

(a) one or more of the following mutations in the CH1 domain: H168A, F170G, L145Q, S183V and T187E (according to EU numbering); and/or (b) one or more of the following mutations in the CKappa or CLambda domain: L135Y, S176W, V133T, S176V, S114A and N137K (according to Kabat numbering); and/or (c) one or more of the following mutations in the VL: Q44R, Q44E, Q120C, Q44D and A49D (according to IMGT numbering); and/or (d) one or more of the following mutations in the VH: Q44E, Q44R, G49C, Q44K and Q120K (according to IMGT numbering).

For example, the mutations may be selected from the group consisting of:

(a) one or more of the following mutations in the CH1 domain: X168A, X170G, X145Q, X183V and X187E (according to EU numbering); and/or (b) one or more of the following mutations in the CKappa or CLambda domain: X135Y, X176W, X133T, X176V, X114A and X137K (according to Kabat numbering); and/or (c) one or more of the following mutations in the VL: X44R, X44E, X120C, X44D and X49D (according to IMGT numbering); and/or (d) one or more of the following mutations in the V: X44E, X44R, X49C, X44K and X120K (according to IMGT numbering);

wherein X is any amino acid.

In one embodiment, the combination of mutations is selected from any one or more of Set 1, Set 2, Set 3, Set 3', Set 4, Set 5a, Set 5b, Set 6, and/or Set 7, given in Table A below.

TABLE A (i)

Mutations introduced between CH1 and CKappa/CLambda interface and VL and VH interface.

| | Domain | Type of mutation | Position | Mutation |
|---|---|---|---|---|
| Set 1 | CH1 | Cavity | H168 F170 | H168A, F170G |
| | CKappa/CLambda | Protruding surface | L135 S176 | L135Y, S176W |
| Set 2 | CH1 | Hydrophobic swap | L145 S183 | L145Q, S183V |
| | CKappa/CLambda | Hydrophobic swap | V133 S176 | V133T, S176V |
| Set 3 | CH1 | Charged, negative | T187 | T187E |
| | CKappa/CLambda | Charged, positive | S114 N137 | S114A, N137K |
| Set 3' | CH1 | Charged, negative | T187 | T187E |
| | CKappa/CLambda | Alanine | S114 | S114A |
| Set 4 | CH1 | To form disulphide bridge | F126 | F126C |
| | CKappa/CLambda | To form disulphide bridge | S121 | S121C |
| Set 5a | VL | Charged, positive | Q44 | Q44R |
| | VH | Charged, negative | Q44 | Q44E |
| Set 5b | VL | Charged, negative | Q44 | Q44E |
| | VH | Charged, positive | Q44 | Q44R |
| Set 6 | VL | To form disulphide bridge | Q120/A120 | Q120C/A120C |
| | VH | To form disulphide bridge | G49 | G49C |
| Set 7 | VL | Charged, double negative | Q44 A49 | Q44D, A49D |
| | VH | Charged, double positive | Q44 Q120 | Q44K, Q120K |

TABLE A (ii)

Optional further mutations, which can be made to the polypeptides and bispecific antibodies herein.

| | |
|---|---|
| VH | X44R/E/D/K, X49C, X120K |
| VL | X44R/E/D/K, X49D X120C |
| CH1 | H168A/G, F170G/A, L145Q, S183V, T187E/D, |
| CKappa/CLambda | S/T114A, V133T, L135Y/W, N/S137K/R/H, S176W/V/Y |

*numbering according to IMGT system for VH/VL domains and according to EU numbering system for constant domains
*X refers to any amino acid In one embodiment of the bispecific antibody of the invention, the antibody comprises a combination of sets of mutations as outlined in Table B below, i.e. the bispecific antibody may comprise mutations according to any one of Variant 1 to Variant 20.

TABLE B

Mutational strategies to avoid pairing of the long heavy chain with itself and pairing of L1 with H2 short and promote correct chain pairing in the Fab domain and immunoglobulin.

| | Immunoglobulin | | FAb | |
|---|---|---|---|---|
| | CH1-CK | VH-VL | CH1-CK | VH-VL |
| Variant 1 | — | — | — | — |
| Variant 2 | Set 1 (steric) | — | — | — |
| Variant 3 | Set 1 (steric) | Set 5b (salt) | — | Set 5a (salt) |

TABLE B-continued

Mutational strategies to avoid pairing of the long heavy chain with itself and pairing of L1 with H2 short and promote correct chain pairing in the Fab domain and immunoglobulin.

| | Immunoglobulin | | FAb | |
|---|---|---|---|---|
| | CH1-CK | VH-VL | CH1-CK | VH-VL |
| Variant 4 | Set 1 (steric) | Set 5b (salt) | — | Set 5a (salt) and Set 6 (SS) |
| Variant 5 | Set 2 (hydrophob) | — | Set 3 (salt) | — |
| Variant 6 | Set 2 (hydrophob) | Set 5b (salt) | Set 3 (salt) | Set 5a (salt) |
| Variant 7 | Set 2 (hydrophob) | Set 5b (salt) | Set 3 (salt) | Set 5a (salt) and Set 6 (SS) |
| Variant 8 | — | — | Set 4 (SS) | |
| Variant 9 | Set 1 (steric) | Set 5b (salt) | Set 3 (salt) | Set 5a (salt) |
| Variant 9' | Set 1 (steric) | Set 5b (salt) | Set 3' (charge-alanine) | Set 5a (salt) |
| Variant 10 | Set 1 (steric) | Set 5b (salt) | Set 3 (salt) | Set 5a (salt) and Set 6 (SS) |
| Variant 11 | Set 3 (salt) | Set 5b (salt) | Set 1 (steric) | Set 5a (salt) |
| Variant 12 | Set 3 (salt) | Set 5b (salt) | Set 1 (steric) | Set 5a (salt) and Set 6 (SS) |
| Variant 13 | — | Set 7 (2 x salt) | Set 1 (steric) | Set 5a (salt) |
| Variant 14 | — | Set 7 (2 x salt) | Set 1 (steric) | Set 5a (salt) and Set 6 (SS) |
| Variant 15 | Set 3 (salt) | Set 7 (2 x salt) | Set 1 (steric) | Set 5a (salt) |
| Variant 16 | Set 3 (salt) | Set 7 (2 x salt) | Set 1 (steric) | Set 5a (salt) and Set 6 (SS) |
| Variant 17 | Set 2 (hydrophob) | Set 5b (salt) | Set 1 (steric) and Set 3 (salt) | Set 5a (salt) |
| Variant 18 | Set 2 (hydrophob) | Set 5b (salt) | Set 1 (steric) and Set 3 (salt) | Set 5a (salt) and Set 6 (SS) |
| Variant 19 | Set 1 (steric) and Set 3 (salt) | Set 5b (salt) | Set 2 (hydrophob) | Set 5a (salt) |
| Variant 20 | Set 1 (steric) and Set 3 (salt) | Set 5b (salt) | Set 2 (hydrophob) | Set 5a (salt) and Set 6 (SS) |

In one embodiment, wherein the immunoglobulin comprises (i) a CH1 region;

(ii) a CKappa or CLambda region;

wherein the CH1 region comprises a mutation at position 168 and/or at position 170 (according to EU numbering); and wherein the CKappa or CLambda region comprises a mutation at position 135 and/or at position 176 (according to Kabat numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position H168 and/or at position F170 (according to EU numbering); and wherein the CKappa or CLambda region comprises a mutation at position L135 and/or at position S176 (according to Kabat numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position H168A and/or at position X170G (according to EU numbering); and wherein the CKappa or CLambda region comprises a mutation at position X135Y and/or at position X176W (according to Kabat numbering);

wherein X is any amino acid.

In one embodiment, wherein the immunoglobulin comprises (i) a CH1 region;

(ii) a CKappa or CLambda region;

(iii) a VH region and/or (iv) a VL region;

wherein the CH1 region comprises a mutation at position H168A and/or at position F170G (according to EU numbering); and wherein the CKappa or CLambda region comprises a mutation at position L135Y and/or at position S176W (according to Kabat numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position 168 and/or at position 170 (according to EU numbering);

wherein the CKappa or CLambda region comprises a mutation at position 135 and/or at position 176 (according to Kabat numbering);

wherein the VH region comprises a mutation at position 44 (according to IMGT numbering); and wherein the VL region comprises a mutation at position 44 (according to IMGT numbering);

wherein a Fab comprises (i) a VH region and/or (ii) a VL region;

wherein the VH region comprises a mutation at position 44 (according to IMGT numbering); and wherein the VL region comprises a mutation at position 44 (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position H168 and/or at position F170 (according to EU numbering);

wherein the CKappa or CLambda region comprises a mutation at position L135 and/or at position S176 (according to Kabat numbering);

wherein the VH region comprises a mutation at position Q44 (according to IMGT numbering); and wherein the VL region comprises a mutation at position Q44 (according to IMGT numbering);

wherein a Fab comprises (i) a VH region and/or (ii) a VL region;

wherein the VH region comprises a mutation at position Q44 (according to IMGT numbering); and wherein the VL region comprises a mutation at position Q44 (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position X168A and/or at position X170G (according to EU numbering);

wherein the CKappa or CLambda region comprises a mutation at position X135Y and/or at position X176W (according to Kabat numbering);

wherein the VH region comprises a mutation at position X44E and/or at position X44R (according to IMGT numbering); and wherein the VL region comprises a mutation at position X44E and/or at position X44R (according to IMGT numbering);

wherein a Fab comprises (i) a VH region and/or (ii) a VL region;

wherein the VH region comprises a mutation at position X44E and/or at position X44R (according to IMGT numbering); and wherein the VL region comprises a mutation at position X44E and/or at position X44R (according to IMGT numbering);

wherein X is any amino acid.

In one embodiment, wherein the immunoglobulin comprises (i) a CH1 region;

(ii) a CKappa or CLambda region;

(iii) a VH region and/or (iv) a VL region;

wherein the CH1 region comprises a mutation at position H168A and/or at position F170G (according to EU numbering);

wherein the CKappa or CLambda region comprises a mutation at position L135Y and/or at position S176W (according to Kabat numbering);

wherein the VH region comprises a mutation at position Q44E and/or at position Q44R (according to IMGT numbering); and wherein the VL region comprises a mutation at position Q44E and/or at position Q44R (according to IMGT numbering);

wherein a Fab comprises (i) a VH region and/or (ii) a VL region;

wherein the VH region comprises a mutation at position Q44E and/or at position Q44R (according to IMGT numbering); and wherein the VL region comprises a mutation at position Q44E and/or at position Q44R (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position 168 and/or at position 170 (according to EU numbering);

wherein the CKappa or CLambda region comprises a mutation at position 135 and/or at position 176 (according to Kabat numbering);

wherein the VH region comprises a mutation at position 44 (according to IMGT numbering); and wherein the VL region comprises a mutation at position 44 (according to IMGT numbering);

wherein a Fab comprises (ii) a VH region and/or (ii) a VL region;

wherein the VH region comprises a mutation at position 44 and/or at position 49 (according to IMGT numbering); and wherein the VL region comprises a mutation at position 44 and/or at position 120 (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position H168 and/or at position F170 (according to EU numbering);

wherein the CKappa or CLambda region comprises a mutation at position L135 and/or at position S176 (according to Kabat numbering);

wherein the VH region comprises a mutation at position Q44 (according to IMGT numbering); and wherein the VL region comprises a mutation at position Q44 (according to IMGT numbering);

wherein a Fab comprises (ii) a VH region and/or (ii) a VL region;

wherein the VH region comprises a mutation at position Q44 and/or at position G49 (according to IMGT numbering); and wherein the VL region comprises a mutation at position Q44 at position Q120 (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position X168A and/or at position X170G (according to EU numbering);

wherein the CKappa or CLambda region comprises a mutation at position X135Y and/or at position X176W (according to Kabat numbering);

wherein the VH region comprises a mutation at position X44E and/or at position X44R (according to IMGT numbering); and wherein the VL region comprises a mutation at position X44E and/or at position X44R (according to IMGT numbering);

wherein a Fab comprises (ii) a VH region and/or (ii) a VL region;

wherein the VH region comprises a mutation at position X44E and/or at position X44R and/or at position X49C (according to IMGT numbering); and wherein the VL region comprises a mutation at position X44E and/or at position X44R at position X120K (according to IMGT numbering);

wherein X is any amino acid.

In one embodiment, wherein the immunoglobulin comprises (i) a CH1 region;

(ii) a CKappa or CLambda region;

(iii) a VH region and/or (iv) a VL region;

wherein the CH1 region comprises a mutation at position H168A and/or at position F170G (according to EU numbering);

wherein the CKappa or CLambda region comprises a mutation at position L135Y and/or at position S176W (according to Kabat numbering);

wherein the VH region comprises a mutation at position Q44E and/or at position Q44R (according to IMGT numbering); and wherein the VL region comprises a mutation at position Q44E and/or at position Q44R (according to IMGT numbering);

wherein a Fab comprises (ii) a VH region and/or (ii) a VL region;

wherein the VH region comprises a mutation at position Q44E and/or at position Q44R and/or at position G49C (according to IMGT numbering); and wherein the VL region comprises a mutation at position Q44E and/or at position Q44R at position Q120K (according to IMGT numbering).

In one embodiment, wherein the immunoglobulin comprises (i) a CH1 region;

(ii) a CKappa or CLambda region;

wherein the CH1 region comprises a mutation at position 145 and/or at position 183 (according to EU numbering); and wherein the CKappa or CLambda region comprises a mutation at position 133 and/or at position 176 (according to Kabat numbering);

wherein a Fab comprises (i) the CH1 region;

(ii) the CKappa or CLambda region;

wherein the CH1 region comprises a mutation at position 187; and wherein the CKappa or CLambda region comprises a mutation at position 114 and/or at position 137 (according to Kabat numbering).

In one embodiment, wherein the immunoglobulin comprises (i) a CH1 region;

(ii) a CKappa or CLambda region;

wherein the CH1 region comprises a mutation at position L145 and/or at position S183 (according to EU numbering); and wherein the CKappa or CLambda region comprises a mutation at position V133 and/or at position S176 (according to Kabat numbering);

wherein a Fab comprises (i) the CH1 region;

(ii) the CKappa or CLambda region;

wherein the CH1 region comprises a mutation at position T187; and wherein the CKappa or CLambda region comprises a mutation at position S114 and/or at position N137 (according to Kabat numbering).

In one embodiment, wherein the immunoglobulin comprises (i) a CH1 region;
(ii) a CKappa or CLambda region;
wherein the CH1 region comprises a mutation at position X145Q and/or at position X183V (according to EU numbering); and
wherein the CKappa or CLambda region comprises a mutation at position X133T and/or at position X176V (according to Kabat numbering);
wherein a Fab comprises
(i) the CH1 region;
(ii) the CKappa or CLambda region;
wherein the CH1 region comprises a mutation at position X187E; and
wherein the CKappa or CLambda region comprises a mutation at position X114A and/or at position X137K (according to Kabat numbering);
wherein X is any amino acid.

In one embodiment, wherein the immunoglobulin comprises (i) a CH1 region;
(ii) a CKappa or CLambda region;
wherein the CH1 region comprises a mutation at position L145Q and/or at position S183V (according to EU numbering); and
wherein the CKappa or CLambda region comprises a mutation at position V133T and/or at position S176V (according to Kabat numbering);
wherein a Fab comprises
(i) the CH1 region;
(ii) the CKappa or CLambda region;
wherein the CH1 region comprises a mutation at position T187E; and
wherein the CKappa or CLambda region comprises a mutation at position S114A and/or at position N137K (according to Kabat numbering).

In one embodiment, wherein the immunoglobulin comprises (i) a CH1 region;
(ii) a CKappa or CLambda region;
(iii) a VH region and/or
(iv) a VL region;
wherein the CH1 region comprises a mutation at position 145 and/or at position 183 (according to EU numbering); and
wherein the CKappa or CLambda region comprises a mutation at position 133 and/or at position 176 (according to Kabat numbering);
wherein the VH region comprises a mutation at position 44 (according to IMGT numbering); and
wherein the VL region comprises a mutation at position 44 (according to IMGT numbering);
wherein a Fab comprises
(i) a CH1 region;
(ii) a CKappa or CLambda region;
(iii) a VH region and/or
(iv) a VL region;
wherein the CH1 region comprises a mutation at position 187; and
wherein the CKappa or CLambda region comprises a mutation at position 114 and/or at position 137 (according to Kabat numbering);
wherein the VH region comprises a mutation at position 44 (according to IMGT numbering); and
wherein the VL region comprises a mutation at position 44 (according to IMGT numbering).

In one embodiment, wherein the immunoglobulin comprises (i) a CH1 region;
(ii) a CKappa or CLambda region;
(iii) a VH region and/or
(iv) a VL region;
wherein the CH1 region comprises a mutation at position L145 and/or at position S183 (according to EU numbering); and
wherein the CKappa or CLambda region comprises a mutation at position V133 and/or at position S176 (according to Kabat numbering);
wherein the VH region comprises a mutation at position Q44 (according to IMGT numbering); and
wherein the VL region comprises a mutation at position Q44 (according to IMGT numbering);
wherein a Fab comprises
(i) a CH1 region;
(ii) a CKappa or CLambda region;
(iii) a VH region and/or
(iv) a VL region;
wherein the CH1 region comprises a mutation at position T187; and
wherein the CKappa or CLambda region comprises a mutation at position S114 and/or at position N137 (according to Kabat numbering);
wherein the VH region comprises a mutation at position Q44 (according to IMGT numbering); and
wherein the VL region comprises a mutation at position Q44 (according to IMGT numbering).

In one embodiment, wherein the immunoglobulin comprises (i) a CH1 region;
(ii) a CKappa or CLambda region;
(iii) a VH region and/or
(iv) a VL region;
wherein the CH1 region comprises a mutation at position X145Q and/or at position X183V (according to EU numbering); and
wherein the CKappa or CLambda region comprises a mutation at position X133T and/or at position X176V (according to Kabat numbering);
wherein the VH region comprises a mutation at position X44E and/or at position X44R (according to IMGT numbering); and
wherein the VL region comprises a mutation at position X44E and/or at position X44R (according to IMGT numbering);
wherein a Fab comprises
(i) a CH1 region;
(ii) a CKappa or CLambda region;
(iii) a VH region and/or
(iv) a VL region;
wherein the CH1 region comprises a mutation at position X187E; and
wherein the CKappa or CLambda region comprises a mutation at position X114A and/or at position X137K (according to Kabat numbering)
wherein the VH region comprises a mutation at position X44E and/or at position X44R (according to IMGT numbering); and
wherein the VL region comprises a mutation at position X44E and/or at position X44R (according to IMGT numbering);
wherein X is any amino acid.

In one embodiment, wherein the immunoglobulin comprises (i) a CH1 region;

(ii) a CKappa or CLambda region;

(iii) a VH region and/or (iv) a VL region;

wherein the CH1 region comprises a mutation at position L145Q and/or at position S183V (according to EU numbering); and wherein the CKappa or CLambda region comprises a mutation at position V133T and/or at position S176V (according to Kabat numbering);

wherein the VH region comprises a mutation at position Q44E and/or at position Q44R (according to IMGT numbering); and wherein the VL region comprises a mutation at position Q44E and/or at position Q44R (according to IMGT numbering);

wherein a Fab comprises (i) a CH1 region;

(ii) a CKappa or CLambda region;

(iii) a VH region and/or (iv) a VL region;

wherein the CH1 region comprises a mutation at position T187E; and wherein the CKappa or CLambda region comprises a mutation at position S114A and/or at position N137K (according to Kabat numbering)

wherein the VH region comprises a mutation at position Q44E and/or at position Q44R (according to IMGT numbering); and wherein the VL region comprises a mutation at position Q44E and/or at position Q44R (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position 145 and/or at position 183 (according to EU numbering); and wherein the CKappa or CLambda region comprises a mutation at position 133 and/or at position 176 (according to Kabat numbering);

wherein the VH region comprises a mutation at position 44 (according to IMGT numbering); and wherein the VL region comprises a mutation at position 44 (according to IMGT numbering);

wherein a Fab comprises (i) a CH1 region;

(ii) a CKappa or CLambda region;

(iii) a VH region and/or (iv) a VL region;

wherein the CH1 region comprises a mutation at position 187; and wherein the CKappa or CLambda region comprises a mutation at position 114 and/or at position 137 (according to Kabat numbering);

wherein the VH region comprises a mutation at position 44 and/or at position 49 (according to IMGT numbering); and wherein the VL region comprises a mutation at position 44 at position 120 (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position L145 and/or at position S183 (according to EU numbering); and wherein the CKappa or CLambda region comprises a mutation at position V133 and/or at position S176 (according to Kabat numbering);

wherein the VH region comprises a mutation at position Q44 (according to IMGT numbering); and wherein the VL region comprises a mutation at position Q44 (according to IMGT numbering);

wherein a Fab comprises (i) a CH1 region;

(ii) a CKappa or CLambda region;

(iii) a VH region and/or (iv) a VL region;

wherein the CH1 region comprises a mutation at position T187; and wherein the CKappa or CLambda region comprises a mutation at position S114 and/or at position N137 (according to Kabat numbering);

wherein the VH region comprises a mutation at position Q44 and/or at position G49 (according to IMGT numbering); and wherein the VL region comprises a mutation at position Q44 at position Q120 (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position X145Q and/or at position X183V (according to EU numbering); and wherein the CKappa or CLambda region comprises a mutation at position X133T and/or at position X176V (according to Kabat numbering);

wherein the VH region comprises a mutation at position X44E and/or at position X44R (according to IMGT numbering); and wherein the VL region comprises a mutation at position X44E and/or at position X44R (according to IMGT numbering);

wherein a Fab comprises (i) a CH1 region;

(ii) a CKappa or CLambda region;

(iii) a VH region and/or (iv) a VL region;

wherein the CH1 region comprises a mutation at position X187E; and wherein the CKappa or CLambda region comprises a mutation at position X114A and/or at position X137K (according to Kabat numbering)

wherein the VH region comprises a mutation at position X44E and/or at position X44R and/or at position X49C (according to IMGT numbering); and wherein the VL region comprises a mutation at position X44E and/or at position X44R at position X120K (according to IMGT numbering);

wherein X is any amino acid.

In one embodiment, wherein the immunoglobulin comprises (i) a CH1 region;

(ii) a CKappa or CLambda region;

(iii) a VH region and/or (iv) a VL region;

wherein the CH1 region comprises a mutation at position L145Q and/or at position S183V (according to EU numbering); and wherein the CKappa or CLambda region comprises a mutation at position V133T and/or at position S176V (according to Kabat numbering);

wherein the VH region comprises a mutation at position Q44E and/or at position Q44R (according to IMGT numbering); and wherein the VL region comprises a mutation at position Q44E and/or at position Q44R (according to IMGT numbering);

wherein a Fab comprises (i) a CH1 region;

(ii) a CKappa or CLambda region;

(iii) a VH region and/or (iv) a VL region;

wherein the CH1 region comprises a mutation at position T187E; and wherein the CKappa or CLambda region comprises a mutation at position S114A and/or at position N137K (according to Kabat numbering)

wherein the VH region comprises a mutation at position Q44E and/or at position Q44R and/or at position G49C (according to IMGT numbering); and wherein the VL region comprises a mutation at position Q44E and/or at position Q44R at position Q120K (according to IMGT numbering).

In one embodiment, wherein a Fab comprises (i) a CH1 region;

(ii) a CKappa or CLambda region;

wherein the CH1 region comprises a mutation at position 126; and wherein the CKappa or CLambda region comprises a mutation at position 121 (according to Kabat numbering).

In one embodiment, wherein a Fab comprises (i) a CH1 region;

(ii) a CKappa or CLambda region;

wherein the CH1 region comprises a mutation at position F126; and wherein the CKappa or CLambda region comprises a mutation at position S121 (according to Kabat numbering).

In one embodiment, wherein a Fab comprises (i) a CH1 region;

(ii) a CKappa or CLambda region;

wherein the CH1 region comprises a mutation at position X126C; and wherein the CKappa or CLambda region comprises a mutation at position X121C (according to Kabat numbering);

wherein X is any amino acid.

In one embodiment, wherein a Fab comprises (i) a CH1 region;

(ii) a CKappa or CLambda region;

wherein the CH1 region comprises a mutation at position F126C; and wherein the CKappa or CLambda region comprises a mutation at position S121C (according to Kabat numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position 168 and/or at position 170 (according to EU numbering);

wherein the CKappa or CLambda region comprises a mutation at position 135 and/or at position 176 (according to Kabat numbering);

wherein the VH region comprises a mutation at position 44 (according to IMGT numbering); and wherein the VL region comprises a mutation at position 44 (according to IMGT numbering);

wherein a Fab comprises (i) a CH1 region;

(ii) a CKappa or CLambda region;

(iii) a VH region and/or (iv) a VL region;

wherein the CH1 region comprises a mutation at position 187;

wherein the CKappa or CLambda region comprises a mutation at position 114 and/or at position 137 (according to Kabat numbering);

wherein the VH region comprises a mutation at position 44 (according to IMGT numbering); and wherein the VL region comprises a mutation at position 44 (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position H168 and/or at position F170 (according to EU numbering);

wherein the CKappa or CLambda region comprises a mutation at position L135 and/or at position S176 (according to Kabat numbering);

wherein the VH region comprises a mutation at position Q44 (according to IMGT numbering); and wherein the VL region comprises a mutation at position Q44 (according to IMGT numbering);

wherein a Fab comprises (i) a CH1 region;

(ii) a CKappa or CLambda region;

(iii) a VH region and/or (iv) a VL region;

wherein the CH1 region comprises a mutation at position T187;

wherein the CKappa or CLambda region comprises a mutation at position S114 and/or at position N137 (according to Kabat numbering);

wherein the VH region comprises a mutation at position Q44 (according to IMGT numbering); and wherein the VL region comprises a mutation at position Q44 (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position X168A and/or at position X170G (according to EU numbering);

wherein the CKappa or CLambda region comprises a mutation at position X135Y and/or at position X176W (according to Kabat numbering);

wherein the VH region comprises a mutation at position X44E and/or at position X44R (according to IMGT numbering); and wherein the VL region comprises a mutation at position X44E and/or at position X44R (according to IMGT numbering);

wherein a Fab comprises (i) a CH1 region;

(ii) a CKappa or CLambda region;

(iii) a VH region and/or (iv) a VL region;

wherein the CH1 region comprises a mutation at position X187E;

wherein the CKappa or CLambda region comprises a mutation at position X114A and/or at position X137K (according to Kabat numbering);

wherein the VH region comprises a mutation at position X44E and/or at position X44R (according to IMGT numbering); and wherein the VL region comprises a mutation at position X44E and/or at position X44R (according to IMGT numbering);

wherein X is any amino acid.

In one embodiment, wherein the immunoglobulin comprises (i) a CH1 region;

(ii) a CKappa or CLambda region;

(iii) a VH region and/or (iv) a VL region;

wherein the CH1 region comprises a mutation at position H168A and/or at position F170G (according to EU numbering);

wherein the CKappa or CLambda region comprises a mutation at position L135Y and/or at position S176W (according to Kabat numbering);

wherein the VH region comprises a mutation at position Q44E and/or at position Q44R (according to IMGT numbering); and wherein the VL region comprises a mutation at position Q44E and/or at position Q44R (according to IMGT numbering);

wherein a Fab comprises (i) a CH1 region;

(ii) a CKappa or CLambda region;

(iii) a VH region and/or (iv) a VL region;

wherein the CH1 region comprises a mutation at position T187E;

wherein the CKappa or CLambda region comprises a mutation at position S114A and/or at position N137K (according to Kabat numbering);

wherein the VH region comprises a mutation at position Q44E and/or at position Q44R (according to IMGT numbering); and wherein the VL region comprises a mutation at position Q44E and/or at position Q44R (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position 168 and/or at position 170 (according to EU numbering);

wherein the CKappa or CLambda region comprises a mutation at position 135 and/or at position 176 (according to Kabat numbering);

wherein the VH region comprises a mutation at position 44 (according to IMGT numbering); and wherein the VL region comprises a mutation at position 44 (according to IMGT numbering);

wherein a Fab comprises (i) a CH1 region;

(ii) a CKappa or CLambda region;

(iii) a VH region and/or (iv) a VL region;

wherein the CH1 region comprises a mutation at position 187;

wherein the CKappa or CLambda region comprises a mutation at position 114 and/or at position 137 (according to Kabat numbering);

wherein the VH region comprises a mutation at position 44 and/or at position 49 (according to IMGT numbering); and wherein the VL region comprises a mutation at position 44 at position 120 (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position H168 and/or at position F170 (according to EU numbering);

wherein the CKappa or CLambda region comprises a mutation at position L135 and/or at position S176 (according to Kabat numbering);

wherein the VH region comprises a mutation at position Q44 (according to IMGT numbering); and wherein the VL region comprises a mutation at position Q44 (according to IMGT numbering);

wherein a Fab comprises (i) a CH1 region;

(ii) a CKappa or CLambda region;

(iii) a VH region and/or (iv) a VL region;

wherein the CH1 region comprises a mutation at position T187;

wherein the CKappa or CLambda region comprises a mutation at position S114 and/or at position N137 (according to Kabat numbering);

wherein the VH region comprises a mutation at position Q44 and/or at position G49 (according to IMGT numbering); and wherein the VL region comprises a mutation at position Q44 at position Q120 (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position X168A and/or at position X170G (according to EU numbering);

wherein the CKappa or CLambda region comprises a mutation at position X135Y and/or at position X176W (according to Kabat numbering);

wherein the VH region comprises a mutation at position X44E and/or at position X44R (according to IMGT numbering); and wherein the VL region comprises a mutation at position X44E and/or at position X44R (according to IMGT numbering);

wherein a Fab comprises (i) a CH1 region;

(ii) a CKappa or CLambda region;

(iii) a VH region and/or (iv) a VL region;

wherein the CH1 region comprises a mutation at position X187E;

wherein the CKappa or CLambda region comprises a mutation at position X114A and/or at position X137K (according to Kabat numbering);

wherein the VH region comprises a mutation at position X44E and/or at position X44R and/or at position X49C (according to IMGT numbering); and wherein the VL region comprises a mutation at position X44E and/or at position X44R at position X120K (according to IMGT numbering);

wherein X is any amino acid.

In one embodiment, wherein the immunoglobulin comprises (i) a CH1 region;

(ii) a CKappa or CLambda region;

(iii) a VH region and/or (iv) a VL region;

wherein the CH1 region comprises a mutation at position H168A and/or at position F170G (according to EU numbering);

wherein the CKappa or CLambda region comprises a mutation at position L135Y and/or at position S176W (according to Kabat numbering);

wherein the VH region comprises a mutation at position Q44E and/or at position Q44R (according to IMGT numbering); and wherein the VL region comprises a mutation at position Q44E and/or at position Q44R (according to IMGT numbering);

wherein a Fab comprises (i) a CH1 region;

(ii) a CKappa or CLambda region;

(iii) a VH region and/or (iv) a VL region;

wherein the CH1 region comprises a mutation at position T187E;

wherein the CKappa or CLambda region comprises a mutation at position S114A and/or at position N137K (according to Kabat numbering);

wherein the VH region comprises a mutation at position Q44E and/or at position Q44R and/or at position G49C (according to IMGT numbering); and wherein the VL region comprises a mutation at position Q44E and/or at position Q44R at position Q120K (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position 187 (according to EU numbering);

wherein the CKappa or CLambda region comprises a mutation at position 114 and/or at position 137 (according to Kabat numbering);

wherein the VH region comprises a mutation at position 44 (according to IMGT numbering); and wherein the VL region comprises a mutation at position 44 (according to IMGT numbering);

wherein a Fab comprises (i) a CH1 region;

(ii) a CKappa or CLambda region;

(iii) a VH region and/or (iv) a VL region;

wherein the CH1 region comprises a mutation at position 168 and/or at position 170 (according to EU numbering);

wherein the CKappa or CLambda region comprises a mutation at position 135 and/or at position 176 (according to Kabat numbering);

wherein the VH region comprises a mutation at position 44 (according to IMGT numbering); and wherein the VL region comprises a mutation at position 44 (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position T187 (according to EU numbering);

wherein the CKappa or CLambda region comprises a mutation at position S114 and/or at position N137 (according to Kabat numbering);

wherein the VH region comprises a mutation at position Q44 (according to IMGT numbering); and wherein the VL region comprises a mutation at position Q44 (according to IMGT numbering);

wherein a Fab comprises (i) a CH1 region;

(ii) a CKappa or CLambda region;

(iii) a VH region and/or (iv) a VL region;

wherein the CH1 region comprises a mutation at position H168 and/or at position F170 (according to EU numbering);

wherein the CKappa or CLambda region comprises a mutation at position L135 and/or at position S176 (according to Kabat numbering);

wherein the VH region comprises a mutation at position Q44 (according to IMGT numbering); and wherein the VL region comprises a mutation at position Q44 (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position X187E (according to EU numbering);

wherein the CKappa or CLambda region comprises a mutation at position X114A and/or at position X137K (according to Kabat numbering);

wherein the VH region comprises a mutation at position X44E and/or at position X44R (according to IMGT numbering); and wherein the VL region comprises a mutation at position X44E and/or at position X44R (according to IMGT numbering);

wherein a Fab comprises (i) a CH1 region;

(ii) a CKappa or CLambda region;

(iii) a VH region and/or (iv) a VL region;

wherein the CH1 region comprises a mutation at position X168A and/or at position X170G (according to EU numbering);

wherein the CKappa or CLambda region comprises a mutation at position X135Y and/or at position X176W (according to Kabat numbering);

wherein the VH region comprises a mutation at position X44E and/or at position X44R (according to IMGT numbering); and wherein the VL region comprises a mutation at position X44E and/or at position X44R (according to IMGT numbering);

wherein X is any amino acid.

In one embodiment, wherein the immunoglobulin comprises (i) a CH1 region;

(ii) a CKappa or CLambda region;

(iii) a VH region and/or (iv) a VL region;

wherein the CH1 region comprises a mutation at position T187E (according to EU numbering);

wherein the CKappa or CLambda region comprises a mutation at position S114A and/or at position N137K (according to Kabat numbering);

wherein the VH region comprises a mutation at position Q44E and/or at position Q44R (according to IMGT numbering); and wherein the VL region comprises a mutation at position Q44E and/or at position Q44R (according to IMGT numbering);

wherein a Fab comprises (i) a CH1 region;

(ii) a CKappa or CLambda region;

(iii) a VH region and/or (iv) a VL region;

wherein the CH1 region comprises a mutation at position H168A and/or at position F170G (according to EU numbering);

wherein the CKappa or CLambda region comprises a mutation at position L135Y and/or at position S176W (according to Kabat numbering);

wherein the VH region comprises a mutation at position Q44E and/or at position Q44R (according to IMGT numbering); and wherein the VL region comprises a mutation at position Q44E and/or at position Q44R (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position 187 (according to EU numbering);

wherein the CKappa or CLambda region comprises a mutation at position 114 and/or at position 137 (according to Kabat numbering);

wherein the VH region comprises a mutation at position 44 (according to IMGT numbering); and wherein the VL region comprises a mutation at position 44 (according to IMGT numbering);

wherein a Fab comprises (i) a CH1 region;

(ii) a CKappa or CLambda region;

(iii) a VH region and/or (iv) a VL region;

wherein the CH1 region comprises a mutation at position 168 and/or at position 170 (according to EU numbering);

wherein the CKappa or CLambda region comprises a mutation at position 135 and/or at position 176 (according to Kabat numbering);

wherein the VH region comprises a mutation at position 44 and/or at position 49 (according to IMGT numbering); and wherein the VL region comprises a mutation at position 44 at position 120 (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position T187 (according to EU numbering);

wherein the CKappa or CLambda region comprises a mutation at position S114 and/or at position N137 (according to Kabat numbering);

wherein the VH region comprises a mutation at position Q44 (according to IMGT numbering); and wherein the VL region comprises a mutation at position Q44 (according to IMGT numbering);

wherein a Fab comprises (i) a CH1 region;

(ii) a CKappa or CLambda region;

(iii) a VH region and/or (iv) a VL region;

wherein the CH1 region comprises a mutation at position H168 and/or at position F170 (according to EU numbering);

wherein the CKappa or CLambda region comprises a mutation at position L135 and/or at position S176 (according to Kabat numbering);

wherein the VH region comprises a mutation at position Q44 and/or at position G49 (according to IMGT numbering); and wherein the VL region comprises a mutation at position Q44 at position Q120 (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position X187E (according to EU numbering);

wherein the CKappa or CLambda region comprises a mutation at position X114A and/or at position X137K (according to Kabat numbering);

wherein the VH region comprises a mutation at position X44E and/or at position X44R (according to IMGT numbering); and wherein the VL region comprises a mutation at position X44E and/or at position X44R (according to IMGT numbering);

wherein a Fab comprises (i) a CH1 region;

(ii) a CKappa or CLambda region;

(iii) a VH region and/or (iv) a VL region;

wherein the CH1 region comprises a mutation at position X168A and/or at position X170G (according to EU numbering);

wherein the CKappa or CLambda region comprises a mutation at position X135Y and/or at position X176W (according to Kabat numbering);

wherein the VH region comprises a mutation at position X44E and/or at position X44R and/or at position X49C (according to IMGT numbering); and wherein the VL region comprises a mutation at position X44E and/or at position X44R at position X120K (according to IMGT numbering);

wherein X is any amino acid.

In one embodiment, wherein the immunoglobulin comprises (i) a CH1 region;

(ii) a CKappa or CLambda region;

(iii) a VH region and/or (iv) a VL region;

wherein the CH1 region comprises a mutation at position T187E (according to EU numbering);

wherein the CKappa or CLambda region comprises a mutation at position S114A and/or at position N137K (according to Kabat numbering);

wherein the VH region comprises a mutation at position Q44E and/or at position Q44R (according to IMGT numbering); and wherein the VL region comprises a mutation at position Q44E and/or at position Q44R (according to IMGT numbering);

wherein a Fab comprises (i) a CH1 region;

(ii) a CKappa or CLambda region;

(iii) a VH region and/or (iv) a VL region;

wherein the CH1 region comprises a mutation at position H168A and/or at position F170G (according to EU numbering);

wherein the CKappa or CLambda region comprises a mutation at position L135Y and/or at position S176W (according to Kabat numbering);

wherein the VH region comprises a mutation at position Q44E and/or at position Q44R and/or at position G49C (according to IMGT numbering); and wherein the VL region comprises a mutation at position Q44E and/or at position Q44R at position Q120K (according to IMGT numbering).

In one embodiment, wherein the immunoglobulin comprises (i) a VH region and/or (ii) a VL region;

wherein the VH region comprises a mutation at position 44 and/or at position 120 (according to IMGT numbering); and wherein the VL region comprises a mutation at position 44 and/or at position 49 (according to IMGT numbering);

wherein a Fab comprises (i) a CH1 region;

(ii) a CKappa or CLambda region;

(iii) a VH region and/or (iv) a VL region;

wherein the CH1 region comprises a mutation at position 168 and/or at position 170 (according to EU numbering);

wherein the CKappa or CLambda region comprises a mutation at position 135 and/or at position 176 (according to Kabat numbering);

wherein the VH region comprises a mutation at position 44 (according to IMGT numbering); and wherein the VL region comprises a mutation at position 44 (according to IMGT numbering).

In one embodiment, wherein the immunoglobulin comprises (i) a VH region and/or (ii) a VL region;

wherein the VH region comprises a mutation at position Q44 and/or at position Q120 (according to IMGT numbering); and wherein the VL region comprises a mutation at position Q44 and/or at position A49 (according to IMGT numbering);

wherein a Fab comprises (i) a CH1 region;

(ii) a CKappa or CLambda region;

(iii) a VH region and/or (iv) a VL region;

wherein the CH1 region comprises a mutation at position H168 and/or at position F170 (according to EU numbering);

wherein the CKappa or CLambda region comprises a mutation at position L135 and/or at position S176 (according to Kabat numbering);

wherein the VH region comprises a mutation at position Q44 (according to IMGT numbering); and wherein the VL region comprises a mutation at position Q44 (according to IMGT numbering).

In one embodiment, wherein the immunoglobulin comprises (i) a VH region and/or (ii) a VL region;

wherein the VH region comprises a mutation at position X44K and/or at position X120K (according to IMGT numbering); and wherein the VL region comprises a mutation at position X44D and/or at position X49D (according to IMGT numbering);

wherein a Fab comprises (i) a CH1 region;

(ii) a CKappa or CLambda region;

(iii) a VH region and/or (iv) a VL region;

wherein the CH1 region comprises a mutation at position X168A and/or at position X170G (according to EU numbering);

wherein the CKappa or CLambda region comprises a mutation at position X135Y and/or at position X176W (according to Kabat numbering);

wherein the VH region comprises a mutation at position X44E and/or at position X44R (according to IMGT numbering); and wherein the VL region comprises a mutation at position X44E and/or at position X44R (according to IMGT numbering);

wherein X is any amino acid.

In one embodiment, wherein the immunoglobulin comprises (i) a VH region and/or (ii) a VL region;

wherein the VH region comprises a mutation at position Q44K and/or at position Q120K (according to IMGT numbering); and wherein the VL region comprises a mutation at position Q44D and/or at position A49D (according to IMGT numbering);

wherein a Fab comprises (i) a CH1 region;

(ii) a CKappa or CLambda region;

(iii) a VH region and/or (iv) a VL region;

wherein the CH1 region comprises a mutation at position H168A and/or at position F170G (according to EU numbering);

wherein the CKappa or CLambda region comprises a mutation at position L135Y and/or at position S176W (according to Kabat numbering);

wherein the VH region comprises a mutation at position Q44E and/or at position Q44R (according to IMGT numbering); and wherein the VL region comprises a mutation at position Q44E and/or at position Q44R (according to IMGT numbering).

In one embodiment, wherein the immunoglobulin comprises (i) a VH region and/or (ii) a VL region;

wherein the VH region comprises a mutation at position 44 and/or at position 120 (according to IMGT numbering); and wherein the VL region comprises a mutation at position 44 and/or at position 49 (according to IMGT numbering);

wherein a Fab comprises (i) a CH1 region;

(ii) a CKappa or CLambda region;

(iii) a VH region and/or (iv) a VL region;

wherein the CH1 region comprises a mutation at position 168 and/or at position 170 (according to EU numbering);

wherein the CKappa or CLambda region comprises a mutation at position 135 and/or at position 176 (according to Kabat numbering);

wherein the VH region comprises a mutation at position 44 and/or at position 49 (according to IMGT numbering); and wherein the VL region comprises a mutation at position 44 at position 120 (according to IMGT numbering).

In one embodiment, wherein the immunoglobulin comprises (i) a VH region and/or (ii) a VL region;

wherein the VH region comprises a mutation at position Q44 and/or at position Q120 (according to IMGT numbering); and wherein the VL region comprises a mutation at position Q44 and/or at position A49 (according to IMGT numbering);

wherein a Fab comprises (i) a CH1 region;

(ii) a CKappa or CLambda region;

(iii) a VH region and/or (iv) a VL region;

wherein the CH1 region comprises a mutation at position H168 and/or at position F170 (according to EU numbering);

wherein the CKappa or CLambda region comprises a mutation at position L135 and/or at position S176 (according to Kabat numbering);

wherein the VH region comprises a mutation at position Q44 and/or at position G49 (according to IMGT numbering); and wherein the VL region comprises a mutation at position Q44 at position Q120 (according to IMGT numbering).

In one embodiment, wherein the immunoglobulin comprises (i) a VH region and/or (ii) a VL region;

wherein the VH region comprises a mutation at position X44K and/or at position X120K (according to IMGT numbering); and wherein the VL region comprises a mutation at position X44D and/or at position X49D (according to IMGT numbering);

wherein a Fab comprises (i) a CH1 region;

(ii) a CKappa or CLambda region;

(iii) a VH region and/or (iv) a VL region;

wherein the CH1 region comprises a mutation at position X168A and/or at position X170G (according to EU numbering);

wherein the CKappa or CLambda region comprises a mutation at position X135Y and/or at position X176W (according to Kabat numbering);

wherein the VH region comprises a mutation at position X44E and/or at position X44R and/or at position X49C (according to IMGT numbering); and wherein the VL region comprises a mutation at position X44E and/or at position X44R at position X120K (according to IMGT numbering);

wherein X is any amino acid.

In one embodiment, wherein the immunoglobulin comprises (i) a VH region and/or (ii) a VL region;

wherein the VH region comprises a mutation at position Q44K and/or at position Q120K (according to IMGT numbering); and wherein the VL region comprises a mutation at position Q44D and/or at position A49D (according to IMGT numbering);

wherein a Fab comprises (i) a CH1 region;

(ii) a CKappa or CLambda region;

(iii) a VH region and/or (iv) a VL region;

wherein the CH1 region comprises a mutation at position H168A and/or at position F170G (according to EU numbering);

wherein the CKappa or CLambda region comprises a mutation at position L135Y and/or at position S176W (according to Kabat numbering);

wherein the VH region comprises a mutation at position Q44E and/or at position Q44R and/or at position G49C (according to IMGT numbering); and wherein the VL region comprises a mutation at position Q44E and/or at position Q44R at position Q120K (according to IMGT numbering).

In one embodiment, wherein the immunoglobulin comprises
- (i) a CH1 region;
- (ii) a CKappa or CLambda region;
- (iii) a VH region and/or
- (iv) a VL region;

wherein the CH1 region comprises a mutation at position 187 (according to EU numbering);

wherein the CKappa or CLambda region comprises a mutation at position 114 and/or at position 137 (according to Kabat numbering);

wherein the VH region comprises a mutation at position 44 and/or at position 120 (according to IMGT numbering); and wherein the VL region comprises a mutation at position 44 and/or at position 49 (according to IMGT numbering);

wherein a Fab comprises
- (i) a CH1 region;
- (ii) a CKappa or CLambda region;
- (iii) a VH region and/or
- (iv) a VL region;

wherein the CH1 region comprises a mutation at position 168 and/or at position 170 (according to EU numbering);

wherein the CKappa or CLambda region comprises a mutation at position 135 and/or at position 176 (according to Kabat numbering);

wherein the VH region comprises a mutation at position 44 (according to IMGT numbering); and wherein the VL region comprises a mutation at position 44 (according to IMGT numbering).

In one embodiment, wherein the immunoglobulin comprises
- (i) a CH1 region;
- (ii) a CKappa or CLambda region;
- (iii) a VH region and/or
- (iv) a VL region;

wherein the CH1 region comprises a mutation at position T187 (according to EU numbering);

wherein the CKappa or CLambda region comprises a mutation at position S114 and/or at position N137 (according to Kabat numbering);

wherein the VH region comprises a mutation at position Q44 and/or at position Q120 (according to IMGT numbering); and wherein the VL region comprises a mutation at position Q44 and/or at position A49 (according to IMGT numbering);

wherein a Fab comprises
- (i) a CH1 region;
- (ii) a CKappa or CLambda region;
- (iii) a VH region and/or
- (iv) a VL region;

wherein the CH1 region comprises a mutation at position H168 and/or at position F170 (according to EU numbering);

wherein the CKappa or CLambda region comprises a mutation at position L135 and/or at position S176 (according to Kabat numbering);

wherein the VH region comprises a mutation at position Q44 (according to IMGT numbering); and wherein the VL region comprises a mutation at position Q44 (according to IMGT numbering).

In one embodiment, wherein the immunoglobulin comprises
- (i) a CH1 region;
- (ii) a CKappa or CLambda region;
- (iii) a VH region and/or
- (iv) a VL region;

wherein the CH1 region comprises a mutation at position X187E (according to EU numbering);

wherein the CKappa or CLambda region comprises a mutation at position X114A and/or at position X137K (according to Kabat numbering);

wherein the VH region comprises a mutation at position X44K and/or at position X120K (according to IMGT numbering); and wherein the VL region comprises a mutation at position X44D and/or at position X49D (according to IMGT numbering);

wherein a Fab comprises
- (i) a CH1 region;
- (ii) a CKappa or CLambda region;
- (iii) a VH region and/or
- (iv) a VL region;

wherein the CH1 region comprises a mutation at position X168A and/or at position X170G (according to EU numbering);

wherein the CKappa or CLambda region comprises a mutation at position X135Y and/or at position X176W (according to Kabat numbering);

wherein the VH region comprises a mutation at position X44E and/or at position X44R (according to IMGT numbering); and wherein the VL region comprises a mutation at position X44E and/or at position X44R (according to IMGT numbering);

wherein X is any amino acid.

In one embodiment, wherein the immunoglobulin comprises
- (i) a CH1 region;
- (ii) a CKappa or CLambda region;
- (iii) a VH region and/or
- (iv) a VL region;

wherein the CH1 region comprises a mutation at position T187E (according to EU numbering);

wherein the CKappa or CLambda region comprises a mutation at position S114A and/or at position N137K (according to Kabat numbering);

wherein the VH region comprises a mutation at position Q44K and/or at position 0120K (according to IMGT numbering); and wherein the VL region comprises a mutation at position Q44D and/or at position A49D (according to IMGT numbering);

wherein a Fab comprises
- (i) a CH1 region;
- (ii) a CKappa or CLambda region;
- (iii) a VH region and/or
- (iv) a VL region;

wherein the CH1 region comprises a mutation at position H168A and/or at position F170G (according to EU numbering);

wherein the CKappa or CLambda region comprises a mutation at position L135Y and/or at position S176W (according to Kabat numbering);

wherein the VH region comprises a mutation at position 044E and/or at position Q44R (according to IMGT numbering); and wherein the VL region comprises a mutation at position Q44E and/or at position Q44R (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position 187 (according to EU numbering);

wherein the CKappa or CLambda region comprises a mutation at position 114 and/or at position 137 (according to Kabat numbering);

wherein the VH region comprises a mutation at position 44 and/or at position 120 (according to IMGT numbering); and wherein the VL region comprises a mutation at position 44 and/or at position 49 (according to IMGT numbering);

wherein a Fab comprises (i) a CH1 region;

(ii) a CKappa or CLambda region;

(iii) a VH region and/or (iv) a VL region;

wherein the CH1 region comprises a mutation at position 168 and/or at position 170 (according to EU numbering);

wherein the CKappa or CLambda region comprises a mutation at position 135 and/or at position 176 (according to Kabat numbering);

wherein the VH region comprises a mutation at position 44 and/or at position 49 (according to IMGT numbering); and wherein the VL region comprises a mutation at position 44 at position 120 (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position T187 (according to EU numbering);

wherein the CKappa or CLambda region comprises a mutation at position S114 and/or at position N137 (according to Kabat numbering);

wherein the VH region comprises a mutation at position Q44 and/or at position Q120 (according to IMGT numbering); and wherein the VL region comprises a mutation at position Q44 and/or at position A49 (according to IMGT numbering);

wherein a Fab comprises (i) a CH1 region;

(ii) a CKappa or CLambda region;

(iii) a VH region and/or (iv) a VL region;

wherein the CH1 region comprises a mutation at position H168 and/or at position F170 (according to EU numbering);

wherein the CKappa or CLambda region comprises a mutation at position L135 and/or at position S176 (according to Kabat numbering);

wherein the VH region comprises a mutation at position Q44 and/or at position G49 (according to IMGT numbering); and wherein the VL region comprises a mutation at position Q44 at position Q120 (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position X187E (according to EU numbering);

wherein the CKappa or CLambda region comprises a mutation at position X114A and/or at position X137K (according to Kabat numbering);

wherein the VH region comprises a mutation at position X44K and/or at position X120K (according to IMGT numbering); and wherein the VL region comprises a mutation at position X44D and/or at position X49D (according to IMGT numbering);

wherein a Fab comprises (i) a CH1 region;

(ii) a CKappa or CLambda region;

(iii) a VH region and/or (iv) a VL region;

wherein the CH1 region comprises a mutation at position X168A and/or at position X170G (according to EU numbering);

wherein the CKappa or CLambda region comprises a mutation at position X135Y and/or at position X176W (according to Kabat numbering);

wherein the VH region comprises a mutation at position X44E and/or at position X44R and/or at position X49C (according to IMGT numbering); and wherein the VL region comprises a mutation at position X44E and/or at position X44R at position X120K (according to IMGT numbering);

wherein X is any amino acid.

In one embodiment, wherein the immunoglobulin comprises (i) a CH1 region;

(ii) a CKappa or CLambda region;

(iii) a VH region and/or (iv) a VL region;

wherein the CH1 region comprises a mutation at position T187E (according to EU numbering);

wherein the CKappa or CLambda region comprises a mutation at position S114A and/or at position N137K (according to Kabat numbering);

wherein the VH region comprises a mutation at position Q44K and/or at position Q120K (according to IMGT numbering); and wherein the VL region comprises a mutation at position Q44D and/or at position A49D (according to IMGT numbering);

wherein a Fab comprises (i) a CH1 region;

(ii) a CKappa or CLambda region;

(iii) a VH region and/or (iv) a VL region;

wherein the CH1 region comprises a mutation at position H168A and/or at position F170G (according to EU numbering);

wherein the CKappa or CLambda region comprises a mutation at position L135Y and/or at position S176W (according to Kabat numbering);

wherein the VH region comprises a mutation at position Q44E and/or at position Q44R and/or at position G49C (according to IMGT numbering); and wherein the VL region comprises a mutation at position Q44E and/or at position Q44R at position Q120K (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position 145 and/or at position 183 (according to EU numbering); and wherein the CKappa or CLambda region comprises a mutation at position 133 and/or at position 176 (according to Kabat numbering);

wherein the VH region comprises a mutation at position 44 (according to IMGT numbering); and wherein the VL region comprises a mutation at position 44 (according to IMGT numbering);

wherein a Fab comprises (i) a CH1 region;

(ii) a CKappa or CLambda region;

(iii) a VH region and/or (iv) a VL region;

wherein the CH1 region comprises a mutation at position 168, at position 170 and/or at position 187;

wherein the CKappa or CLambda region comprises a mutation at position 114, at position 135, at position 137, and/or at position 176 (according to Kabat numbering);

wherein the VH region comprises a mutation at position 44 (according to IMGT numbering); and wherein the VL region comprises a mutation at position 44 (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position L145 and/or at position S183 (according to EU numbering); and wherein the CKappa or CLambda region comprises a mutation at position V133 and/or at position S176 (according to Kabat numbering);

wherein the VH region comprises a mutation at position Q44 (according to IMGT numbering); and wherein the VL region comprises a mutation at position Q44 (according to IMGT numbering);

wherein a Fab comprises (i) a CH1 region;

(ii) a CKappa or CLambda region;

(iii) a VH region and/or (iv) a VL region;

wherein the CH1 region comprises a mutation at position H168, at position F170 and/or at position T187;

wherein the CKappa or CLambda region comprises a mutation at position S114, at position L135, at position N137, and/or at position S176 (according to Kabat numbering);

wherein the VH region comprises a mutation at position Q44 (according to IMGT numbering); and wherein the VL region comprises a mutation at position Q44 (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position X145Q and/or at position X183V (according to EU numbering); and wherein the CKappa or CLambda region comprises a mutation at position X133T and/or at position X176V (according to Kabat numbering);

wherein the VH region comprises a mutation at position X44E and/or at position X44R (according to IMGT numbering); and wherein the VL region comprises a mutation at position X44E and/or at position X44R (according to IMGT numbering);

wherein a Fab comprises (i) a CH1 region;

(ii) a CKappa or CLambda region;

(iii) a VH region and/or (iv) a VL region;

wherein the CH1 region comprises a mutation at position X168A, at position X170G and/or at position X187E;

wherein the CKappa or CLambda region comprises a mutation at position X114A, at position X135Y, at position X137K, and/or at position X176W (according to Kabat numbering);

wherein the VH region comprises a mutation at position X44E and/or at position X44R (according to IMGT numbering); and wherein the VL region comprises a mutation at position X44E and/or at position X44R (according to IMGT numbering);

wherein X is any amino acid.

In one embodiment, wherein the immunoglobulin comprises (i) a CH1 region;

(ii) a CKappa or CLambda region;

(iii) a VH region and/or (iv) a VL region;

wherein the CH1 region comprises a mutation at position L145Q and/or at position S183V (according to EU numbering); and wherein the CKappa or CLambda region comprises a mutation at position V133T and/or at position S176V (according to Kabat numbering);

wherein the VH region comprises a mutation at position Q44E and/or at position Q44R (according to IMGT numbering); and wherein the VL region comprises a mutation at position Q44E and/or at position Q44R (according to IMGT numbering);

wherein a Fab comprises (i) a CH1 region;

(ii) a CKappa or CLambda region;

(iii) a VH region and/or (iv) a VL region;

wherein the CH1 region comprises a mutation at position H168A, at position F170G and/or at position T187E;

wherein the CKappa or CLambda region comprises a mutation at position S114A, at position L135Y, at position N137K, and/or at position S176W (according to Kabat numbering);

wherein the VH region comprises a mutation at position Q44E and/or at position Q44R (according to IMGT numbering); and wherein the VL region comprises a mutation at position Q44E and/or at position Q44R (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position 145 and/or at position 183 (according to EU numbering); and wherein the CKappa or CLambda region comprises a mutation at position 133 and/or at position 176 (according to Kabat numbering);

wherein the VH region comprises a mutation at position 44 (according to IMGT numbering); and wherein the VL region comprises a mutation at position 44 (according to IMGT numbering);

wherein a Fab comprises (i) a CH1 region;

(ii) a CKappa or CLambda region;

(iii) a VH region and/or (iv) a VL region;

wherein the CH1 region comprises a mutation at position 168, at position 170 and/or at position 187;

wherein the CKappa or CLambda region comprises a mutation at position 114, at position 135, at position 137, and/or at position 176 (according to Kabat numbering);

wherein the VH region comprises a mutation at position 44 and/or at position 49 (according to IMGT numbering); and wherein the VL region comprises a mutation at position 44 at position 120 (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position L145 and/or at position S183 (according to EU numbering); and wherein the CKappa or CLambda region comprises a mutation at position V133 and/or at position S176 (according to Kabat numbering);

wherein the VH region comprises a mutation at position Q44 (according to IMGT numbering); and wherein the VL region comprises a mutation at position Q44 (according to IMGT numbering);

wherein a Fab comprises (i) a CH1 region;

(ii) a CKappa or CLambda region;

(iii) a VH region and/or (iv) a VL region;

wherein the CH1 region comprises a mutation at position H168, at position F170 and/or at position T187;

wherein the CKappa or CLambda region comprises a mutation at position S114, at position L135, at position N137, and/or at position S176 (according to Kabat numbering);

wherein the VH region comprises a mutation at position Q44 and/or at position G49 (according to IMGT numbering); and wherein the VL region comprises a mutation at position Q44 at position Q120 (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position X145Q and/or at position X183V (according to EU numbering); and wherein the CKappa or CLambda region comprises a mutation at position X133T and/or at position X176V (according to Kabat numbering);

wherein the VH region comprises a mutation at position X44E and/or at position X44R (according to IMGT numbering); and wherein the VL region comprises a mutation at position X44E and/or at position X44R (according to IMGT numbering);

wherein a Fab comprises (i) a CH1 region;

(ii) a CKappa or CLambda region;

(iii) a VH region and/or (iv) a VL region;

wherein the CH1 region comprises a mutation at position X168A, at position X170G and/or at position X187E;

wherein the CKappa or CLambda region comprises a mutation at position X114A, at position X135Y, at position X137K, and/or at position X176W (according to Kabat numbering);

wherein the VH region comprises a mutation at position X44E and/or at position X44R and/or at position X49C (according to IMGT numbering); and wherein the VL region comprises a mutation at position X44E and/or at position X44R at position X120K (according to IMGT numbering);

wherein X is any amino acid.

In one embodiment, wherein the immunoglobulin comprises (i) a CH1 region;

(ii) a CKappa or CLambda region;

(iii) a VH region and/or (iv) a VL region;

wherein the CH1 region comprises a mutation at position L145Q and/or at position S183V (according to EU numbering); and wherein the CKappa or CLambda region comprises a mutation at position V133T and/or at position S176V (according to Kabat numbering);

wherein the VH region comprises a mutation at position Q44E and/or at position Q44R (according to IMGT numbering); and wherein the VL region comprises a mutation at position Q44E and/or at position Q44R (according to IMGT numbering);

wherein a Fab comprises (i) a CH1 region;

(ii) a CKappa or CLambda region;

(iii) a VH region and/or (iv) a VL region;

wherein the CH1 region comprises a mutation at position H168A, at position F170G and/or at position T187E;

wherein the CKappa or CLambda region comprises a mutation at position S114A, at position L135Y, at position N137K, and/or at position S176W (according to Kabat numbering);

wherein the VH region comprises a mutation at position Q44E and/or at position Q44R and/or at position G49C (according to IMGT numbering); and wherein the VL region comprises a mutation at position Q44E and/or at position Q44R at position Q120K (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position 168, at position 170 and/or at position 187 (according to EU numbering); and wherein the CKappa or CLambda region comprises a mutation at position 114, at position 135, at position 137 and/or at position 176 (according to Kabat numbering);

wherein the VH region comprises a mutation at position 44 (according to IMGT numbering); and wherein the VL region comprises a mutation at position 44 (according to IMGT numbering);

wherein a Fab comprises (i) a CH1 region;

(ii) a CKappa or CLambda region;

(iii) a VH region and/or (iv) a VL region;

wherein the CH1 region comprises a mutation at position 145 and/or at position 183 (according to EU numbering);

wherein the CKappa or CLambda region comprises a mutation at position 133 and/or at position 176 (according to Kabat numbering);

wherein the VH region comprises a mutation at position 44 (according to IMGT numbering); and wherein the VL region comprises a mutation at position 44 (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position H168, at position F170 and/or at position T187 (according to EU numbering); and wherein the CKappa or CLambda region comprises a mutation at position S114, at position V135, at position N137 and/or at position S176 (according to Kabat numbering);

wherein the VH region comprises a mutation at position Q44 (according to IMGT numbering); and wherein the VL region comprises a mutation at position Q44 (according to IMGT numbering);

wherein a Fab comprises (i) a CH1 region;

(ii) a CKappa or CLambda region;

(iii) a VH region and/or (iv) a VL region;

wherein the CH1 region comprises a mutation at position L145 and/or at position S183 (according to EU numbering);

wherein the CKappa or CLambda region comprises a mutation at position V133 and/or at position S176 (according to Kabat numbering);

wherein the VH region comprises a mutation at position Q44 (according to IMGT numbering); and wherein the VL region comprises a mutation at position Q44 (according to IMGT numbering).

In one embodiment, wherein the immunoglobulin comprises (i) a CH1 region;

(ii) a CKappa or CLambda region;

(iii) a VH region and/or (iv) a VL region;

wherein the CH1 region comprises a mutation at position X168A, at position X170G and/or at position X187E (according to EU numbering); and wherein the CKappa or CLambda region comprises a mutation at position X114A, at position X135Y, at position X137K and/or at position X176W (according to Kabat numbering);

wherein the VH region comprises a mutation at position X44E and/or at position X44R (according to IMGT numbering); and wherein the VL region comprises a mutation at position X44E and/or at position X44R (according to IMGT numbering);

wherein a Fab comprises (i) a CH1 region;

(ii) a CKappa or CLambda region;

(iii) a VH region and/or (iv) a VL region;

wherein the CH1 region comprises a mutation at position X145Q and/or at position X183V (according to EU numbering);

wherein the CKappa or CLambda region comprises a mutation at position X133T and/or at position X176V (according to Kabat numbering);

wherein the VH region comprises a mutation at position X44E and/or at position X44R (according to IMGT numbering); and wherein the VL region comprises a mutation at position X44E and/or at position X44R (according to IMGT numbering);

wherein X is any amino acid.

In one embodiment, wherein the immunoglobulin comprises (i) a CH1 region;

(ii) a CKappa or CLambda region;

(iii) a VH region and/or (iv) a VL region;

wherein the CH1 region comprises a mutation at position H168A, at position F170G and/or at position T187E (according to EU numbering); and wherein the CKappa or CLambda region comprises a mutation at position S114A, at position V135Y, at position N137K and/or at position S176W (according to Kabat numbering);

wherein the VH region comprises a mutation at position Q44E and/or at position Q44R (according to IMGT numbering); and wherein the VL region comprises a mutation at position Q44E and/or at position Q44R (according to IMGT numbering);

wherein a Fab comprises
(i) a CH1 region;
(ii) a CKappa or CLambda region;
(iii) a VH region and/or
(iv) a VL region;
wherein the CH1 region comprises a mutation at position
L145Q and/or at position S183V (according to EU
numbering);
wherein the CKappa or CLambda region comprises a
mutation at position V133T and/or at position S176V
(according to Kabat numbering);
wherein the VH region comprises a mutation at position
Q44E and/or at position Q44R (according to IMGT
numbering); and
wherein the VL region comprises a mutation at position
Q44E and/or at position Q44R (according to IMGT
numbering).
In one embodiment, wherein the immunoglobulin com-
prises
(i) a CH1 region;
(ii) a CKappa or CLambda region;
(iii) a VH region and/or
(iv) a VL region;
wherein the CH1 region comprises a mutation at position
168, at position 170 and/or at position 187 (according
to EU numbering); and
wherein the CKappa or CLambda region comprises a
mutation at position 114, at position 135, at position
137 and/or at position 176 (according to Kabat num-
bering);
wherein the VH region comprises a mutation at position
44 (according to IMGT numbering); and
wherein the VL region comprises a mutation at position
44 (according to IMGT numbering);
wherein a Fab comprises
(i) a CH1 region;
(ii) a CKappa or CLambda region;
(iii) a VH region and/or
(iv) a VL region;
wherein the CH1 region comprises a mutation at position
145 and/or at position 183 (according to EU number-
ing);
wherein the CKappa or CLambda region comprises a
mutation at position 133 and/or at position 176 (accord-
ing to Kabat numbering);
wherein the VH region comprises a mutation at position
44 and/or at position 49 (according to IMGT number-
ing); and
wherein the VL region comprises a mutation at position
44 and/or position 120 (according to IMGT number-
ing).
In one embodiment, wherein the immunoglobulin com-
prises
(i) a CH1 region;
(ii) a CKappa or CLambda region;
(iii) a VH region and/or
(iv) a VL region;
wherein the CH1 region comprises a mutation at position
H168, at position F170 and/or at position T187 (accord-
ing to EU numbering); and
wherein the CKappa or CLambda region comprises a
mutation at position S114, at position V135, at position
N137 and/or at position S176 (according to Kabat
numbering);
wherein the VH region comprises a mutation at position
Q44 (according to IMGT numbering); and wherein the VL region comprises a mutation at position
Q44 (according to IMGT numbering);
wherein a Fab comprises
(i) a CH1 region;
(ii) a CKappa or CLambda region;
(iii) a VH region and/or
(iv) a VL region;
wherein the CH1 region comprises a mutation at position
L145 and/or at position S183 (according to EU num-
bering);
wherein the CKappa or CLambda region comprises a
mutation at position V133 and/or at position S176
(according to Kabat numbering);
wherein the VH region comprises a mutation at position
Q44 and/or at position G49 (according to IMGT num-
bering); and
wherein the VL region comprises a mutation at position
Q44 and/or position Q120 (according to IMGT num-
bering).
In one embodiment, wherein the immunoglobulin com-
prises
(i) a CH1 region;
(ii) a CKappa or CLambda region;
(iii) a VH region and/or
(iv) a VL region;
wherein the CH1 region comprises a mutation at position
X168A, at position X170G and/or at position X187E
(according to EU numbering); and
wherein the CKappa or CLambda region comprises a
mutation at position X114A, at position X135Y, at
position X137K and/or at position X176W (according
to Kabat numbering);
wherein the VH region comprises a mutation at position
X44E and/or at position X44R (according to IMGT
numbering); and
wherein the VL region comprises a mutation at position
X44E and/or at position X44R (according to IMGT
numbering);
wherein a Fab comprises
(i) a CH1 region;
(ii) a CKappa or CLambda region;
(iii) a VH region and/or
(iv) a VL region;
wherein the CH1 region comprises a mutation at position
X145Q and/or at position X183V (according to EU
numbering);
wherein the CKappa or CLambda region comprises a
mutation at position X133T and/or at position X176V
(according to Kabat numbering);
wherein the VH region comprises a mutation at position
X44E and/or at position X44R and/or at position X49C
(according to IMGT numbering); and
wherein the VL region comprises a mutation at position
X44E and/or at position X44R at position X120K
(according to IMGT numbering);
wherein X is any amino acid.
In one embodiment, wherein the immunoglobulin com-
prises
(i) a CH1 region;
(ii) a CKappa or CLambda region;
(iii) a VH region and/or
(iv) a VL region;
wherein the CH1 region comprises a mutation at position
H168A, at position F170G and/or at position T187E
(according to EU numbering); and wherein the CKappa or CLambda region comprises a mutation at position S114A, at position V135Y, at position N137K and/or at position S176W (according to Kabat numbering);

wherein the VH region comprises a mutation at position Q44E and/or at position Q44R (according to IMGT numbering); and wherein the VL region comprises a mutation at position Q44E and/or at position Q44R (according to IMGT numbering);

wherein a Fab comprises (i) a CH1 region;

(ii) a CKappa or CLambda region;

(iii) a VH region and/or (iv) a VL region;

wherein the CH1 region comprises a mutation at position L145Q and/or at position S183V (according to EU numbering);

wherein the CKappa or CLambda region comprises a mutation at position V133T and/or at position S176V (according to Kabat numbering);

wherein the VH region comprises a mutation at position Q44E and/or at position Q44R and/or at position G49C (according to IMGT numbering); and wherein the VL region comprises a mutation at position Q44E and/or at position Q44R at position Q120K (according to IMGT numbering).

In a further embodiment, the VH region of (a) and/or (b) comprises a mutation at position 65. Preferably, the VH region of (a) and/or (b) comprises a mutation at position T65. Most preferably, the VH region of (a) and/or (b) comprises a mutation at position X65A or X65E, wherein X is any amino acid (for example, T65A or T65E). Surprisingly, the inventors found that molecules with this mutation at position 65 showed improved purity after protein A purification.

In a further embodiment, the VH region comprises one or more of the following mutations: X44R/E/D/K, X49C, and X120K; and/or the VL region comprises one or more of the following mutations: X44R/E/D/K, X49D X120C; and/or the CH1 region comprises one or more of the following mutations: H168A/G, F170G/A, L145Q, S183V, T187E/D, X168A/G, X170G/A, X145Q, X183V, X187E/D; and/or the CKappa or CLambda region comprises one or more of the following mutations: S/T114A, V133T, L135Y/W, N/S137K/R/H, S176W/V/Y, X114A, X133T, X135Y/W, X137K/R/H, X176W/V/Y, wherein X is any amino acid.

The mutations described herein are associated with particular numbering systems (such as IMGT numbering), which allows the skilled person to implement those mutations to any antibody. For example, the person skilled in the art would understand these numbering systems and the sequence of any particular antibody enough to be able to deduce which amino acid is present at any given position. This is possible since the immunoglobulin structure has many conserved features which have been considered when generating the different numbering systems. Some positions are conserved for basically all natural antibodies, regardless of antigen target, species or type.

In one embodiment, the above mutations are given relative to the following reference sequences:

```
Reference sequence VH (SEQ ID NO: 1):
EVQLLESGGGLVQPGGSLRLSCAASGFTFSSYAMSWVRQAPGKGLEWVS

AISGSGGSTYYADSVKGRFTISRDNSKNTLYLQMNSLRAEDTAVYYCAR

YVNFGMDYWGQGTLVTVSS

Reference sequence VL (SEQ ID NO: 2):
DIQMTQSPSSLSASVGDRVTITCRASQSISSYLNWYQQKPGKAPKLLIY

AASSLQSGVPSRFSGSGSGTDFTLTISSLQPEDFATYYCQQSYSTPYTF

GQGTKLEIK

Reference sequence CH1 (SEQ ID NO: 3):
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSC
(wherein the bold and underlined section is part
of the hinge region, but is present in the Fab
fragment)

Reference sequence CKappa (SEQ ID NO: 4):
RTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPV

TKSFNRGEC

Reference sequence CLambda 1 (SEQ ID NO: 59)
GQPKANPTVTLFPPSSEELQANKATLVCLISDFYPGAVTVAWKADGSPV

KAGVETTKPSKQSNNKYAASSYLSLTPEQWKSHRSYSCQVTHEGSTVEK

TVAPTECS

Reference sequence CLambda 2 (SEQ ID NO: 60)
GQPKAAPSVTLFPPSSEELQANKATLVCLISDFYPGAVTVAWKADSSPV

KAGVETTTPSKQSNNKYAASSYLSLTPEQWKSHRSYSCQVTHEGSTVEK

TVAPTECS

Reference sequence CLambda 3 (SEQ ID NO: 61)
GQPKAAPSVTLFPPSSEELQANKATLVCLISDFYPGAVTVAWKADSSPV

KAGVETTTPSKQSNNKYAASSYLSLTPEQWKSHKSYSCQVTHEGSTVEK

TVAPTECS
```

In one embodiment, the one or more Fab fragment(s) is linked to the C-terminal end of the immunoglobulin via a linker. Accordingly, the linker may be a peptide linker linking the second light chain polypeptide to the first heavy chain polypeptide. In one embodiment, where there are two Fab fragments (and therefore two second light chain polypeptides), and wherein there are also two first heavy chain polypeptides in the immunoglobulin, each Fab fragment is attached to one of the first heavy chain polypeptides via a linker.

In one embodiment, the linker is a peptide with an amino acid sequence selected from:

```
                                        (SEQ ID NO: 5)
        SGGGGSGGGGS, (SEQ ID NO: 6)
        SGGGGSGGGGSAP, (SEQ ID NO: 7)
        NFSQP, (SEQ ID NO: 8)
        KRTVA,
```

47

-continued

```
                                    (SEQ ID NO: 9)
GGGGSGGGGSGGGGS,
(SG)m, where m = 1 to 7 or (SEQ ID NO: 34)
GGGGSGGGGS.
```

Binding Properties

In one embodiment of the first aspect of the invention, the bispecific antibody is tetravalent, capable of binding bivalently to each of the two antigens.

In one embodiment, the bispecific antibody comprises an immunoglobulin arranged as an antibody with two arms and therefore two binding sites for the first antigen, and two of the Fab fragments, each providing a binding site for the second antigen. Thus, there are two binding sites for the first antigen and two binding sites for the second antigen.

In one embodiment, the first and/or second antigen is an immunomodulator.

By "immunomodulator" we mean a target which is capable of modifying the immune response or the functioning of the immune system. In one embodiment, the immunomodulator is a checkpoint molecule. By "checkpoint molecule" we mean a regulator of the immune system.

It will be appreciated by persons skilled in the art that the checkpoint molecule may either be a stimulatory or inhibitory checkpoint molecule.

Thus, in one embodiment, the checkpoint molecule is a stimulatory checkpoint molecule, optionally selected from CD40, CD137, GITR, CD27, ICOS and OX40.

In an alternative embodiment, the checkpoint molecule is an inhibitory checkpoint molecule, optionally selected from CTLA-4, PD-1, Tim3, Lag3, TIGIT and VISTA.

In one embodiment of the first aspect of the invention, the first and/or second antigen is a tumour cell-associated antigen.

Accordingly, the tumour cell-associated antigen may be selected from the group consisting of:
(a) products of mutated oncogenes and tumour suppressor genes;
(b) overexpressed or aberrantly expressed cellular proteins;
(c) tumour antigens produced by oncogenic viruses;
(d) oncofetal antigens;
(e) altered cell surface glycolipids and glycoproteins;
(f) cell type-specific differentiation antigens;
(g) hypoxia-induced antigens;
(h) tumour peptides presented by MHC class I;
(i) epithelial tumour antigens;
(j) haematological tumour-associated antigens;
(k) cancer testis antigens; and
(l) melanoma antigens.

Specific examples of tumour-associated antigens which the first or second antigen may be selected from include 5T4, CD20, CD19, MUC1, CA-125, CO17-1A, EpCAM, HER2, EphA2, EphA3, DR5, FAP, OGD2, VEGFR, Her3, mesothelin and EGFR.

In one embodiment of the invention, the first and second antigen are selected from the group of antigens consisting of: CD40, EpCAM, 5T4, CD137, OX40, CTLA-4, GITR, EGFR and HER2.

Thus, in one embodiment of the first aspect of the invention, the bispecific antibody targets a pair of antigens selected from: OX40 and CTLA-4, OX40 and CD137, GITR and CTLA-4, CD137 and CTLA-4, OX40 and 5T4, 5T4 and CD137, and CD137 and 5T4.

In a preferred embodiment, the first and second antigen are selected from CD40 and EpCAM. For example, the first antigen (targeted by the immunoglobulin) may be CD40 and the second antigen (targeted by the Fab) may be EpCAM.

Thus, in one embodiment, the bispecific antibody targets CD40 as one of the target antigens, and comprises one or more of the following CDR sequences:

| CDRH1 | GFTFSSYA (SEQ ID NO: 10) |
|---|---|
| CDRH2 | IGSYGGGT (SEQ ID NO: 11) |
| CDRH3 | ARYVNFGMDY (SEQ ID NO: 12) |
| CDRL1 | QSISSY (SEQ ID NO: 13) |
| CDRL2 | AAS (SEQ ID NO: 14) |
| CDRL3 | QQYGRNPPT (SEQ ID NO: 15) |

In one embodiment, the bispecific antibody comprises all 6 of the above CDR sequences (SEQ ID NOs: 10 to 15).

The above CDR sequences are the CDR sequences of a CD40-binding portion. Optionally this CD40 binding portion comprises the following variable heavy sequence and/or the following variable light sequence:

```
1132 VH (SEQ ID NO: 16):
EVQLLESGGGLVQPGGSLRLSCAASGFTFSSYAMSWVRQAPGKGLEWVS

GIGSYGGGTYYADSVKGRFTISRDNSKNTLYLQMNSLRAEDTAVYYCAR

YVNFGMDYWGQGTLVTVSS

1132 VL (also known as 1133) (SEQ ID NO: 17):
DIQMTQSPSSLSASVGDRVTITCRASQSISSYLNWYQQKPGKAPKLLIY

AASSLQSGVPSRFSGSGSGTDFTLTISSLQPEDFATYYCQQYGRNPPTF

GQGTKLEIK
```

In one embodiment, the bispecific antibody targets EpCAM as one of the target antigens, and comprises one of more of the following CDR sequences:

| CDRH1 | GYAFTNYW (SEQ ID NO: 18) |
|---|---|
| CDRH2 | IFPGSGNI (SEQ ID NO: 19) |
| CDRH3 | ARLRNWDEPMDY (SEQ ID NO: 20) |
| CDRL1 | QSLLNSGNQKNY (SEQ ID NO: 21) |
| CDRL2 | WAS (SEQ ID NO: 22) |
| CDRL3 | QNDYSYPLT (SEQ ID NO: 23) |

In one embodiment, the bispecific antibody comprises all 6 of the above CDR sequences (SEQ ID NOs: 18 to 23).

The above CDR sequences are the CDR sequences of an EpCAM-binding portion. Optionally this EpCAM-binding portion comprises the following variable heavy sequence and/or the following variable light sequence:

```
EpCAM-binding VH (also known as Solitumab VH)
(SEQ ID NO: 24):
EVQLLEQSGAELVRPGTSVKISCKASGYAFTNYWLGWVKQRPGHGLEWI

GDIFPGSGNIHYNEKFKGKATLTADKSSSTAYMQLSSLTFEDSAVYFCA

RLRNWDEPMDYWGQGTTVTVSS

EpCAM-binding VL (also known as Solitumab VL)
(SEQ ID NO: 25):
ELVMTQSPSSLTVTAGEKVTMSCKSSQSLLNSGNQKNYLTWYQQKPGQP

PKLLIYWASTRESGVPDRFTGSGSGTDFTLTISSVQAEDLAVYYCQNDY

PLTFGAGTKLEIK
```

Thus, in one embodiment, the bispecific antibody comprises:

(a) a first heavy chain polypeptide comprising or consisting of the amino acid sequence of SEQ ID NO: 16; and/or (b) a first light chain polypeptide comprising or consisting of the amino acid sequence of SEQ ID NO: 17; and/or (c) a second heavy chain polypeptide comprising or consisting of the amino acid sequence of SEQ ID NO: 24; and/or (d) a second light chain polypeptide comprising or consisting of the amino acid sequence of SEQ ID NO: 25.

In one embodiment, the bispecific antibody targets CD137 as one of the target antigens, and comprises one or more of the following CDR sequences:

| | |
|---|---|
| CDRH1 | GFTFSYGS (SEQ ID NO: 35) |
| CDRH2 | ISSGSGST (SEQ ID NO: 36) |
| CDRH3 | ARSSYYGSYYSIDY (SEQ ID NO: 37) |
| CDRL1 | QSISSY (SEQ ID NO: 13) |
| CDRL2 | AAS (SEQ ID NO: 14) |
| CDRL3 | QQYYDNLPT (SEQ ID NO: 38) |

In one embodiment, the bispecific antibody comprises all 6 of the above CDR sequences (SEQ ID NOs: 13, 14 and 35 to 38).

The above CDR sequences are the CDR sequences of a CD137-binding portion. Optionally this CD137 binding portion comprises the following variable heavy sequence and/or the following variable light sequence:

```
1618 VH (SEQ ID NO: 39):
EVQLLESGGGLVQPGGSLRLSCAASGFTFSYGSMYWVRQAPGKGLEWVS

SISSGSGSTYYADSVKGRFTISRDNSKNTLYLQMNSLRAEDTAVYYCAR

SSYYGSYYSIDYWGQGTLVTVSS

1816 VL (also known as 1619) (SEQ ID NO: 40):
DIQMTQSPSSLSASVGDRVTITCRASQSISSYLNWYQQKPGKAPKLLIY

AASSLQSGVPSRFSGSGSGTDFTLTISSLQPEDFATYYCQQYYDNLPTF

GQGTKLEIK
```

In one embodiment, the bispecific antibody targets 5T4 as one of the target antigens, and comprises one or more of the following CDR sequences:

| | |
|---|---|
| CDRH1 | GFTFSSYAM (SEQ ID NO: 41) |
| CDRH2 | ISGSGGST (SEQ ID NO: 42) |
| CDRH3 | ARYYGGYYSAWMDY (SEQ ID NO: 43) |
| CDRL1 | QSISSY (SEQ ID NO: 13) |
| CDRL2 | AAS (SEQ ID NO: 14) |
| CDRL3 | QQTYGYLHT (SEQ ID NO: 44) |

In one embodiment, the bispecific antibody comprises all 6 of the above CDR sequences (SEQ ID NOs: 13, 14 and 41 to 44).

The above CDR sequences are the CDR sequences of a 5T4-binding portion. Optionally this 5T4 binding portion comprises the following variable heavy sequence and/or the following variable light sequence:

```
1210 VH (SEQ ID NO: 45):
EVQLLESGGGLVQPGGSLRLSCAASGFTFSSYAMSWVRQAPGKGLEWVS

AISGSGGSTYYADSVKGRFTISRDNSKNTLYLQMNSLRAEDTAVYYCAR

YYGGYYSAWMDYWGQGTLVTVSS

1210 VL (also known as 1211) (SEQ ID NO: 46):
DIQMTQSPSSLSASVGDRVTITCRASQSISSYLNWYQQKPGKAPKLLIY

AASSLQSGVPSRFSGSGSGTDFTLTISSLQPEDFATYYCQQTYGYLHTF

GQGTKLEIK
```

In one embodiment, the bispecific antibody targets OX40 as one of the target antigens, and comprises one or more of the following CDR sequences:

| | |
|---|---|
| CDRH1 | GFTFGGYYM (SEQ ID NO: 47) |
| CDRH2 | IPGSGGST (SEQ ID NO: 48) |
| CDRH3 | ARYDYYWMDY (SEQ ID NO: 49) |
| CDRL1 | QSISSY (SEQ ID NO: 13) |
| CDRL2 | AAS (SEQ ID NO: 14) |
| CDRL3 | QQGHGSYPHT (SEQ ID NO: 50) |

In one embodiment, the bispecific antibody comprises all 6 of the above CDR sequences (SEQ ID NOs: 13, 14 and 47 to 50).

The above CDR sequences are the CDR sequences of an OX40-binding portion. Optionally this OX40 binding portion comprises the following variable heavy sequence and/or the following variable light sequence:

```
1170 VH (SEQ ID NO: 51):
EVQLLESGGGLVQPGGSLRLSCAASGFTFGGYYMSWVRQAPGKGLEWVS

YIPGSGGSTYYADSVKGRFTISRDNSKNTLYLQMNSLRAEDTAVYYCAR

YDYYWMDYWGQGTLVTVSS
```

```
-continued
1170 VL (also known as 1171) (SEQ ID NO: 52):
DIQMTQSPSSLSASVGDRVTITCRASQSISSYLNWYQQKPGKAPKLLIY

AASSLQSGVPSRFSGSGSGTDFTLTISSLQPEDFATYYCQQGHGSYPHT

FGQGTKLEIK
```

In one embodiment, the bispecific antibody targets CD137 as one of the target antigens, and comprises one or more of the following CDR sequences:

| CDRH1 | GFTFSSYYM (SEQ ID NO: 53) |
| CDRH2 | IGSYYGYT (SEQ ID NO: 54) |
| CDRH3 | ARAYYDYNYYYAYFDY (SEQ ID NO: 55) |
| CDRL1 | QSISSY (SEQ ID NO: 13) |
| CDRL2 | AAS (SEQ ID NO: 14) |
| CDRL3 | QQSVPHYPFT (SEQ ID NO: 56) |

In one embodiment, the bispecific antibody comprises all 6 of the above CDR sequences (SEQ ID NOs: 13, 14 and 53 to 56).

The above CDR sequences are the CDR sequences of an CD137-binding portion. Optionally this CD137 binding portion comprises the following variable heavy sequence and/or the following variable light sequence:

```
1204 VH (SEQ ID NO: 57):
EVQLLESGGGLVQPGGSLRLSCAASGFTFSSYYMGWVRQAPGKGLEWVS

GIGSYYGYTGYADSVKGRFTISRDNSKNTLYLQMNSLRAEDTAVYYCAR

AYYDYNYYYAYFDYWGQGTLVTVSS

1204 VL (also known as 1205) (SEQ ID NO: 58):
DIQMTQSPSSLSASVGDRVTITCRASQSISSYLNWYQQKPGKAPKLLIY

AASSLQSGVPSRFSGSGSGTDFTLTISSLQPEDFATYYCQQSVPHYPFT

FGQGTKLEIK
```

Variants

The bispecific antibodies or constituent binding domains thereof (such as the EpCAM- or CD40-binding domains) described herein may comprise a variant or a fragment of any of the specific amino acid sequences recited herein, provided that the polypeptide or binding domain retains binding to its target. In one embodiment, the variant of an antibody or antigen-binding fragment may retain the CDR sequences of the sequences recited herein.

A fragment of any one of the heavy or light chain amino acid sequences recited herein may comprise at least 7, at least 8, at least 9, at least 10, at least 12, at least 15, at least 18, at least 20, at least 25, at least 50, at least 60, at least 70, at least 80, at least 90 or at least 100 consecutive amino acids from the said amino acid sequence.

A variant of any one of the heavy or light chain amino acid sequences recited herein may be a substitution, deletion or addition variant of said sequence. A variant may comprise 1, 2, 3, 4, 5, up to 10, up to 20, up to 30 or more amino acid substitutions and/or deletions from the said sequence. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

| Ala, A | aliphatic, hydrophobic, neutral | Met, M | hydrophobic, neutral |
| Cys, C | polar, hydrophobic, neutral | Asn, N | polar, hydrophilic, neutral |
| Asp, D | polar, hydrophilic, charged (−) | Pro, P | hydrophobic, neutral |
| Glu, E | polar, hydrophilic, charged −) | Gin, Q | polar, hydrophilic, neutral |
| Phe, F | aromatic, hydrophobic, neutral | Arg, R | polar, hydrophilic, charged (+) |
| Gly, G | aliphatic, neutral | Ser, S | polar, hydrophilic, neutral |
| His, H | aromatic, polar, hydrophilic, charged (+) | Thr, T | polar, hydrophilic, neutral |
| Ile, I | aliphatic, hydrophobic, neutral | Val, V | aliphatic, hydrophobic, neutral |
| Lys, K | polar, hydrophilic, charged(+) | Trp, W | aromatic, hydrophobic, neutral |
| Leu, L | aliphatic, hydrophobic, neutral | Tyr, Y | aromatic, polar, hydrophobic |

Amino acids herein may be referred to by full name, three letter code or single letter code.

Preferred "derivatives" or "variants" include those in which instead of the naturally occurring amino acid the amino acid which appears in the sequence is a structural analogue thereof. Amino acids used in the sequences may also be derivatised or modified, e.g. labelled, providing the function of the antibody is not significantly adversely affected.

Derivatives and variants as described above may be prepared during synthesis of the antibody or by post-production modification, or when the antibody is in recombinant form using the known techniques of site-directed mutagenesis, random mutagenesis, or enzymatic cleavage and/or ligation of nucleic acids.

Preferably, variants have an amino acid sequence which has more than 60%, or more than 70%, e.g. 75 or 80%, preferably more than 85%, e.g. more than 90 or 95% amino acid identity to a sequence as shown in the sequences disclosed herein. This level of amino acid identity may be seen across the full length of the relevant SEQ ID NO sequence or over a part of the sequence, such as across 20, 30, 50, 75, 100, 150, 200 or more amino acids, depending on the size of the full-length polypeptide.

In connection with amino acid sequences, "sequence identity" refers to sequences which have the stated value when assessed using ClustalW (Thompson et al., 1994, *Nucleic Acids Res.* 22(22):4673-80; the disclosures of which are incorporated herein by reference) with the following parameters:

Pairwise alignment parameters—Method: accurate, Matrix: PAM, Gap open penalty: 10.00, Gap extension penalty: 0.10;

Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: GPSNDQEKR. Sequence identity at a particular residue is intended to include identical residues which have simply been derivatised.

Functional Properties

It will also be appreciated by persons skilled in the art that the bispecific antibody of the first aspect of the invention may be defined in relation to its functional properties and effects.

In one embodiment, the bispecific antibody of the first aspect of the invention is capable of inducing antibody-dependent cell cytotoxicity (ADCC), antibody-dependent cellular phagocytosis (ADCP), complement-dependent cytotoxicity (CDC), and/or apoptosis.

In one embodiment, the bispecific antibody is capable of inducing:

(a) activation of B cells; and/or (b) activation of dendritic cells; and/or (c) activation of cytotoxic T cells, i.e. CD8+ T cells; and/or (d) activation of helper T cells, i.e. CD4+ T cells; and/or (e) improved tumour antigen cross-presentation by dendritic cells; and/or (f) expansion of tumour antigen-specific T cells; and/or (g) direct tumour cell killing via ADCC and/or via inhibition of tumour growth and survival signals; and/or (h) anti-angiogenic effects via interaction with endothelial and/or stromal cells; and/or (i) activation of natural killer cells; and/or (j) Treg depletion; and/or (k) reprograming of Tregs into effector T cells; and/or (l) depletion of tumour myeloid cell populations; and/or (m) reprogramming of tumour myeloid cell populations; and/or (n) internalisation of tumour debris by antigen-presenting cells; and/or (o) internalisation of tumour extracellular vesicles, e.g. exosomes, by antigen-presenting cells; and/or (p) localization to tumour tissue by binding to tumour cells.

Methodologies for determining whether the bispecific antibody is capable of inducing the above listed functional effects are known to those skilled in the art and are also exemplified in the Examples of the present application.

The antibody may modulate the activity of a cell expressing a T cell target, wherein said modulation is an increase or decrease in the activity of said cell. The cell is typically a T cell. The antibody may increase the activity of a CD4+ or CD8+ effector cell, or may decrease the activity of a regulatory T cell (Treg). In either case, the net effect of the antibody will be an increase in the activity of effector T cells.

Methods for determining a change in the activity of effector T cells are well known and include, for example, measuring for an increase in the level of T cell IL-2 or IFN-γ production or an increase in T cell proliferation in the presence of the antibody relative to the level of T cell IL-2 or IFN-γ production and/or T cell proliferation in the presence of a control. Assays for cell proliferation and/or IL-2 or IFN-γ production are well known and assays are also exemplified in the Examples. Additional methods of determining a change in the activity of effector T cells include measuring the change in expression of e.g. CD25, CD69, ICOS, EOMES, CD107a and/or granzyme B by the T cells, or by measuring the change in proliferation of the T cells by use of e.g. CFSE or by measuring levels of Ki67, both of which can be achieved using flow cytometry-based methods.

Methods for determining a change in the activity of Treg cells are well known and include, for example, measuring the reprogramming of Treg cells to Th cells in in vitro assays by evaluating their production of TGF-β and IFN-γ, or by measuring the Treg cell suppression capacity in in vitro assays where CD3/CD28-stimulated CD4+ T cells are co-cultured with the Treg cells and the proliferation of the CD4+ T cells is evaluated by use of CFSE or other similar proliferation dyes, or by measuring the level of Treg cell differentiation in in vitro assays where CD4+ T cells are cultured in conditions promoting polarization to inducible Treg (iTreg) cells and where the frequency of CD127low FoxP3+ iTreg cells is measured. Additional methods for determining a change in the activity of Treg cells induced by the antibody include ADCC reporter assays to determine the depletion of Treg cells or other ADCC reporter assays where Treg cells are co-cultured with NK cells or macrophages and LDH release or various viability stains are used to determine the depletion of Treg cells.

Methods for determining a change in the activity of NK cells are well known and include, for example, measuring the change in expression of e.g. CD25, CD107a, granzyme B or NKG2D by flow cytometry-based methods or in in vitro assays where the effect of the antibody on the functionality of the NK cells can be measured by the release of cytokines and lytic enzymes, e.g. IFN-γ, TNF-α or perforin.

In one embodiment of the first aspect of the invention, the bispecific antibody is capable of inducing an increase in the activity of an effector T cell, optionally wherein said increase is at least 1.5-fold, 4.5-fold or 7-fold higher than the increase in activity of an effector T cell induced by a combination of the immunoglobulin molecule and Fab fragment administered to the T cell as separate molecules. This can be tested in vitro in T cell activation assays, e.g. by measuring. IL-2 or IFN-γ production. Activation of effector T cells would imply that a tumour-specific T cell response can be achieved in vivo. Further, an anti-tumour response in an in vivo model, such as a mouse model would imply that a successful immune response towards the tumour has been achieved. Thus, this would indicate that the bispecific antibody is capable of inducing tumour immunity.

In one embodiment, the bispecific antibody induces an increase in the activation of an antigen-presenting cell, such as a B cell or dendritic cell.

It will be appreciated by persons skilled in the art, that said increase in activation may be an increase in the expression of the co-stimulatory molecules CD80 or CD86, or increased IL-12 production, or increased ability to present antigens, e.g. tumor antigens, on MHC class I or II (also by so called cross presentation, whereby an antigen taken up by internalization induced by the bispecific antibody (for example, as induced by the exemplary bispecific CD40-EPCAM antibody) ends up being presented on an MHC class I molecule) to T-cells, generating an enhanced activation of T-cells recognizing said antigen, by the antigen-presenting cell.

In one embodiment, the bispecific antibody induces an increase in the uptake of tumour debris or tumour extracellular vesicles by an antigen-presenting cell, such as a B cell or dendritic cell.

It will be appreciated by persons skilled in the art, that said increase in uptake may be measured by the co-localization or internalization of the tumour debris or tumour extracellular vesicles by the antigen-presenting cell. The increased uptake of tumour debris or tumour extracellular vesicles by the antigen-presenting cells would subsequently result in a broader T cell repertoire and, thus, more effective T cell-mediated tumour eradication. Methods for determining the expansion of tumour-antigen specific T cells are well known and include, for example, the use of MHC-peptide multimers, e.g. tetramers or pentamers. Such expansion may be measured by inoculating mice with tumours expressing a specific tumour antigen or tumours transfected with a tumour model antigen (e.g. ovalbumin), alternatively by inoculating mice with the same cells that have been heat shocked to induce necrosis, followed by measuring the expansion of tumour antigen-specific T cells by use of various MHC-tumour (model) antigen peptide tetramers or pentamers by flow cytometry-based methods.

In one embodiment, the bispecific antibody binds to the first and/or the second antigen with a $K_D$ of less than $100 \times 10^{-9}$M or less than $50 \times 10^{-9}$M or less than $25 \times 10^{-9}$M, preferably less than 10, 9, 8, 7, or $6 \times 10^{-9}$M, more preferably less than 5, 4, 3, 2, or $1 \times 10^{-9}$M, most preferably less than $9 \times 10^{-10}$ M.

Standard assays to evaluate the binding ability of ligands towards targets are well known in the art, including for example, ELISAs, Western blots, RIAs, and flow cytometry analysis. The binding kinetics (e.g., binding affinity) of the bispecific antibody can also be assessed by standard assays known in the art, such as by Surface Plasmon Resonance analysis (SPR). Such assays are also demonstrated within the Examples of the present application.

The terms "binding activity" and "binding affinity" are intended to refer to the tendency of a polypeptide molecule to bind or not to bind to a target. Binding affinity may be quantified by determining the dissociation constant (Kd) for a polypeptide and its target. A lower Kd is indicative of a higher affinity for a target. Similarly, the specificity of binding of a polypeptide to its target may be defined in terms of the comparative dissociation constants (Kd) of the polypeptide for its target as compared to the dissociation constant with respect to the polypeptide and another, non-target molecule.

The value of this dissociation constant can be determined directly by well-known methods and can be computed even for complex mixtures by methods such as those, for example, set forth in Caceci et al. (Byte 9:340-362, 1984; the disclosures of which are incorporated herein by reference). For example, the Kd may be established using a double-filter nitrocellulose filter binding assay such as that disclosed by Wong & Lohman (Proc. Natl. Acad. Sci. USA 90, 5428-5432, 1993). Other standard assays to evaluate the binding ability of ligands such as antibodies towards targets are known in the art, including for example, ELISAs, Western blots, RIAs, and flow cytometry analysis. The binding kinetics (e.g., binding affinity) of the antibody also can be assessed by standard assays known in the art, such as by Biacore™ system analysis.

A competitive binding assay can be conducted in which the binding of the antibody to the target is compared to the binding of the target by another known ligand of that target, such as another antibody. The concentration at which 50% inhibition occurs is known as the Ki. Under ideal conditions, the Ki is equivalent to Kd. The Ki value will never be less than the Kd, so measurement of Ki can conveniently be substituted to provide an upper limit for Kd.

Alternative measures of binding affinity include EC50 or IC50. In this context EC50 indicates the concentration at which a polypeptide achieves 50% of its maximum binding to a fixed quantity of target. IC50 indicates the concentration at which a polypeptide inhibits 50% of the maximum binding of a fixed quantity of competitor to a fixed quantity of target. In both cases, a lower level of EC50 or IC50 indicates a higher affinity for a target. The EC50 and IC50 values of a ligand for its target can both be determined by well-known methods, for example ELISA. Suitable assays to assess the EC50 and IC50 of polypeptides are set out in the Examples.

A bispecific antibody of the invention is preferably capable of binding to one of its targets with an affinity that is at least two-fold, 10-fold, 50-fold, 100-fold or greater than its affinity for binding to another non-target molecule.

In one embodiment, one or more amino acids are removed from the N-termini end of the light chain of (b). To put this another way, the N-termini end of the light chain of (b) is truncated by one or more amino acid.

In a further embodiment, two amino acids to nine amino acids are removed from the N-termini end of the light chain of (b), for example: three amino acids to nine amino acids; four amino acids to nine amino acids; five amino acids to nine amino acids; six amino acids to nine amino acids; seven amino acids to nine amino acids; or three amino acids to six amino acids.

In a preferred embodiment:
three amino acids are removed from the N-termini end of the light chain of (b); or six amino acids are removed from the N-termini end of the light chain of (b); or nine amino acids are removed from the N-termini end of the light chain of (b).

The inventors have surprisingly identified that truncating the N-terminal end of the light chain of a Fab fragment (i.e. (b)) in a bispecific antibody of the invention can improve the binding and/or formation of the bispecific antibody molecule.

An eleventh aspect of the invention is a polypeptide comprising an antigen binding fragment,
wherein the antigen binding fragment comprises an antibody VL region and an antibody VH region,
wherein the antigen binding fragment comprises four or more mutations to promote association of the heavy chain with the light chain,
wherein the VL region comprises a mutation at position 44 (according to IMGT numbering),
and wherein the VH region comprises a mutation at position 44 (according to IMGT numbering).

In one embodiment, the antigen binding fragment comprises four mutations to 20 mutations, for example: four mutations to 15 mutations; four mutations to 10 mutations; four mutations to nine mutations; four mutations to seven mutations; four mutations to six mutations; four mutation to five mutations, preferably four mutations to nine mutations.

In a particular embodiment, the antigen binding fragment comprises four mutations, five mutations, six mutations, seven mutations or nine mutations.

In one embodiment, the polypeptide comprises four mutations to 20 mutations, for example: four mutations to 15 mutations; four mutations to 10 mutations; four mutations to nine mutations; four mutations to seven mutations; four mutations to six mutations; four mutation to five mutations, preferably four mutations to nine mutations.

In a particular embodiment, the polypeptide comprises four mutations, five mutations, six mutations, seven mutations or nine mutations.

In one embodiment, the antigen-binding fragment is selected from the group consisting of: an Fv fragment (such as a single chain Fv fragment, or a disulphide-bonded Fv fragment), a Fab-like fragment (such as a Fab fragment; a Fab' fragment or an F(ab)$_2$ fragment) and domain antibodies.

In one embodiment, the polypeptide is an immunoglobulin molecule.

In one embodiment, the polypeptide further comprising one or more mutations are in one or more of the following regions:

(i) the CH1 region and/or (ii) the CKappa or CLambda region.

In one embodiment, the CH1 region comprises a mutation at position 168 and/or at position 170 (according to EU numbering); and wherein the CKappa or CLambda region comprises a mutation at position 135 and/or at position 176 (according to Kabat numbering).

In one embodiment, the CH1 region comprises a mutation at position H168 and/or at position F170 (according to EU numbering); and wherein the CKappa or CLambda region comprises a mutation at position L135 and/or at position S176 (according to Kabat numbering).

In one embodiment, the CH1 region comprises a mutation at position H168A and/or at position F170G (according to EU numbering); and wherein the CKappa or CLambda region comprises a mutation at position L135Y and/or at position S176W (according to Kabat numbering).

In one embodiment, the VL region comprises a mutation at position Q44 (according to IMGT numbering), the VH region comprises a mutation at position Q44 (according to IMGT numbering)

the CH1 region comprises a mutation at position H168 and/or at position F170 (according to EU numbering); and and the CKappa or CLambda region comprises a mutation at position L135 and/or at position S176 (according to Kabat numbering).

In one embodiment, the VL region comprises a mutation at position Q44E, Q44D, Q44R or Q44K (according to IMGT numbering), the VH region comprises a mutation at position Q44R, Q44K, Q44E, or Q44D (according to IMGT numbering), the CH1 region comprises a mutation at position H168A and/or at position F170G (according to EU numbering); and the CKappa or CLambda region comprises a mutation at position L135Y and/or at position S176W (according to Kabat numbering).

In one embodiment, the VL region comprises a mutation at position Q44 (according to IMGT numbering), and wherein the VH region comprises a mutation at position 44 comprises a mutation at position Q44 (according to IMGT numbering).

In one embodiment, the VL region mutation at position Q44E, Q44D, Q44R or Q44K (according to IMGT numbering), and wherein the VH region mutation at position Q44R, Q44K, Q44E, or Q44D (according to IMGT numbering).

In one embodiment, the antigen binding fragment comprises two or more mutations at positions selected from the list consisting of: 44, 49 and 120 (according to IMGT numbering).

In one embodiment, the VL region comprises one or more mutation at positions selected from the list consisting of: 44, 49 and 120 (according to IMGT numbering).

In one embodiment, the VH region comprises one or more mutation at positions selected from the list consisting of: 44, 49 and 120 (according to IMGT numbering).

In one embodiment, the two or more mutations are positions selected from the list consisting of: Q44, G49, A49, Q120 and A120 (according to IMGT numbering).

In one embodiment, the two or more mutations are positions selected from the list consisting of: Q44E, Q44R, Q44K, G49C, A49D, Q120C, A120C and Q120K (according to IMGT numbering).

In one embodiment, the mutations prevent the formation of aggregates and a Fab by-product.

In one embodiment, the mutations prevent formation of aggregates by generating steric hindrance and/or incompatibility between charges.

In one embodiment, the mutations prevent formation of a Fab by-product by generating steric hindrance and/or incompatibility between charges.

In one embodiment, the polypeptide comprises one or more mutation pairs each comprising two functionally compatible mutations.

In one embodiment, the functionally compatible mutations are selected from:

(a) cavity and protruding surface mutations (i.e. steric mutations); and/or (b) hydrophobic swap mutations; and/or (c) charged mutations (i.e. salt mutations); and/or (d) double charged mutations; and/or (e) mutations resulting in the formation of a disulphide bridge.

In one embodiment, the polypeptide comprises one or more mutation pairs in one or more of the following region groups:

(a) the CH1 and CKappa or CLambda region; and/or (b) the VL and VH regions.

In one embodiment, the mutation pairs are in the CH1 and CKappa or CLambda regions are selected from:

(a) cavity and protruding surface mutations (i.e. steric mutations); and/or (b) hydrophobic swap mutations; and/or (c) charged mutations (i.e. salt mutations); and/or (d) mutations resulting in the formation of a disulphide bridge.

In one embodiment, the mutation pairs are in the VH and VL regions, and wherein the mutation pairs are selected from:

(a) charged mutations (i.e. salt mutations); and/or (b) double charged mutations; and/or (c) mutations resulting in the formation of a disulphide bridge.

In one embodiment, the polypeptide comprises one or more mutation pairs selected from:

(a) steric mutations in the CH1 and CKappa or CLambda regions;

(b) steric mutations in the CH1 and CKappa or CLambda regions and salt mutations in the VH and VL regions;

(c) hydrophobic mutations in the CH1 and CKappa or CLambda regions;

(d) hydrophobic mutations in the CH1 and CKappa or CLambda regions and salt mutations in the VH and VL regions;

(e) salt mutations in the CH1 and CKappa or CLambda regions and salt mutations in the VH and VL regions;

In one embodiment, the mutations are at positions selected from the group consisting of:

(a) one or more of the following positions in the CH1 domain: H168, F170, L145, S183 and T187 (according to EU numbering); and/or (b) a position selected from the one or more of the following position ranges in the CKappa or CLambda domain: position 132 to 138, position 173 to 179, position 130 to 136, position 111 to 117 and position 134 to 140 (according to Kabat numbering).

In one embodiment, the mutations are at positions selected from the group consisting of:

(a) one or more of the following positions in the CH1 domain: H168, F170, L145, S183 and T187 (according to EU numbering); and/or (b) one or more of the following positions in the CKappa or CLambda domain: L135, S176, V133, S114 and N137 (according to Kabat numbering).

In one embodiment, the mutations are selected from the group consisting of:

(a) one or more of the following mutations in the CH1 domain: X168A, X170G, X145Q, X183V and X187E (according to EU numbering); and/or (b) one or more of the following mutations in the CKappa or CLambda domain: X135Y, X176W, X133T, X176V, X114A and X137K (according to Kabat numbering); wherein X is any amino acid.

In one embodiment, the mutations are selected from the group consisting of:

(a) one or more of the following mutations in the CH1 domain: H168A, F170G, L145Q, S183V and T187E (according to EU numbering); and/or (b) one or more of the following mutations in the CKappa or CLambda domain: L135Y, S176W, V133T, S176V, S114A and N137K (according to Kabat numbering).

In one embodiment, the VL region comprises a mutation at position 44 (according to IMGT numbering), the VH region comprises a mutation at position 44 (according to IMGT numbering)

the CH1 region comprises a mutation at position 145 and/or at position 183 (according to EU numbering); and and the CKappa or CLambda region comprises a mutation at position 133 and/or at position 176 (according to Kabat numbering).

In one embodiment, the VL region comprises a mutation at position Q44 (according to IMGT numbering), the VH region comprises a mutation at position Q44 (according to IMGT numbering)

the CH1 region comprises a mutation at position L145 and/or at position S183 (according to EU numbering); and and the CKappa or CLambda region comprises a mutation at position V133 and/or at position S176 (according to Kabat numbering).

In one embodiment, the VL region comprises a mutation at position X44E, X44D, X44R or X44K (according to IMGT numbering), the VH region comprises a mutation at position X44R, X44K, X44E, or X44D (according to IMGT numbering), the CH1 region comprises a mutation at position X145Q and/or at position X183V (according to EU numbering); and and the CKappa or CLambda region comprises a mutation at position X133T and/or at position X176V (according to Kabat numbering); wherein X is any amino acid.

In one embodiment, the VL region comprises a mutation at position Q44E, Q44D, Q44R or Q44K (according to IMGT numbering), the VH region comprises a mutation at position Q44R, Q44K, Q44E, or Q44D (according to IMGT numbering), the CH1 region comprises a mutation at position L145Q and/or at position S183V (according to EU numbering); and and the CKappa or CLambda region comprises a mutation at position V133T and/or at position S176V (according to Kabat numbering).

In one embodiment, the VL region comprises a mutation at position 44 and/or 49 (according to IMGT numbering), the VH region comprises a mutation at position 44 and/or 120 (according to IMGT numbering)

the CH1 region comprises a mutation at position 187 (according to EU numbering); and and the CKappa or CLambda region comprises a mutation at position 114 and/or at position 137 (according to Kabat numbering).

In one embodiment, the VL region comprises a mutation at position Q44 and/or A49 (according to IMGT numbering), the VH region comprises a mutation at position Q44 and/or Q120 (according to IMGT numbering)

the CH1 region comprises a mutation at position T187 (according to EU numbering); and and the CKappa or CLambda region comprises a mutation at position S114 and/or at position N137 (according to Kabat numbering).

In one embodiment, the VL region comprises a mutation at position X44E, X44D, X44R X44K and/or X49D (according to IMGT numbering), the VH region comprises a mutation at position X44R, X44K, X44E, X44D and/or X120K (according to IMGT numbering), the CH1 region comprises a mutation at position X187E (according to EU numbering); and and the CKappa or CLambda region comprises a mutation at position X114A and/or at position X137K (according to Kabat numbering);

wherein X is any amino acid.

In one embodiment, the VL region comprises a mutation at position Q44E, Q44D, Q44R Q44K and/or A49D (according to IMGT numbering), the VH region comprises a mutation at position Q44R, Q44K, Q44E Q44D and/or Q120K (according to IMGT numbering), the CH1 region comprises a mutation at position T187E (according to EU numbering); and and the CKappa or CLambda region comprises a mutation at position S114A and/or at position N137K (according to Kabat numbering).

In one embodiment, the VL region comprises a mutation at position 44 (according to IMGT numbering), the VH region comprises a mutation at position 44 (according to IMGT numbering)

the CH1 region comprises a mutation at position 145, at position 183 and/or at position 187 (according to EU numbering); and and the CKappa or CLambda region comprises a mutation at position 114, at position 133, at position 137 and/or at position 176 (according to Kabat numbering).

In one embodiment, the VL region comprises a mutation at position Q44 (according to IMGT numbering), the VH region comprises a mutation at position Q44 (according to IMGT numbering)

the CH1 region comprises a mutation at position L145, at position S183 and/or at position T187 (according to EU numbering); and and the CKappa or CLambda region comprises a mutation at position S114, at position V133, at position N137 and/or at position S176 (according to Kabat numbering).

In one embodiment, the VL region comprises a mutation at position X44E, X44D, X44R or X44K (according to IMGT numbering), the VH region comprises a mutation at position X44R, X44K, X44E, or X44D (according to IMGT numbering), the CH1 region comprises a mutation at position X145Q, at position X183V and/or at position X187E (according to EU numbering); and and the CKappa or CLambda region comprises a mutation at position X114A, at position X133T, at position X137K and/or at position X176V (according to Kabat numbering);

wherein X is any amino acid.

In one embodiment, the VL region comprises a mutation at position Q44E, Q44D, Q44R or Q44K (according to IMGT numbering), the VH region comprises a mutation at position Q44R, Q44K, Q44E, or Q44D (according to IMGT numbering), the CH1 region comprises a mutation at position L145Q, at position S183V and/or at position T187E (according to EU numbering); and and the CKappa or CLambda region comprises a mutation at position S114A, at position V133T, at position N137K and/or at position S176V (according to Kabat numbering).

In a further embodiment, the VH region comprises a mutation at position 65. Preferably, the VH region comprises a mutation at position T65. Most preferably, the VH region comprises a mutation at position X65A or X65E, wherein X is any amino acid (for example, X65A or X65E). Surprisingly, the inventors found that molecules with this mutation at position 65 showed improved purity after protein A purification.

In one embodiment, the polypeptide is a bispecific antibody.

In one embodiment, the polypeptide is an immunoglobulin molecule comprising at least two antigen binding fragments, with the first antigen binding fragment having specificity for the first antigen and a second antigen binding fragment having specificity for a second antigen, preferably wherein the first and second antigen binding fragment are a first Fab and a second Fab.

In one embodiment, the bispecific antibody comprises (a) an immunoglobulin molecule having specificity for a first antigen, the immunoglobulin molecule comprising a first heavy chain polypeptide and a first light chain polypeptide; and (b) at least one Fab fragment having specificity for a second antigen, the Fab fragment comprising a second heavy chain polypeptide and a second light chain polypeptide wherein the second light chain polypeptide is fused to the C-terminus of the first heavy chain polypeptide and wherein the bispecific antibody comprises one or more mutations to promote association of the first heavy chain polypeptide with the first light chain polypeptide and/or to promote association of the second heavy chain polypeptide with the second light chain polypeptide.

In further embodiments, the polypeptide of the eleventh aspect of the invention can comprise one or more features of the bispecific antibody of the first aspect of the invention, described herein. Additionally, the polypeptide can be for any use or used in any method as described herein for the bispecific antibody of the first aspect of the invention.

Polynucleotides, Vectors and Cells

The invention also relates to polynucleotides that encode all or part of a polypeptide of the invention. Thus, a polynucleotide of the invention may encode any polypeptide chain as described herein. The terms "nucleic acid molecule" and "polynucleotide" are used interchangeably herein and refer to a polymeric form of nucleotides of any length, either deoxyribonucleotides or ribonucleotides, or analogues thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or substantially isolated form. By substantially isolated, it is meant that there may be substantial, but not total, isolation of the polypeptide from any surrounding medium. The polynucleotides may be mixed with carriers or diluents which will not interfere with their intended use and still be regarded as substantially isolated.

A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

Representative polynucleotides which encode examples of a heavy chain or light chain amino acid sequence of an antibody may comprise or consist of any one of the nucleotide sequences disclosed herein, for example any one of SEQ ID NOs: 26 to 33.

```
Reference polynucleotide sequence VH (SEQ ID NO: 26):
gaagtgcagctgctggaaagcggcggcggcctggtgcagccgggcggcagcctgcgcctgagctgcgcggcga gcggctttacctttagcagctatgcgatgagctgggtgcgccaggcgccgggcaaaggcctggaatgggtgagcgc gattagcggcagcggcggcagcacctattatgcggatagcgtgaaaggccgctttaccattagccgcgataacagc aaaaacaccctgtatctgcagatgaacagcctgcgcgcggaagataccgcggtgtattattgcgcgcgctatgtgaa ctttggcatggattattggggccagggcaccctggtgaccgtgagcagc
```

-continued

Reference polynucleotide sequence VL (SEQ ID NO: 27):
gatattcagatgacccagagcccgagcagcctgagcgcgagcgtgggcgatcgcgtgaccattacctgccgcgcg agccagagcattagcagctatctgaactggtatcagcagaaaccgggcaaagcgccgaaactgctgatttatgcgg cgagcagcctgcagagcggcgtgccgagccgctttagcggcagcggcagcggcaccgattttaccctgaccatta gcagcctgcagccggaagattttgcgacctattattgccagcagagctatagcaccccgtatacctttggccagggca ccaaactggaaattaaa Reference polynucleotide sequence CH1 (SEQ ID NO: 28):
gcgagcaccaaaggcccgagcgtgtttccgctggcgccgagcagcaaaagcaccagcggcggcaccgcggcg ctgggctgcctggtgaaagattattttccggaaccggtgaccgtgagctggaacagcggcgcgctgaccagcggcg tgcatacctttccggcggtgctgcagagcagcggcctgtatagcctgagcagcgtggtgaccgtgccgagcagcag cctgggcacccagacctatatttgcaacgtgaaccataaaccgagcaacaccaaagtggataaaaaagtggaac cgaaaagctgc Reference polynucleotide sequence CKappa (SEQ ID NO: 29):
cgcaccgtggcggcgccgagcgtgtttattttttccgccgagcgatgaacagctgaaaagcggcaccgcgagcgtgg tgtgcctgctgaacaacttttatccgcgcgaagcgaaagtgcagtggaaagtggataacgcgctgcagagcggcaa cagccaggaaagcgtgaccgaacaggatagcaaagatagcacctatagcctgagcagcaccctgaccctgagc aaagcggattatgaaaaacataaagtgtatgcgtgcgaagtgacccatcagggcctgagcagcccggtgaccaaa agctttaaccgcggcgaatgc Reference polynucleotide sequence CLambda 1 (SEQ ID NO: 62):
ggccagccgaaagcgaacccgaccgtgaccctgtttccgccgagcagcgaagaactgcaggcgaacaaagcg accctggtgtgcctgattagcgatttttatccgggcgcggtgaccgtggcgtggaaagcggatggcagcccggtgaa agcgggcgtggaaaccaccaaaccgagcaaacagagcaacaacaaatatgcggcgagcagctatctgagcct gaccccggaacagtggaaaagccatcgcagctatagctgccaggtgacccatgaaggcagcaccgtggaaaaa accgtggcgccgaccgaatgcagc Reference polynucleotide sequence CLambda 2 (SEQ ID NO: 63):
ggccagccgaaagcggcgccgagcgtgaccctgtttccgccgagcagcgaagaactgcaggcgaacaaagcg accctggtgtgcctgattagcgatttttatccgggcgcggtgaccgtggcgtggaaagcggatagcagcccggtgaa agcgggcgtggaaaccaccaccccgagcaaacagagcaacaacaaatatgcggcgagcagctatctgagcctg accccggaacagtggaaaagccatcgcagctatagctgccaggtgacccatgaaggcagcaccgtggaaaaaa ccgtggcgccgaccgaatgcagc Reference polynucleotide sequence CLambda 3 (SEQ ID NO: 64):
ggccagccgaaagcggcgccgagcgtgaccctgtttccgccgagcagcgaagaactgcaggcgaacaaagcg accctggtgtgcctgattagcgatttttatccgggcgcggtgaccgtggcgtggaaagcggatagcagcccggtgaa agcgggcgtggaaaccaccaccccgagcaaacagagcaacaacaaatatgcggcgagcagctatctgagcctg accccggaacagtggaaaagccataaaagctatagctgccaggtgacccatgaaggcagcaccgtggaaaaaa ccgtggcgccgaccgaatgcagcagc CD40 binding VH (SEQ ID NO: 30):
gaagtgcagctgctggaaagcggcggcggcctggtgcagccgggcggcagcctgcgcctgagctgcgcggcga gcggctttacctttagcagctatgcgatgagctgggtgcgccaggcgccgggcaaaggcctggaatgggtgagcgg cattggcagctatggcggcggcacctattatgcggatagcgtgaaaggccgctttaccattagccgcgataacagca aaaacaccctgtatctgcagatgaacagcctgcgcgcggaagataccgcggtgtattattgcgcgcgctatgtgaac tttggcatggattattggggccagggcaccctggtgaccgtgagcagc -continued CD40 binding VL (SEQ ID NO: 31):
gatattcagatgacccagagcccgagcagcctgagcgcgagcgtgggcgatcgcgtgaccattacctgccgcgcg agccagagcattagcagctatctgaactggtatcagcagaaaccgggcaaagcgccgaaactgctgatttatgcgg cgagcagcctgcagagcggcgtgccgagccgcttttagcggcagcggcagcggcaccgattttaccctgaccatta gcagcctgcagccggaagattttgcgacctattattgccagcagtatggccgcaacccgccgacctttggccagggc accaaactggaaattaaa EpCAM binding VH (SEQ ID NO: 32):
gaagtgcagctgctggaacagagcggcgcgggaactggtgcgcccgggcaccagcgtgaaaattagctgcaaag cgagcggctatgcgtttaccaactattggctgggctgggtgaaacagcgcccgggccatggcctggaatggattggc gatattttccgggcagcggcaacattcattataacgaaaaatttaaaggcaaagcgaccctgaccgcggataaaag cagcagcaccgcgtatatgcagctgagcagcctgacctttgaagatagcgcggtgtattttgcgcgcgcctgcgcaa ctgggatgaaccgatggattattggggccagggcaccaccgtgaccgtgagcagc EpCAM binding VL (SEQ ID NO: 33):
gaactggtgatgacccagagcccgagcagcctgaccgtgaccgcgggcgaaaaagtgaccatgagctgcaaaa gcagccagagcctgctgaacagcggcaaccagaaaaactatctgacctggtatcagcagaaaccgggccagcc gccgaaactgctgatttattgggcgagcacccgcgaaagcggcgtgccggatcgctttaccggcagcggcagcgg caccgattttaccctgaccattagcagcgtgcaggcggaagatctggcggtgtattattgccagaacgattatagctat ccgctgacctttggcgcgggcaccaaactggaaattaaa CD137 binding VH1 (SEQ ID NO: 65):
gaggtgcagctgttggagagcggggggaggcttggtacagcctggggggtccctgcgcctctcctgtgcagccagcg gattcacctttttcttacggttctatgtactgggtccgccaggctccagggaaggggctg-
gagtgggtctcatctatttcttct ggttctggttctacatactatgcagactccgtgaagggccggttcaccatctcccgtgacaattccaagaacacgctgt atctgcaaatgaacagcctgcgtgccgaggacacggctgtatattat-
tgtgcgcgctcttcttactacggttcttactactc tattgactattggggccagggaaccctggtcaccgtctcctca CD1137 binding VL1 (SEQ ID NO: 66):
gacatccagatgacccagtctccatcctccctgagcgcatctgtaggagaccgcgtcaccatcacttgccgggcaag tcagagcattagcagctatttaaattggtatcagcagaaaccagggaaagcccctaagctcctgatctatgctgcatc cagtttgcaaagtggggtcccatcacgtttcagtggcagtggaagcgggacagatttcactctcaccatcagcagtct gcaacctgaagattttgcaacttattactgtcaacagtactacgacaacctgcccactttttggccagggggaccaagctg gagatcaaa 5T4 binding VH (SEQ ID NO: 67):
gaggtgcagctgctcgagagcggggggaggcttggtacagcctggggggtccctgcgcctctcctgtgcagccagcg gattcacctttagcagctatgccatgagctgggtccgccaggctccagggaaggggctggagtgggtctcagctatta gtggtagtggtggtagcacatactatgcagactccgtgaagggccggttcaccatctcccgtgacaattccaagaac acgctgtatctgcaaatgaacagcctgcgtgccgaggacacggctgtatattattgtgcgcgctactacggtggttact actctgcttggatggactattggggccagggaaccctggtcaccgtctcctcag 5T4 binding VL (SEQ ID NO: 68):
gacatccagatgacccagtctccatcctccctgagcgcatctgtaggagaccgcgtcaccatcacttgccgggcaag tcagagcattagcagctatttaaattggtatcagcagaaaccagggaaagcccctaagctcctgatctatgctgcatc cagtttgcaaagtggggtcccatcacgtttcagtggcagtggaagcgggacagatttcactctcaccatcagcagtct gcaacctgaagattttgcaacttattactgtcaacagacttacggttacctgcacactttttggccagggggaccaagctg gagatcaaa -continued

```
OX40 binding VH (SEQ ID NO: 69):
gaggtgcagctgttggagagcggggggaggcttggtacagcctggggggtccctgcgcctctcctgtgcagccagcg gattcacctttggtggttactacatgtcttgggtccgccaggctccagggaaggggctggagtgggtctcatacattcct ggttctggtggttctacatactatgcagactccgtgaagggccggttcaccatctcccgtgacaattccaagaacacgc tgtatctgcaaatgaacagcctgcgtgccgaggacacggctgtatattattgtgcgcgctacgactactactggatgga ctattggggccagggaaccctggtcaccgtctcctca OX40 binding VL (SEQ ID NO: 70):
gacatccagatgacccagtctccatcctccctgagcgcatctgtaggagaccgcgtcaccatcacttgccgggcaag tcagagcattagcagctatttaaaattggtatcagcagaaaccagggaaagcccctaagctcctgatctatgctgcatc cagtttgcaaagtggggtcccatcacgtttcagtggcagtggaaggggacagatttcactctcaccatcagcagtct gcaacctgaagattttgcaacttattactgtcaacagggtcatggttcttacccgcacacttttggccaggggaccaagc tggagatcaaa CD137 binding VH2 (SEQ ID NO: 71):
gaggtgcagctgttggagagcggggggaggcttggtacagcctggggggtccctgcgcctctcctgtgcagccagcg gattcaccttttcttcttactacatgggttgggtccgccaggctccagggaaggggctggagtgggtctcaggtattggtt cttactacggttacacaggttatgcagactccgtgaagggccggttcaccatctcccgtgacaattccaagaacacgc tgtatctgcaaatgaacagcctgcgtgccgaggacacggctgtatattattgtgcgcgcgcttactacgactacaacta ctactacgcttactttgactattggggccagggaaccctggtcaccgtctcctca CD137 binding VL2 (SEQ ID NO: 72):
gacatccagatgacccagtctccatcctccctgagcgcatctgtaggagaccgcgtcaccatcacttgccgggcaag tcagagcattagcagctatttaaaattggtatcagcagaaaccagggaaagcccctaagctcctgatctatgctgcatc cagtttgcaaagtggggtcccatcacgtttcagtggcagtggaagcgggacagatttcactctcaccatcagcagtct gcaacctgaagattttgcaacttattactgtcaacagtctgttccgcactacccgttcacttttggccaggggaccaagct ggagatcaaa
```

A suitable polynucleotide sequence may alternatively be a variant of one of these specific polynucleotide sequences. For example, a variant may be a substitution, deletion or addition variant of any of the above nucleic acid sequences. A variant polynucleotide may comprise 1, 2, 3, 4, 5, up to 10, up to 20, up to 30, up to 40, up to 50, up to 75 or more nucleic acid substitutions and/or deletions from the sequences given in the sequence listing.

Suitable variants may be at least 70% homologous to a polynucleotide of any one of nucleic acid sequences disclosed herein, preferably at least 80 or 90% and more preferably at least 95%, 97% or 99% homologous thereto. Preferably homology and identity at these levels is present at least with respect to the coding regions of the polynucleotides. Methods of measuring homology are well known in the art and it will be understood by those of skill in the art that in the present context, homology is calculated on the basis of nucleic acid identity. Such homology may exist over a region of at least 15, preferably at least 30, for instance at least 40, 60, 100, 200 or more contiguous nucleotides. Such homology may exist over the entire length of the unmodified polynucleotide sequence.

Methods of measuring polynucleotide homology or identity are known in the art. For example, the UWGCG Package provides the BESTFIT program which can be used to calculate homology (e.g. used on its default settings) (Devereux et al, 1984, *Nucleic Acids Research* 12:387-395; the disclosures of which are incorporated herein by reference).

The PILEUP and BLAST algorithms can also be used to calculate homology or line up sequences (typically on their default settings), for example as described in Altschul, 1993, *J Mol Evol* 36:290-300; Altschul et al, 1990, *J Mol Biol* 215:403-10, the disclosures of which are incorporated herein by reference).

Software for performing BLAST analysis is publicly available through the National Centre for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff& Henikoff, 1992, *Proc. Natl. Acad. Sci. USA* 89:10915-10919; the disclosures of which are incorporated herein by reference) alignments (B) of 50, expectation (E) of 10, M=5, N=4, and a comparison of both strands.

The BLAST algorithm performs a statistical analysis of the similarity between two sequences; see e.g. Karlin & Altschul, 1993, *Proc. Natl. Acad. Sci. USA* 90:5873-5787; the disclosures of which are incorporated herein by reference. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologue may differ from a sequence in the relevant polynucleotide by less than 3, 5, 10, 15, 20 or more mutations (each of which may be a substitution, deletion or insertion). These mutations may be measured over a region of at least 30, for instance at least 40, 60 or 100 or more contiguous nucleotides of the homologue.

In one embodiment, a variant sequence may vary from the specific sequences given in the sequence listing by virtue of the redundancy in the genetic code. The DNA code has 4 primary nucleic acid residues (A, T, C and G) and uses these to "spell" three letter codons which represent the amino acids the proteins encoded in an organism's genes. The linear sequence of codons along the DNA molecule is translated into the linear sequence of amino acids in the protein(s) encoded by those genes. The code is highly degenerate, with 61 codons coding for the 20 natural amino acids and 3 codons representing "stop" signals. Thus, most amino acids are coded for by more than one codon—in fact several are coded for by four or more different codons. A variant polynucleotide of the invention may therefore encode the same polypeptide sequence as another polynucleotide of the invention, but may have a different nucleic acid sequence due to the use of different codons to encode the same amino acids.

A polypeptide of the invention may thus be produced from or delivered in the form of a polynucleotide which encodes and is capable of expressing it.

Polynucleotides of the invention can be synthesised according to methods well known in the art, as described by way of example in Green & Sambrook (2012, Molecular Cloning—a laboratory manual, 4$^{th}$ edition; Cold Spring Harbor Press; the disclosures of which are incorporated herein by reference).

The nucleic acid molecules of the present invention may be provided in the form of an expression cassette which includes control sequences operably linked to the inserted sequence, thus allowing for expression of the polypeptide of the invention in vivo. These expression cassettes, in turn, are typically provided within vectors (e.g., plasmids or recombinant viral vectors). Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a polypeptide of the invention.

The present invention thus includes expression vectors that comprise such polynucleotide sequences. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art (see Green & Sambrook, supra).

The invention also includes cells that have been modified to express a bispecific antibody or component polypeptide of the invention. Such cells include transient, or preferably stable higher eukaryotic cell lines, such as mammalian cells or insect cells, lower eukaryotic cells, such as yeast or prokaryotic cells such as bacterial cells. Particular examples of cells which may be modified by insertion of vectors or expression cassettes encoding for a polypeptide of the invention include mammalian HEK293T, CHO, HeLa, NS0 and COS cells. Preferably the cell line selected will be one which is not only stable, but also allows for mature glycosylation and cell surface expression of a polypeptide.

Such cell lines of the invention may be cultured using routine methods to produce a polypeptide of the invention, or may be used therapeutically or prophylactically to deliver antibodies of the invention to a subject. Alternatively, polynucleotides, expression cassettes or vectors of the invention may be administered to a cell from a subject ex vivo and the cell then returned to the body of the subject.

Pharmaceutical Formulations, Therapeutic Uses and Patient Groups

In another aspect, the present invention provides compositions comprising molecules of the invention, such as the bispecific antibodies, polypeptides, polynucleotides, vectors and cells described herein. For example, the invention provides a composition comprising one or more molecules of the invention, such as one or more bispecific antibodies of the invention, and at least one pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for parenteral, e.g. intravenous, intramuscular or subcutaneous administration (e.g., by injection or infusion). Depending on the route of administration, the polypeptide may be coated in a material to protect the polypeptide from the action of acids and other natural conditions that may inactivate or denature the polypeptide.

Preferred pharmaceutically acceptable carriers comprise aqueous carriers or diluents. Examples of suitable aqueous carriers that may be employed in the compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. In many cases, it will be preferable to include isotonic agents, for example, sugars, polyalcohols such as mannitol, sorbitol, or sodium chloride in the composition.

A composition of the invention also may include a pharmaceutically acceptable anti-oxidant. These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminium monostearate and gelatin.

Therapeutic compositions typically must be sterile and stable under the conditions of manufacture and storage. The composition can be formulated as a solution, microemulsion, liposome, or other ordered structure suitable to high drug concentration.

Sterile injectable solutions can be prepared by incorporating the active agent (e.g. polypeptide) in the required amount in an appropriate solvent with one or a combination of ingredients enumerated above, as required, followed by sterilization microfiltration. Generally, dispersions are prepared by incorporating the active agent into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active agent plus any additional desired ingredient from a previously sterile-filtered solution thereof.

Particularly preferred compositions are formulated for systemic administration or for local administration. Local administration may be at the site of a tumour or into a tumour-draining lymph node. The composition may preferably be formulated for sustained release over a period of time. Thus, the composition may be provided in or as part of a matrix facilitating sustained release. Preferred sustained release matrices may comprise a montanide or γ-polyglutamic acid (PGA) nanoparticles. Localised release of a polypeptide of the invention, optionally over a sustained period of time, may reduce potential autoimmune side-effects associated with administration of a CTLA-4 antagonist.

Compositions of the invention may comprise additional active ingredients as well as a bispecific antibody of the invention or component polypeptide. As mentioned above, compositions of the invention may comprise one or more bispecific antibodies of the invention. They may also comprise additional therapeutic or prophylactic agents.

Also within the scope of the present invention are kits comprising bispecific antibodies or other compositions of the invention and instructions for use. The kit may further contain one or more additional reagents, such as an additional therapeutic or prophylactic agent as discussed above.

The bispecific antibodies in accordance with the present invention may be used in therapy or prophylaxis. In therapeutic applications, polypeptides or compositions are administered to a subject already suffering from a disorder or condition, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as "therapeutically effective amount". In prophylactic applications, polypeptides or compositions are administered to a subject not yet exhibiting symptoms of a disorder or condition, in an amount sufficient to prevent or delay the development of symptoms. Such an amount is defined as a "prophylactically effective amount". The subject may have been identified as being at risk of developing the disease or condition by any suitable means.

In particular, bispecific antibodies of the invention may be useful in the treatment or prevention of cancer. Accordingly, the invention provides a bispecific antibody of the invention for use in the treatment or prevention of cancer. The invention also provides a method of treating or preventing cancer comprising administering to an individual a bispecific antibody of the invention. The invention also provides a bispecific antibody of the invention for use in the manufacture of a medicament for the treatment or prevention of cancer.

The cancer may be prostate cancer, breast cancer, colorectal cancer, pancreatic cancer, ovarian cancer, lung cancer, cervical cancer, rhabdomyosarcoma, neuroblastoma, multiple myeloma, leukemia, acute lymphoblastic leukemia, melanoma, bladder cancer, gastric cancer, head and neck cancer, liver cancer, skin cancer, lymphoma or glioblastoma.

A bispecific antibody of the present invention, or a composition comprising said antibody, may be administered via one or more routes of administration using one or more of a variety of methods known in the art. As will be appreciated by the skilled artisan, the route and/or mode of administration will vary depending upon the desired results. Systemic administration or local administration are preferred. Local administration may be at the site of a tumour or into a tumour-draining lymph node. Preferred modes of administration for bispecific antibodies or compositions of the invention include intravenous, intramuscular, intradermal, intraperitoneal, subcutaneous, spinal or other parenteral modes of administration, for example by injection or infusion. The phrase "parenteral administration" as used herein means modes of administration other than enteral and topical administration, usually by injection. Alternatively, a bispecific antibody or composition of the invention can be administered via a non-parenteral mode, such as a topical, epidermal or mucosal mode of administration.

A suitable dosage of a bispecific antibody of the invention may be determined by a skilled medical practitioner. Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular polypeptide employed, the route of administration, the time of administration, the rate of excretion of the polypeptide, the duration of the treatment, other drugs, compounds and/or materials used in combination with the particular compositions employed, the age, sex, weight, condition, general health and prior medical history of the patient being treated, and like factors well known in the medical arts.

A suitable dose of a bispecific antibody or composition of the invention may be, for example, in the range of from about 0.1 µg/kg to about 100 mg/kg body weight of the patient to be treated. For example, a suitable dosage may be from about 1 µg/kg to about 10 mg/kg body weight per day or from about 10 g/kg to about 5 mg/kg body weight per day.

Dosage regimens may be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Antibodies or compositions may be administered in a single dose or in multiple doses. The multiple doses may be administered via the same or different routes and to the same or different locations. Alternatively, antibodies or compositions can be administered as a sustained release formulation as described above, in which case less frequent administration is required. Dosage and frequency may vary depending on the half-life of the polypeptide in the patient and the duration of treatment that is desired. The dosage and frequency of administration can also vary depending on whether the treatment is prophylactic or therapeutic. In prophylactic applications, a relatively low dosage may be administered at relatively infrequent intervals over a long period of time. In therapeutic applications, a relatively high dosage may be administered, for example until the patient shows partial or complete amelioration of symptoms of disease.

Combined administration of two or more agents may be achieved in a number of different ways. In one embodiment, the bispecific antibody and the other agent may be administered together in a single composition. In another embodiment, the bispecific antibody and the other agent may be administered in separate compositions as part of a combined therapy. For example, the modulator may be administered before, after or concurrently with the other agent.

A bispecific antibody or composition of the invention may also be used in a method of increasing the activation of a population of cells expressing the first and second antigen, the method comprising administering to said population of cells a bispecific antibody or composition of the invention under conditions suitable to permit interaction between said cell and a bispecific antibody of the invention. The population of cells typically comprises at least some cells which express the first antigen, and at least some cells which express the second antigen. The method is typically carried out ex vivo.

Related Aspects of the Invention

A second aspect of the invention is a polynucleotide encoding a bispecific antibody of the first aspect of the invention or a polypeptide of the eleventh aspect of the invention, or at least one polypeptide thereof, as described above. In one embodiment, the nucleic acid molecule is a cDNA molecule. Optionally, the nucleic acid may encode an antibody heavy chain or variable region thereof, or an antibody light chain or variable region thereof.

A third aspect of the invention is a vector comprising a nucleic acid molecule according to the second aspect of the invention. Optionally, the vector may be an expression vector.

A fourth aspect of the invention provides a recombinant host cell comprising a nucleic acid according to the second or a vector according to the third aspect of the invention. It will be appreciated by persons skilled in the art that the host cell may be a bacterial cell or a mammalian cell, optionally a human cell.

A fifth aspect of the invention provides a method for producing a bispecific antibody of the first aspect of the invention or a polypeptide of the eleventh aspect of the invention, the method comprising culturing a host cell according to the fourth aspect of the invention, under conditions which permit expression of the bispecific antibody or component polypeptide chain thereof.

A sixth aspect of the invention is a composition comprising a bispecific antibody according to the first aspect of the invention or a polypeptide according to the eleventh aspect of the invention and at least one pharmaceutically acceptable diluent, carrier or excipient.

The pharmaceutical compositions will be administered to a patient in a pharmaceutically effective dose. A 'therapeutically effective amount', or 'effective amount', or 'therapeutically effective', as used herein, refers to that amount which provides a therapeutic effect for a given condition and administration regimen. This is a predetermined quantity of active material calculated to produce a desired therapeutic effect in association with the required additive and diluent, i.e. a carrier or administration vehicle. Further, it is intended to mean an amount sufficient to reduce and most preferably prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art. The administration of the pharmaceutically effective dose can be carried out both by single administration in the form of an individual dose unit or else several smaller dose units and also by multiple administrations of subdivided doses at specific intervals. Alternatively, the dose may be provided as a continuous infusion over a prolonged period.

Particularly preferred compositions are formulated for systemic administration.

The composition may preferably be formulated for sustained release over a period of time. Thus, the composition may be provided in or as part of a matrix facilitating sustained release. Preferred sustained release matrices may comprise a montanide or γ-polyglutamic acid (PGA) nanoparticles.

In one embodiment, the composition is adapted for parenteral delivery, optionally the composition is adapted for intravenous delivery.

The antibody polypeptides can be formulated at various concentrations, depending on the efficacy/toxicity of the polypeptide being used. For example, the formulation may comprise the active antibody polypeptide at a concentration of between 0.1 µM and 1 mM, more preferably between 1 µM and 500 µM, between 500 µM and 1 mM, between 300 µM and 700 µM, between 1 µM and 100 µM, between 100 µM and 200 µM, between 200 µM and 300 µM, between 300 µM and 400 µM, between 400 µM and 500 µM, between 500 µM and 600 µM, between 600 µM and 700 µM, between 800 µM and 900 µM or between 900 µM and 1 mM. Typically, the formulation comprises the active antibody polypeptide at a concentration of between 300 µM and 700 µM.

Typically, the therapeutic dose of the antibody polypeptide (with or without a therapeutic moiety) in a human patient will be in the range of 100 µg to 700 mg per administration (based on a body weight of 70 kg). For example, the maximum therapeutic dose may be in the range of 0.1 to 10 mg/kg per administration, e.g. between 0.1 and 5 mg/kg or between 1 and 5 mg/kg or between 0.1 and 2 mg/kg. It will be appreciated that such a dose may be administered at different intervals, as determined by the oncologist/physician; for example, a dose may be administered daily, twice-weekly, weekly, bi-weekly or monthly.

A seventh aspect of the invention comprises a bispecific antibody according to the first aspect of the invention or a polypeptide according to the eleventh aspect of the invention for use in a method for treating or preventing a disease or condition in an individual, as described above.

An eighth aspect of the invention is the use of a bispecific antibody according to the first aspect of the invention or a polypeptide according to the eleventh aspect of the invention in the manufacture of a medicament.

A ninth aspect of the invention is a method of treating or preventing a disease or condition in an individual, the method comprising administering to an individual a bispecific antibody according to the first aspect of the invention or a polypeptide according to the eleventh aspect of the invention, as described above.

One embodiment of the invention is a bispecific antibody according to the seventh aspect of the invention or a method according to ninth aspect of the invention wherein the disease or condition is a neoplastic disorder and optionally wherein the individual is human, or the use according to the eighth aspect of the invention wherein the medicament is for the treatment is a neoplastic disorder, optionally wherein the individual is human.

Optionally the neoplastic disorder is associated with the formation of solid tumours within the subject's body, and as a further embodiment the solid tumour is selected from prostate cancer, breast cancer, lung cancer, colorectal cancer, melanomas, bladder cancer, brain/CNS cancer, cervical cancer, oesophageal cancer, gastric cancer, head/neck cancer, kidney cancer, liver cancer, lymphomas, ovarian cancer, pancreatic cancer and sarcomas.

In one embodiment, the solid tumour is selected from the groups consisting of renal cell carcinoma, colorectal cancer, lung cancer, prostate cancer and breast cancer.

In a further embodiment, the method comprises administering the bispecific antibody systemically or locally, such as at the site of a tumour or into a tumour-draining lymph node, as described above.

In one embodiment, the bispecific antibody is for use in combination with one or more additional therapeutic agents or the method comprises administration of one or more additional therapeutic agents. It will also be appreciated by persons skilled in the art that the pharmaceutical compositions of the invention may be administered alone or in combination with other therapeutic agents used in the treatment of cancers.

Exemplary additional therapeutic agents include antimetabolites, alkylating agents, anthracyclines and other cytotoxic antibiotics, vinca alkyloids, etoposide, platinum compounds, taxanes, topoisomerase I inhibitors, other cytostatic drugs, antiproliferative immunosuppressants, corticosteroids, sex hormones and hormone antagonists, and other therapeutic antibodies (such as antibodies against a tumour-associated antigen or an immune checkpoint modulator).

For example, the additional therapeutic agent may be an immunotherapeutic agent that binds a target selected from the group consisting of PD-1/PD-L1, CD137, CD40, GITR, LAG3, TIM3, CD27, VISTA, OX40 and KIR.

Thus, the invention encompasses combination therapies comprising a bispecific polypeptide of the invention together with a further immunotherapeutic agent, effective in the treatment of cancer, which specifically binds to an immune checkpoint molecule. It will be appreciated that the therapeutic benefit of the further immunotherapeutic agent may be mediated by attenuating the function of an inhibitory immune checkpoint molecule and/or by activating the function of a stimulatory immune checkpoint or co-stimulatory molecule. In one embodiment, the further immunotherapeutic agent is selected from the group consisting of:

(a) an immunotherapeutic agent that inhibits the function of PD-1 and/or PD-1;

(b) an immunotherapeutic agent that activates the function of CD137; and (c) an immunotherapeutic agent that activates the function of CD40.

Thus, the further immunotherapeutic agent may be a PD-1 inhibitor, such as an anti-PD-1 antibody, or antigen-binding fragment thereof capable of inhibiting PD-1 function (for example, Nivolumab, Pembrolizumab, Lambrolizumab, PDR-001, MEDI-0680 and AMP-224). Alternatively, the PD-1 inhibitor may comprise or consist of an anti-PD-L1 antibody, or antigen-binding fragment thereof capable of inhibiting PD-1 function (for example, Durvalumab, Atezolizumab, Avelumab and MDX-1105).

In a further embodiment, the further immunotherapeutic agent activates CD137, such as an agonistic anti-CD137 antibody or antigen-binding portion thereof.

In a further embodiment, the further immunotherapeutic agent activates CD40, such as an agonistic anti-CD40 antibody or antigen-binding portion thereof.

It will be appreciated by persons skilled in the art that the presence of the two active agents (as detailed above) may provide a synergistic benefit in the treatment of a tumour in a subject. By "synergistic" we include that the therapeutic effect of the two agents in combination (e.g. as determined by reference to the rate of growth or the size of the tumour) is greater than the additive therapeutic effect of the two agents administered on their own. Such synergism can be identified by testing the active agents, alone and in combination, in a relevant cell line model of the solid tumour.

In one embodiment of the invention, a bispecific antibody according to the first aspect of the embodiment is conjugated to an additional therapeutic moiety.

Also within the scope of the present invention are kits comprising bispecific antibodies or other compositions of the invention and instructions for use. The kit may further contain one or more additional reagents, such as an additional therapeutic or prophylactic agent as discussed above.

A tenth aspect of the invention provides a method of producing a bispecific antibody according to the first aspect of the invention, wherein the method comprises expressing three polypeptide chains in the same host cell, wherein the three polypeptide chains are:

(a) an immunoglobulin heavy chain (the first heavy chain) fused via a polypeptide linker to a second light chain;

(b) a first light chain; and (c) a second heavy chain

In one embodiment of the tenth aspect of the invention, the method further comprises the step of modifying the ratios of the chains (a), (b) and (c) to optimise formation of a bispecific antibody.

Preferred, non-limiting examples which embody certain aspects of the invention will now be described, with reference to the following figures:

FIG. 1 shows the composition of the IgG-Fab bispecific antibody constructs. The bispecific antibodies are made up of three types of polypeptide chains: (1) IgG heavy chains (white) fused to Fab light chains (chequered) via a polypeptide linker. (2) IgG light chains (bricked) and (3) Fab heavy chains (black). Mutations are introduced in the interface between heavy and light chains.

Figure 2:
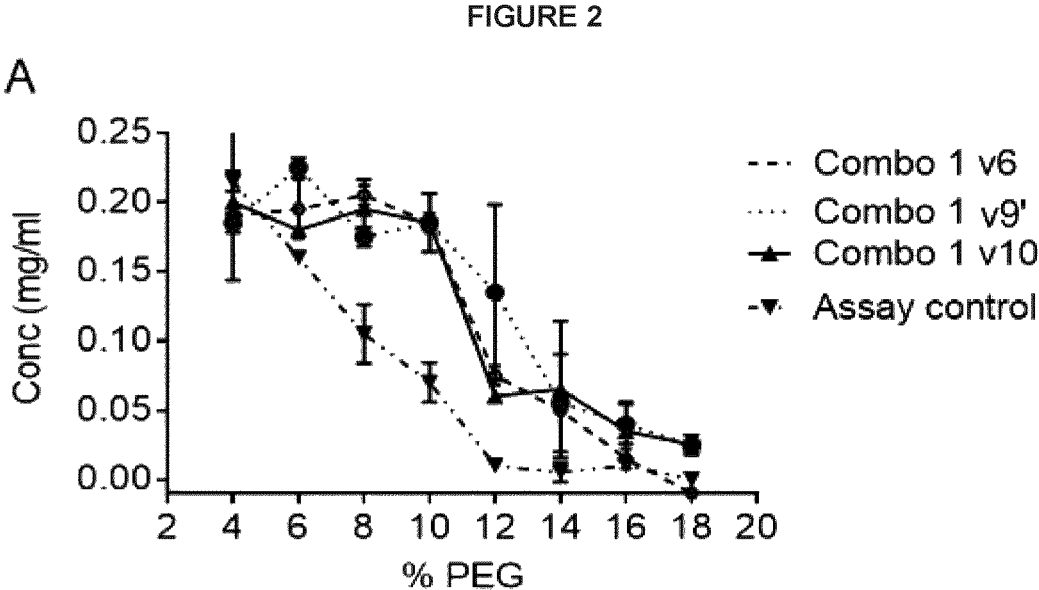
Figure 2:
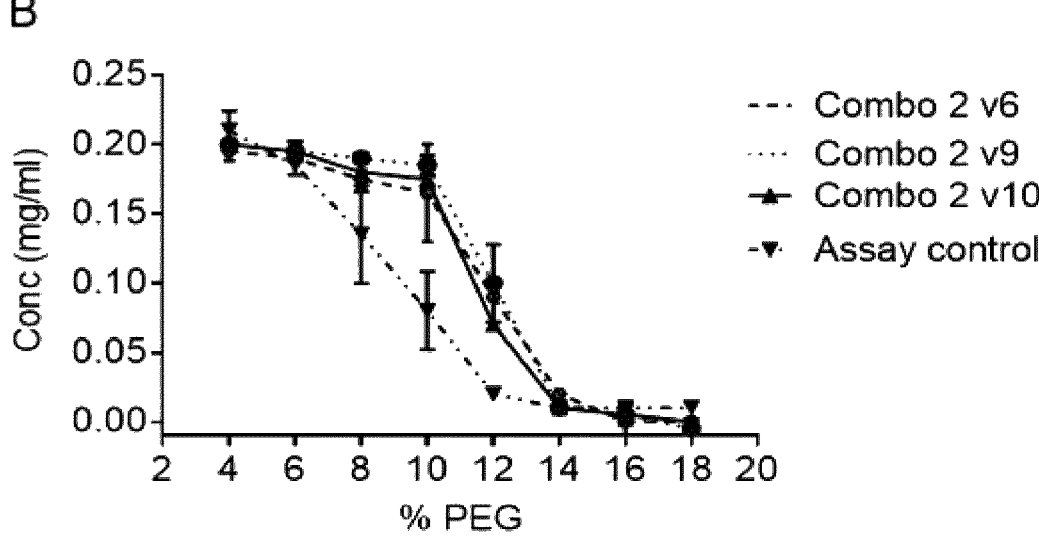
Figure 2:
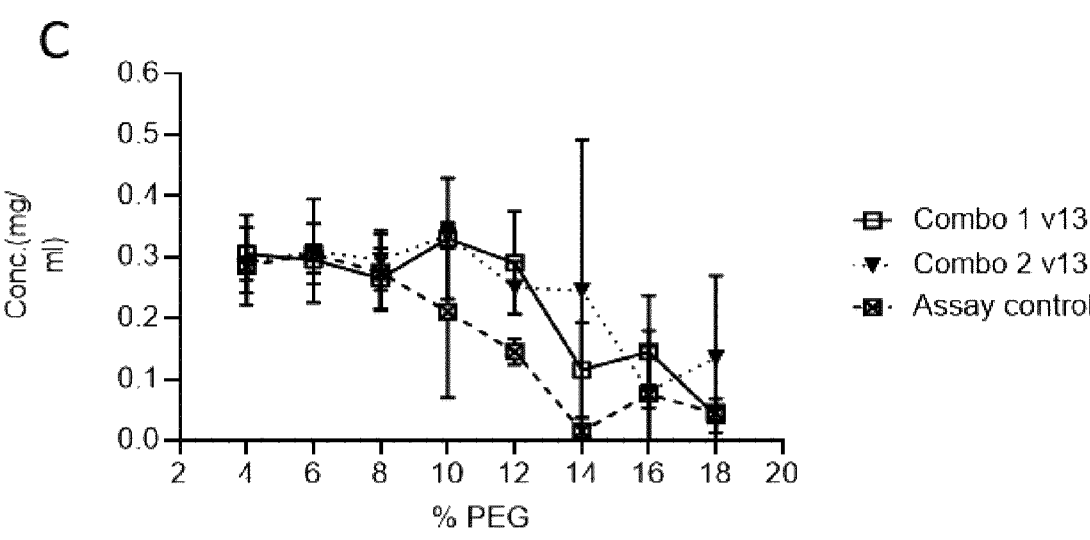
Figure 2:
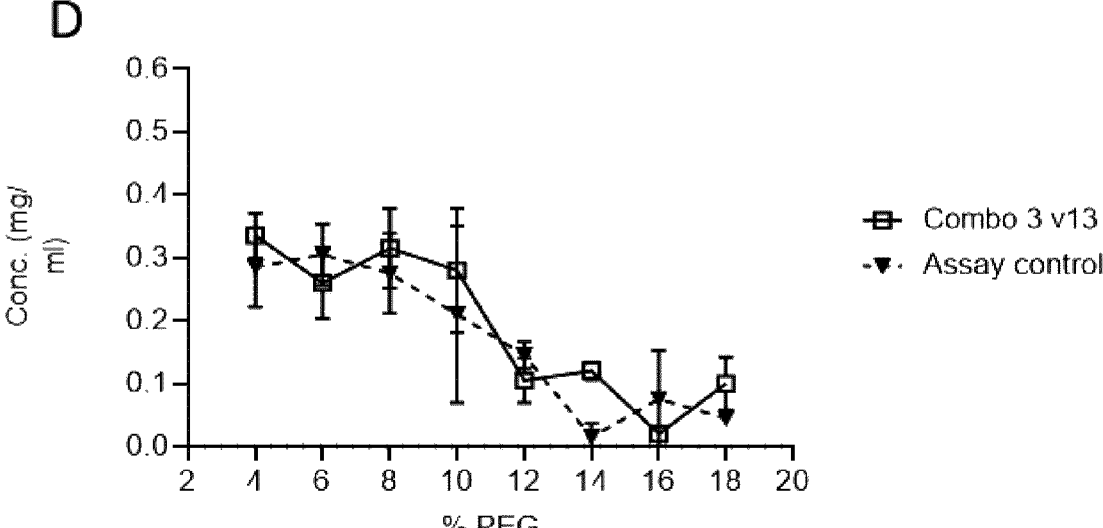

FIG. 2 shows precipitation curves of samples, A) Combo 1 variants 6, 9' and 10, B) Combo 2 variants 6, 9 and 10, C) Combo 1 and 2 variant 13, D) Combo 3 variant 13, incubated with PEG at different concentrations to test ability to self-interact and precipitate. At PEG concentrations of 9% or more protein loss <50% is observed for novel IgG-Fab bsAb regardless of mutational variant tested indicating good colloidal stability for these novel constructs.

Figure 3:
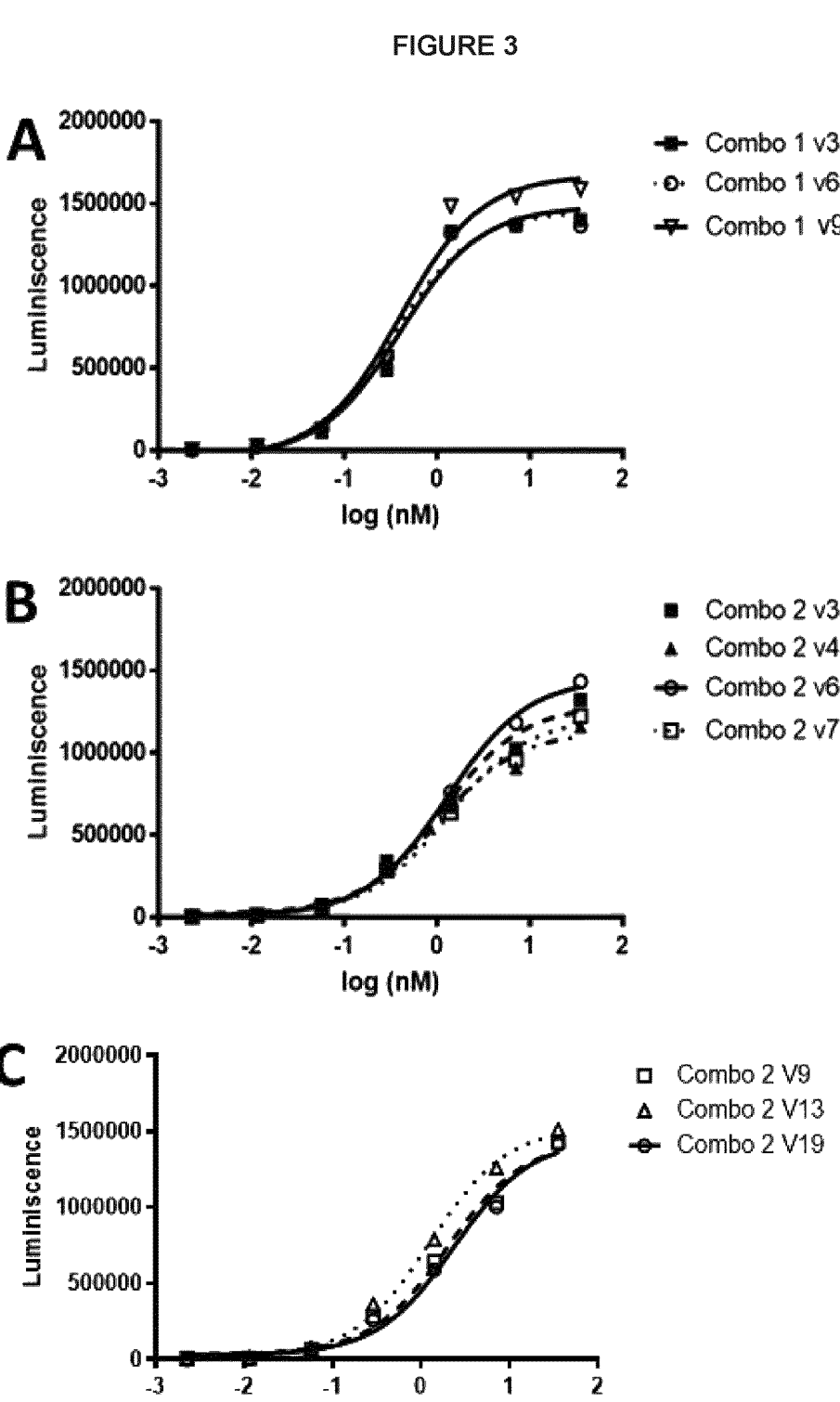
Figure 3:
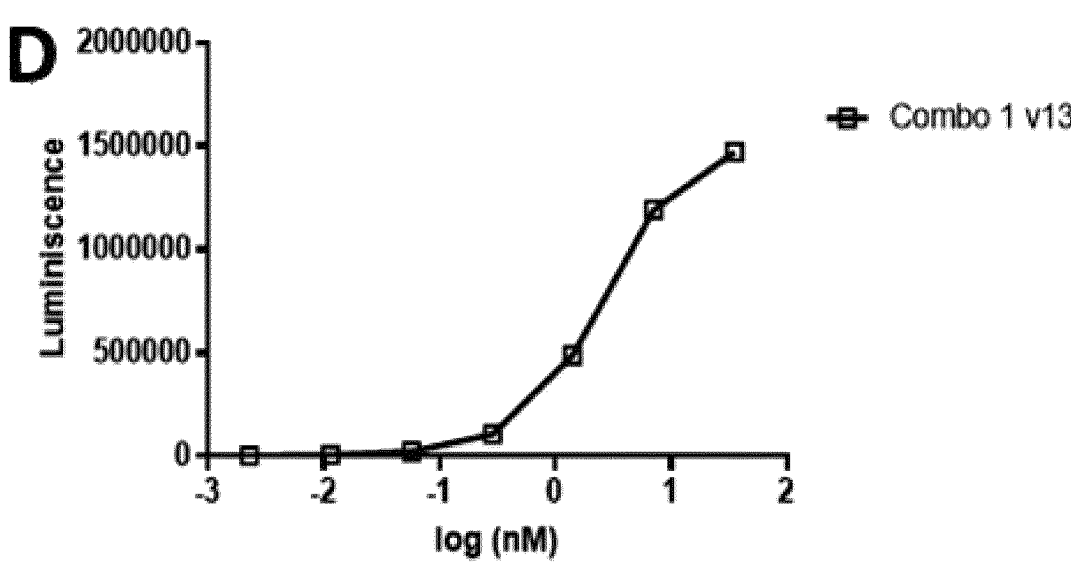
Figure 3:
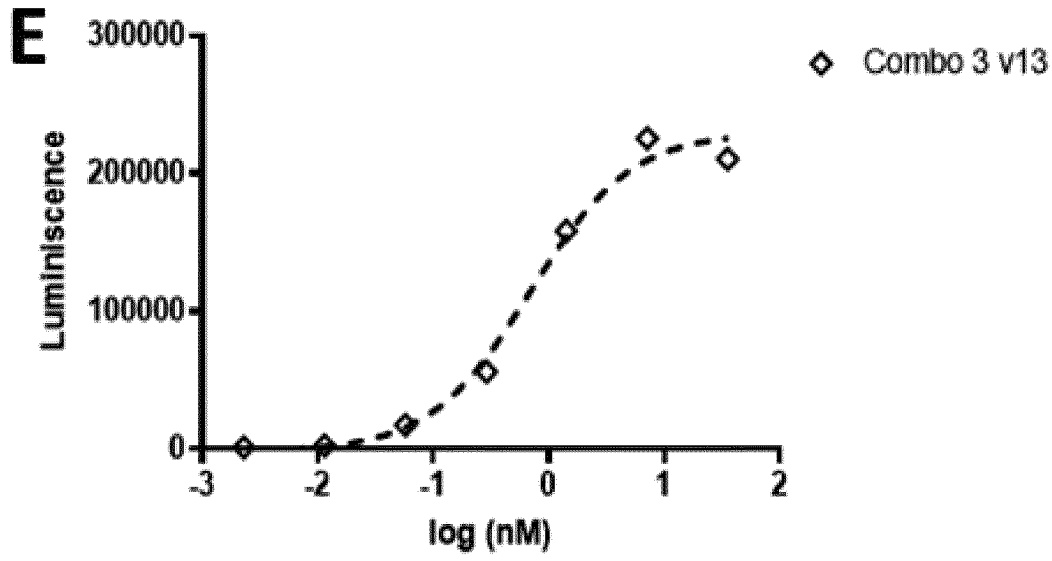

FIG. 3. Representative dual ELISA binding curves for Combo 1 constructs (CD137-5T4 bispecific) variants 3, 6, 9' (panel A) and 13 (panel D) or Combo 2 constructs (CD40-EpCAM bispecific) variants 3, 4, 6, 7, (panel B), 9, 13 and 19 (panel C) or Combo 3 construct (OX40-CD137 variant 13 (panel E).

Figure 4:
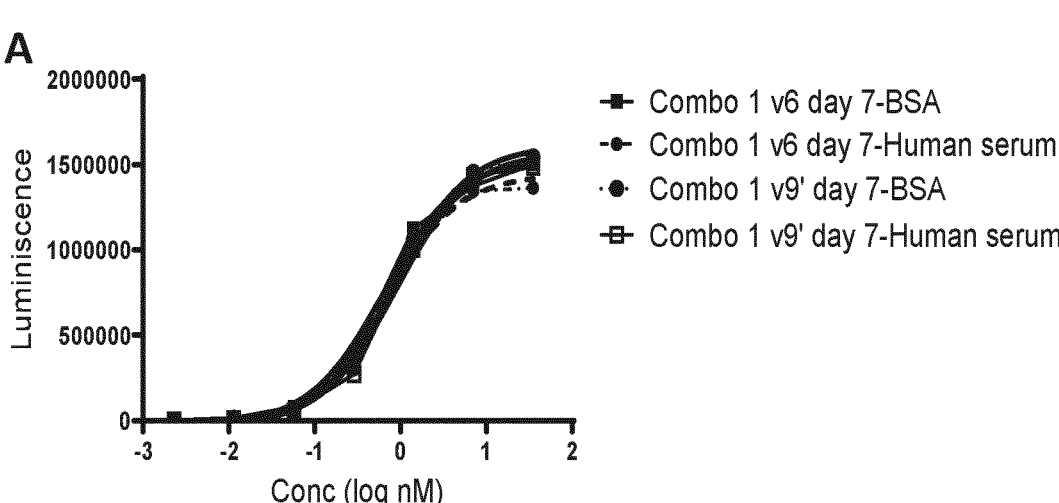
Figure 4:
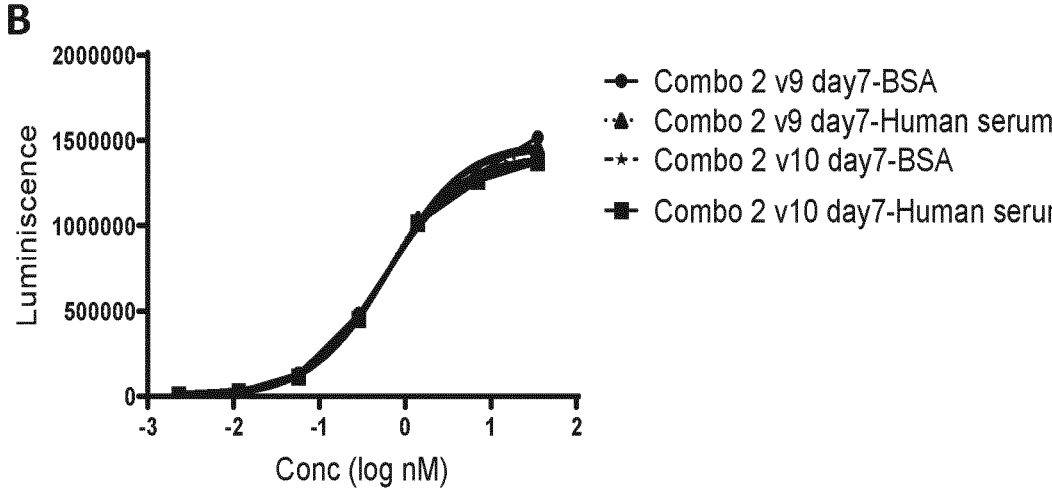

FIG. 4 shows serum stability as measured in dual ELISA. Samples, A) Combo 1 variants (CD137-5T4 bispecific) or B) Combo 2 variants (CD40-EpCAM bispecific), were incubated at 37° C. in human serum or PBS supplemented with BSA for 7 days. Binding to targets remained unaltered after incubation.

Figure 5:
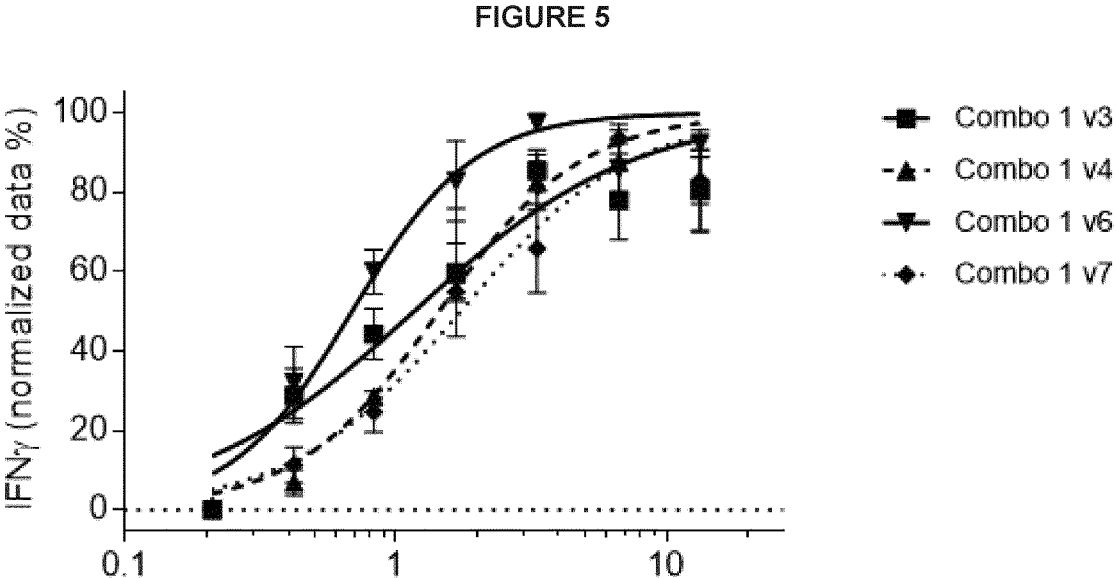
Figure 5:
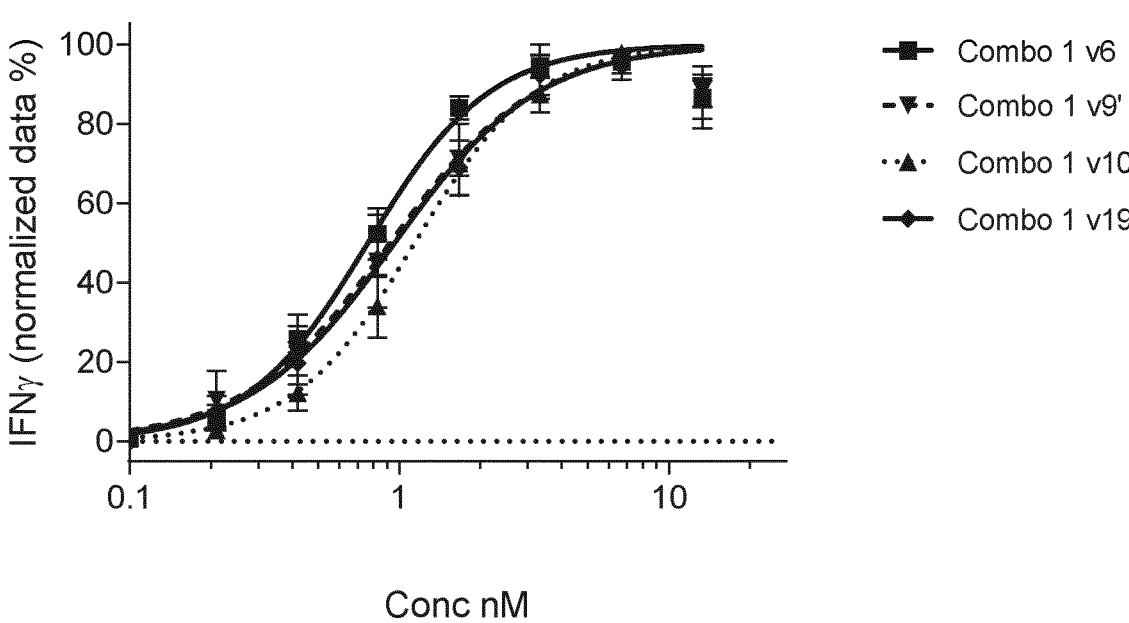

FIG. 5 shows T cell activation of Combo 1 constructs (CD137-5T4 bispecific), measured by secretion of IFN-γ.

Figure 6:
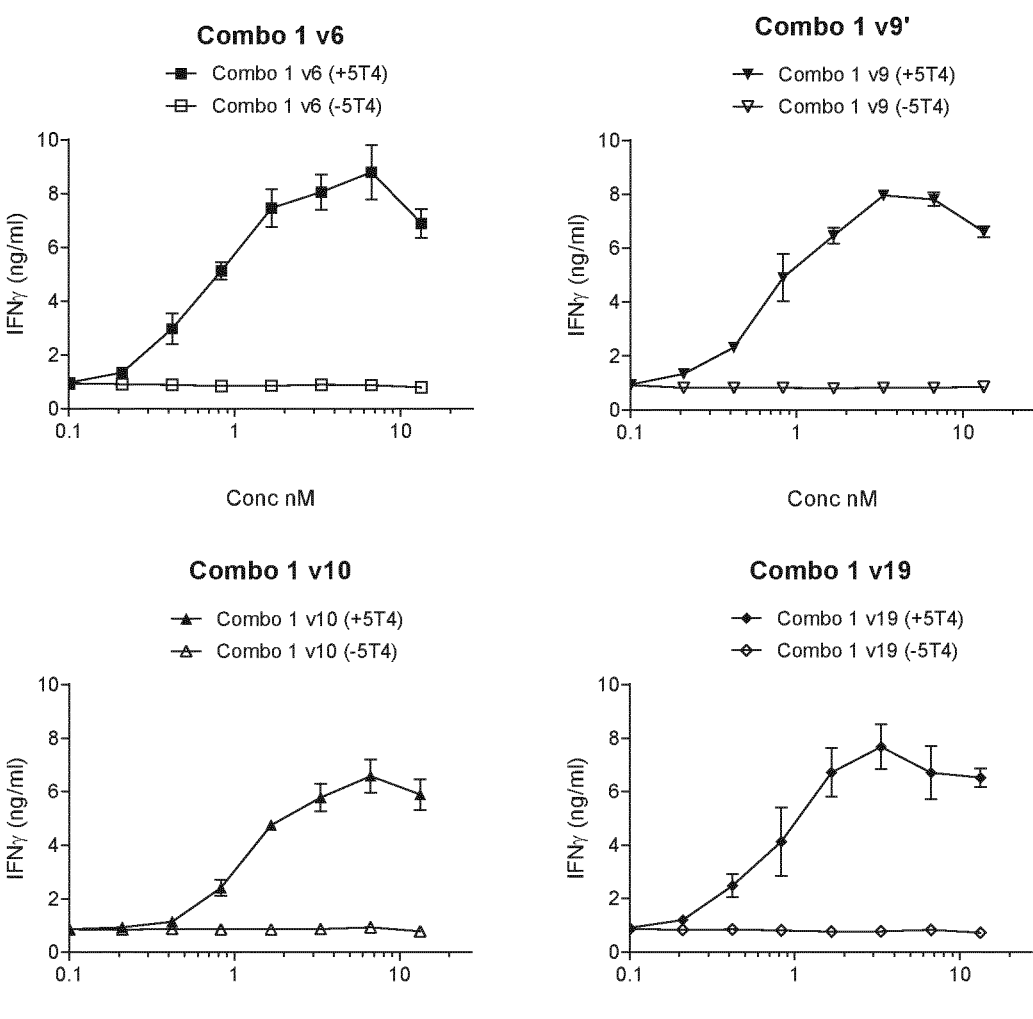

FIG. 6 shows agonistic function of four Combo 1 constructs (CD137-5T4 bispecific) on human CD8+ T cells. Dose response-dependent IFNγ production (absolute values) by human CD8+ T cells from one representative individual donor, activated with the bispecific constructs, in the presence or absence of immobilized 5T4-Fc. Obtained mean (and SD) IFNγ levels from one representative individual donor are shown.

Figure 7:
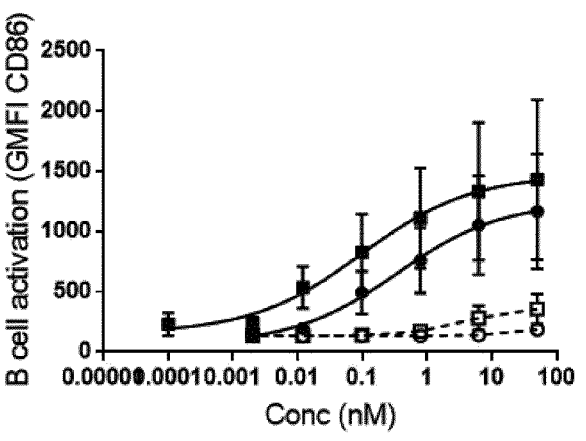
Figure 7:
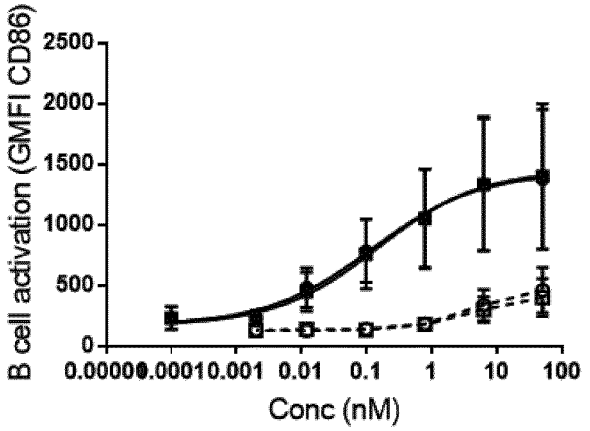

FIG. 7 shows results of a B cell activation assay with Combo 2 constructs (CD40-EpCAM bispecific). Dose-dependent upregulation of CD86 (geometric mean fluorescence intensity) on CD19+ B cells activated with the bispecific Combo 2 constructs in the presence of CHO cells expressing Combo 2 Ag2 or control CHO cells is shown. The graph displays the mean (+/–SD) of three donors in one representative experiment.

Figure 8:
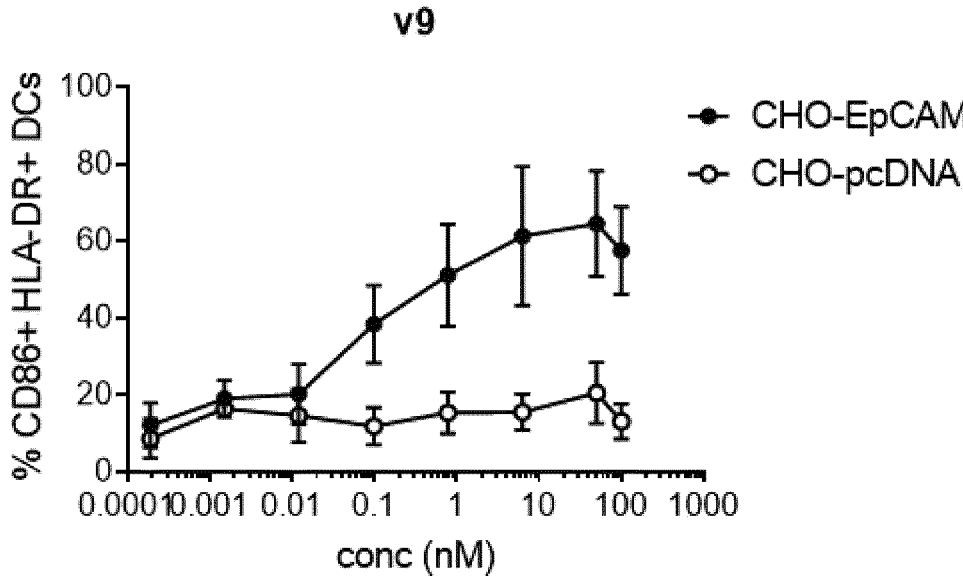
Figure 8:
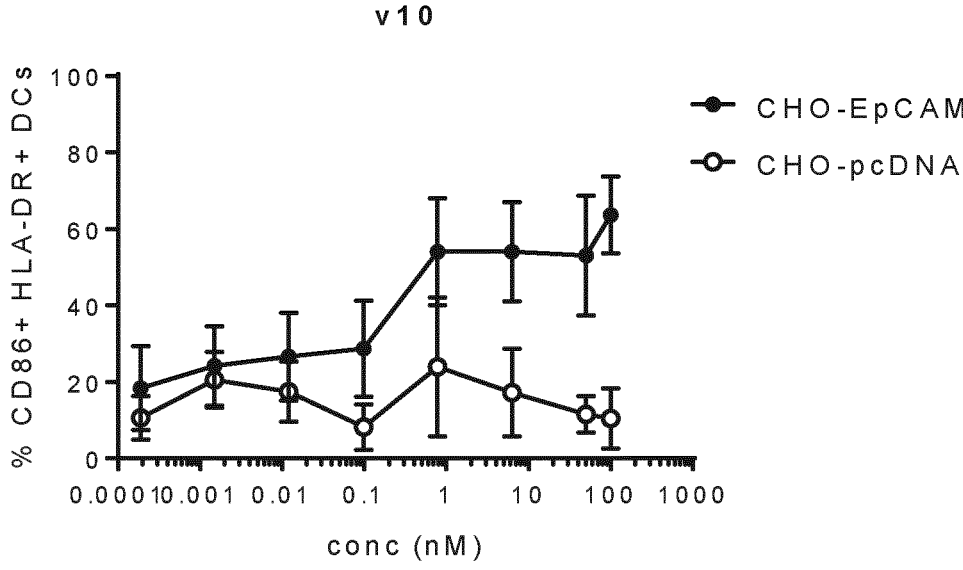

FIG. 8 shows results of a DC activation assay with Combo 2 constructs (CD40-EpCAM bispecific). Monocyte-derived DCs were activated with Combo 2 constructs in the presence of CHO cells expressing Combo 2 Ag2 or control CHO cells. Flow cytometry was used to analyze the frequency of CD86+ HLA-DR+ cells in the CD1a+ CD14– population. Combo 2 constructs induce a dose-dependent increase in CD86+ HLA-DR+ cells. Results are the mean (+/–SEM) of four donors, pooled from three experiments.

Figure 9:
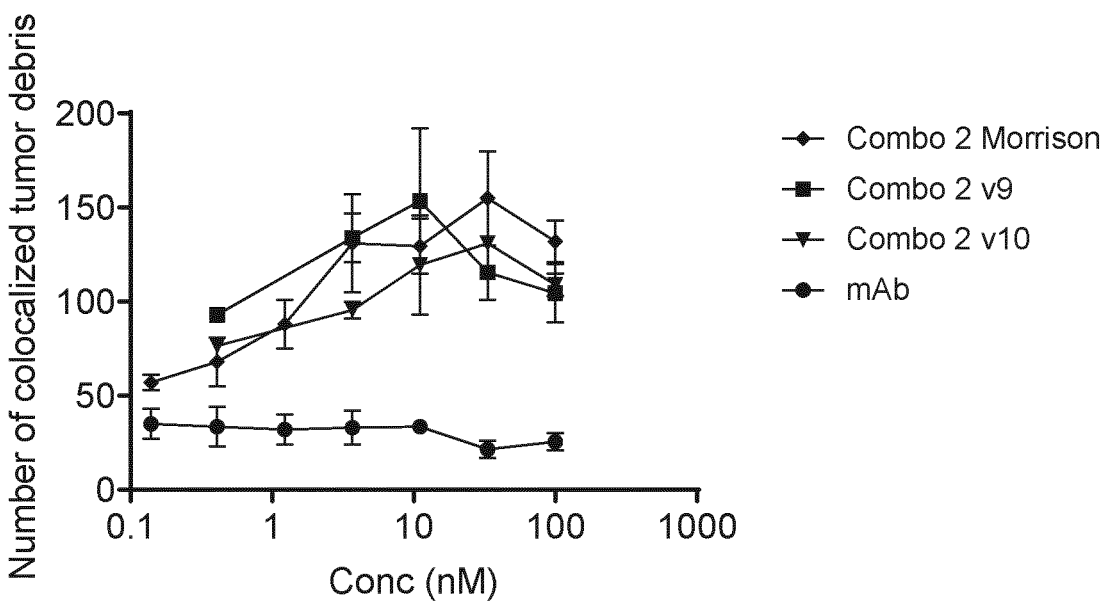

FIG. 9 shows colocalization of tumour debris and Raji cells. Fluorescently-labelled Raji cells were incubated with Ag2-expressing fluorescently-labelled tumour debris and Abs. Images were captured with a Cytation5 live imaging system and the number of tumour debris colocalized with Raji cells after 3 h was analysed using Gen5 software. The graph shows the mean (+/–SEM) of two replicates in one representative experiment of three.

Figure 10:
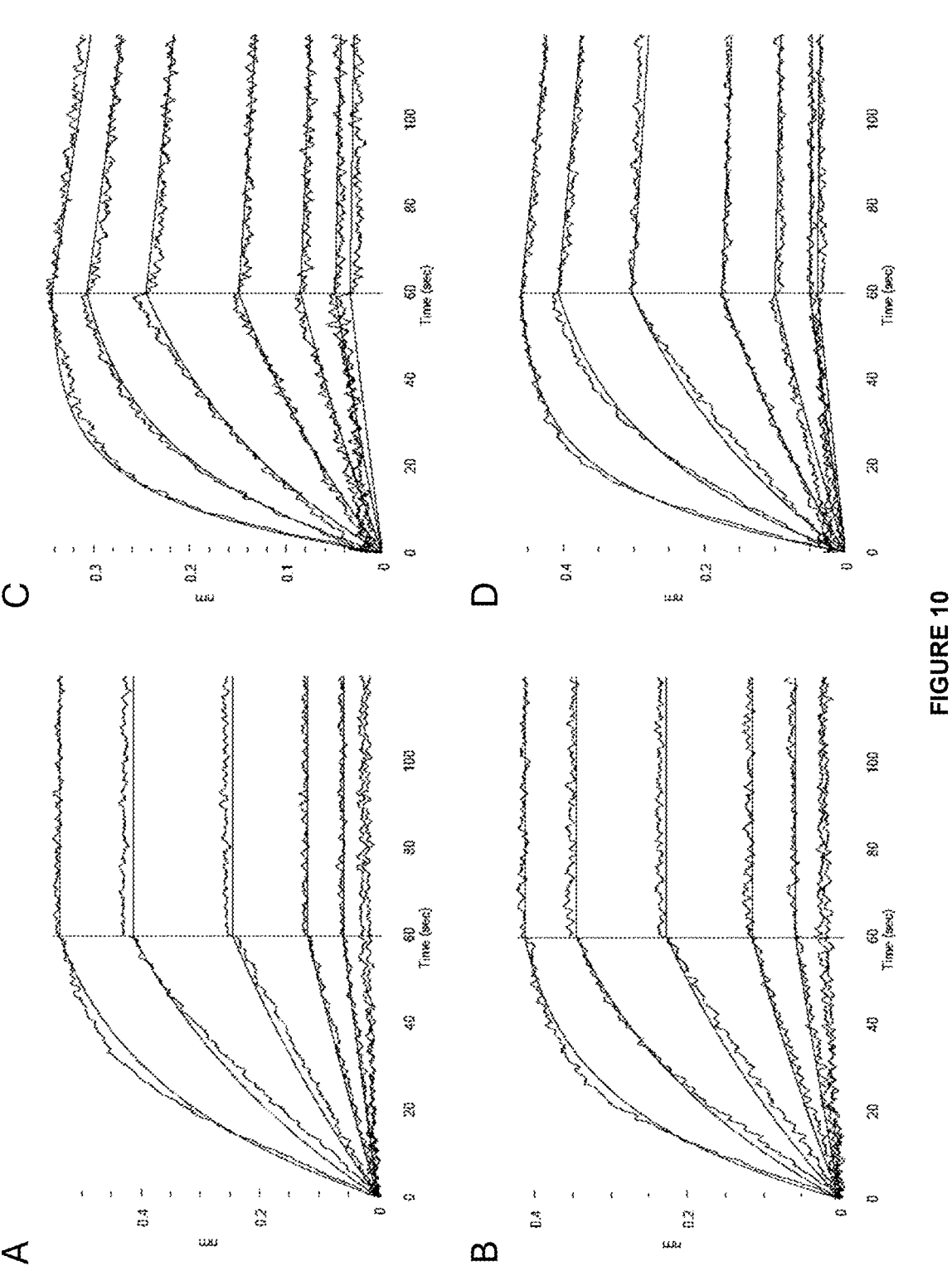

FIG. 10. Representative Octet chromatograms of binding between novel IgG-Fab bsAb constructs against Fcgamma receptors. IgG1 and IgG4 IgG-Fab bsAb constructs and monoclonal IgG1 and IgG4 isotype controls were tested for binding to hFcγRI. Similar binding is detected for IgG1 mAb (A) compared to variant 9 IgG1 IgG-Fab bsAb construct (B) as well as for IgG4 S228P mAb (C) compared to variant 9 IgG4 S228P IgG-Fab bsAb construct.

Figure 11:
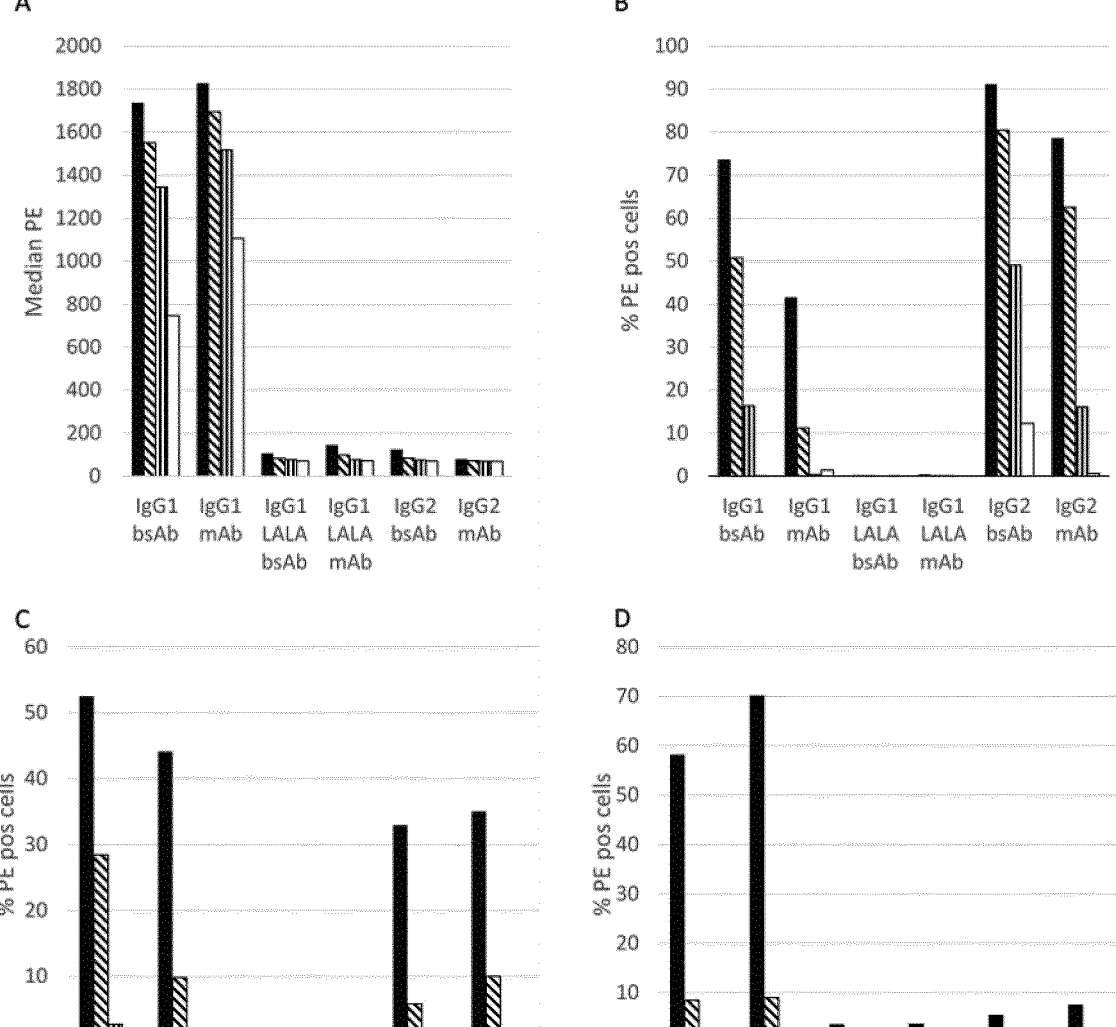

FIG. 11. PE median or percentage of positive cell signals of binding of novel variant 9 IgG-Fab bsAb or mAb IgG1, IgG1 LALA or IgG2 constructs, at 50 (black bars), 10 (diagonal black and white bars), 2 (vertical black and white bars) or 0.4 μg/mL (white bars), to cells expressing human (A) FcγRI, (B)R131FcγRIIa H131, (C) FcγRIIa or (D) FcγRIIb. Novel variant 9 IgG-Fab bsAb and monoclonal constructs of same isotype bind similarly to the same cells indicating that the novel IgG-Fab bsAb constructs have retained Fc gamma receptor functions compared to monoclonal antibodies.

Figure 12:
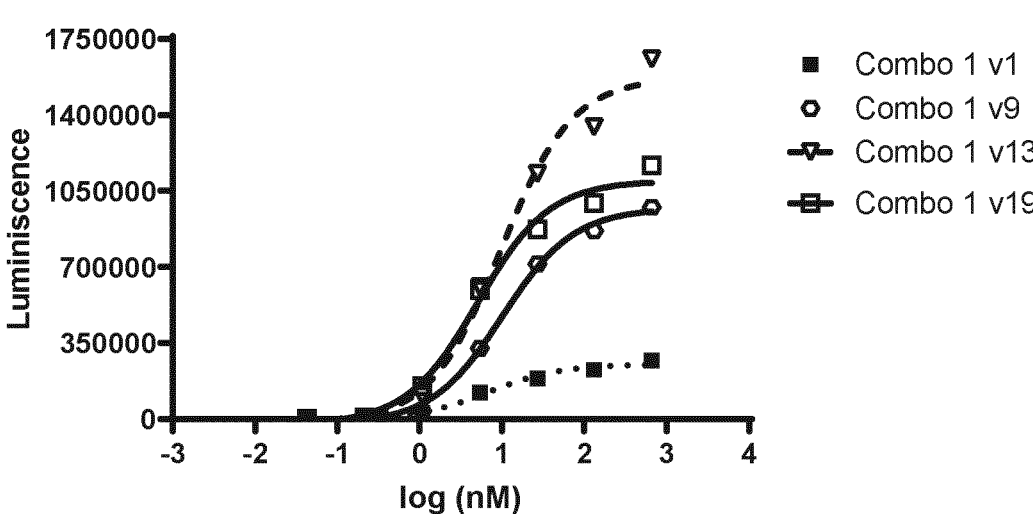

FIG. 12. shows representative dual ELISA binding curves for Combo 1 constructs (CD137-5T4 IgG like antibodies). Higher signals are observed for variant 9, 13 and 19 constructs compared to variant 1.

Figure 13:
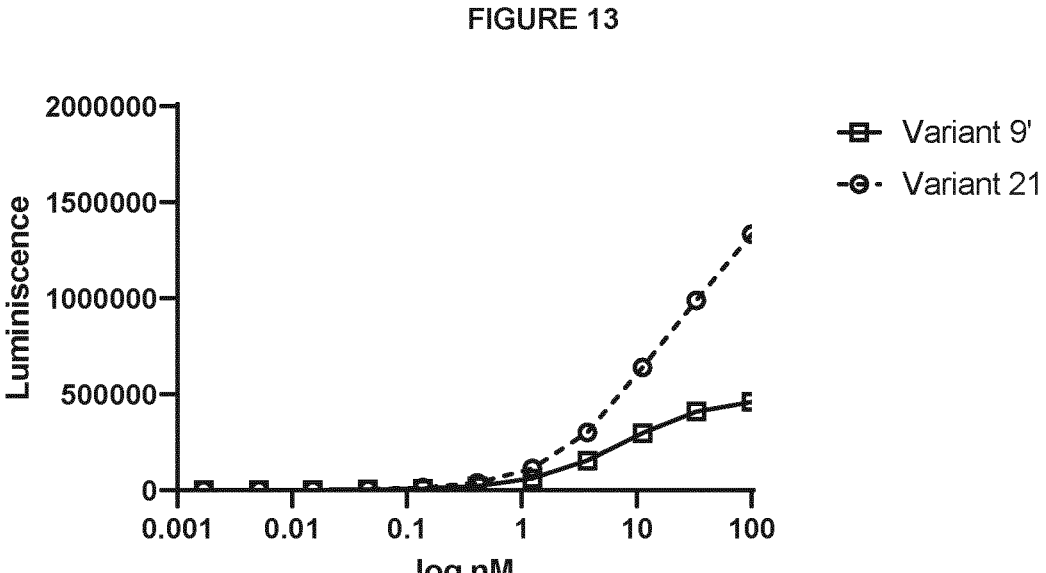

FIG. 13 shows representative dual ELISA binding curves for A) Combo 1 constructs (CD137-5T4 bispecific).

Figure 14:
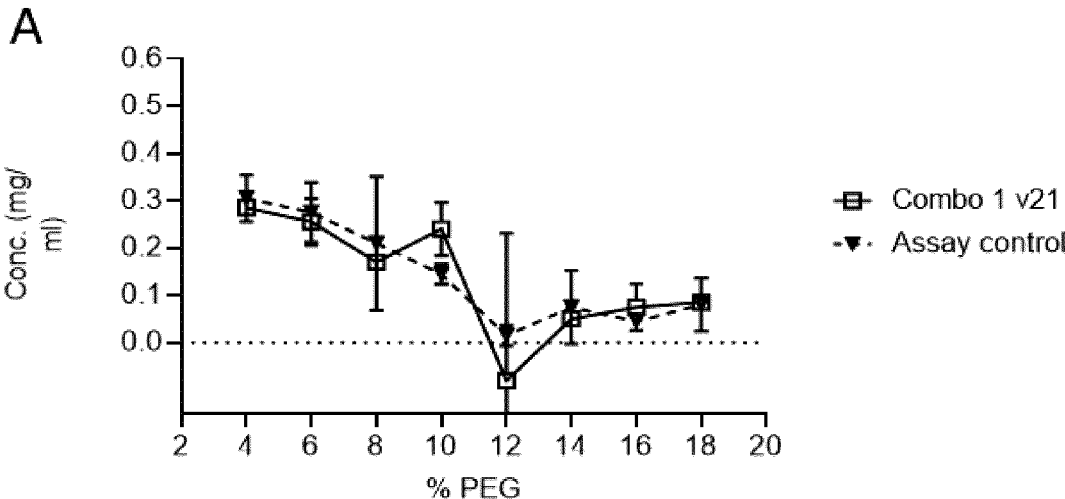

FIG. 14. Precipitation curves of samples A) Combo 1 constructs variant 21 incubated with PEG at different concentrations to test ability to self-interact. <50% protein loss is observed for PEG concentrations, >9% indicating low self-interaction and good colloidal stability.

Figure 15:
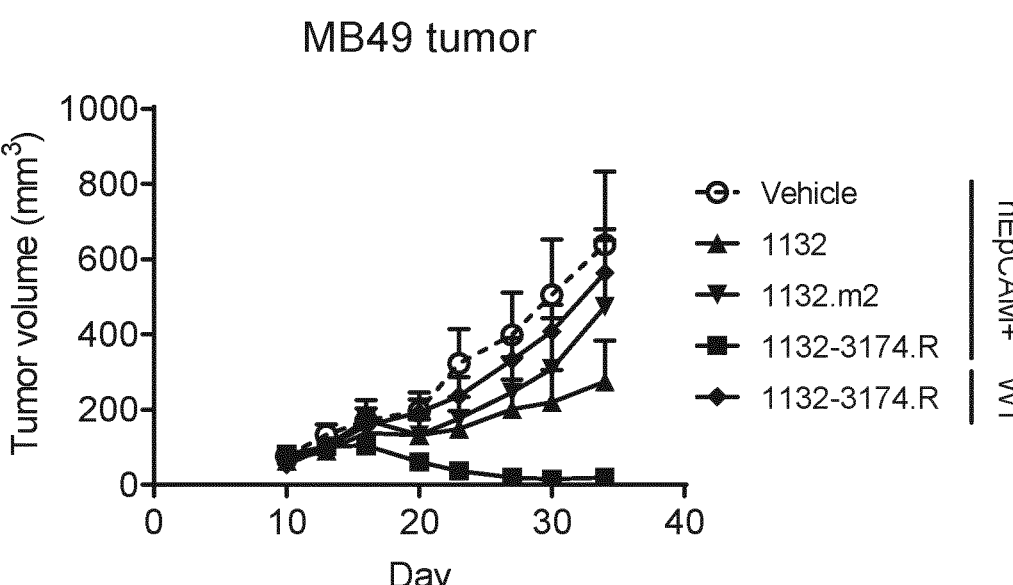
Figure 15:
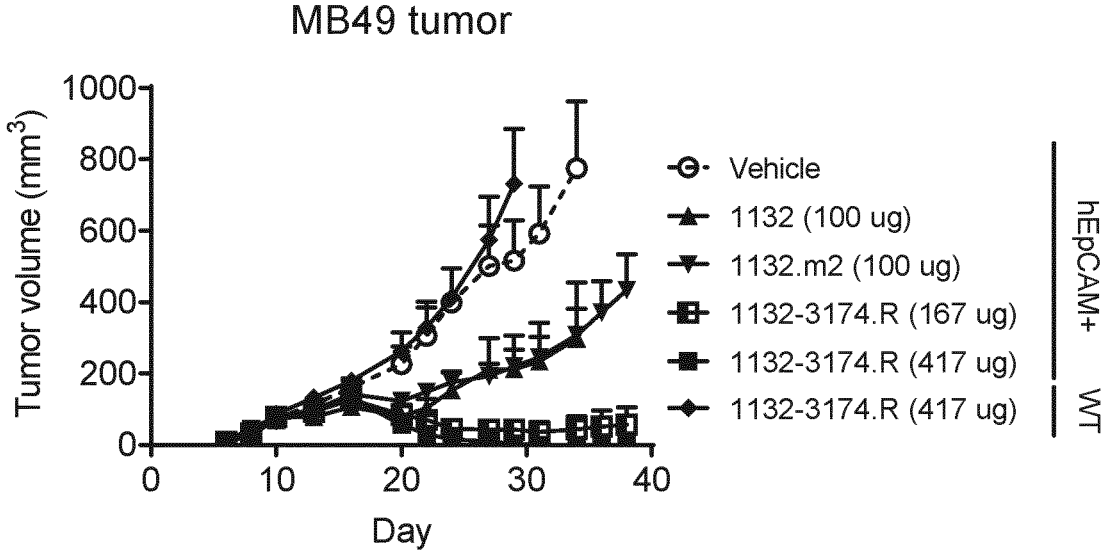

FIG. 15. MB49 tumour growth. hCD40tg mice inoculated with MB49 tumours, which were either hEpCAM positive or negative, were dosed with the indicated treatments on days 10, 13 and 16 post-inoculation. Tumours were frequently measured until the first mouse in any of the treatment groups reached a tumour volume above the ethical limit.

Figure 16:
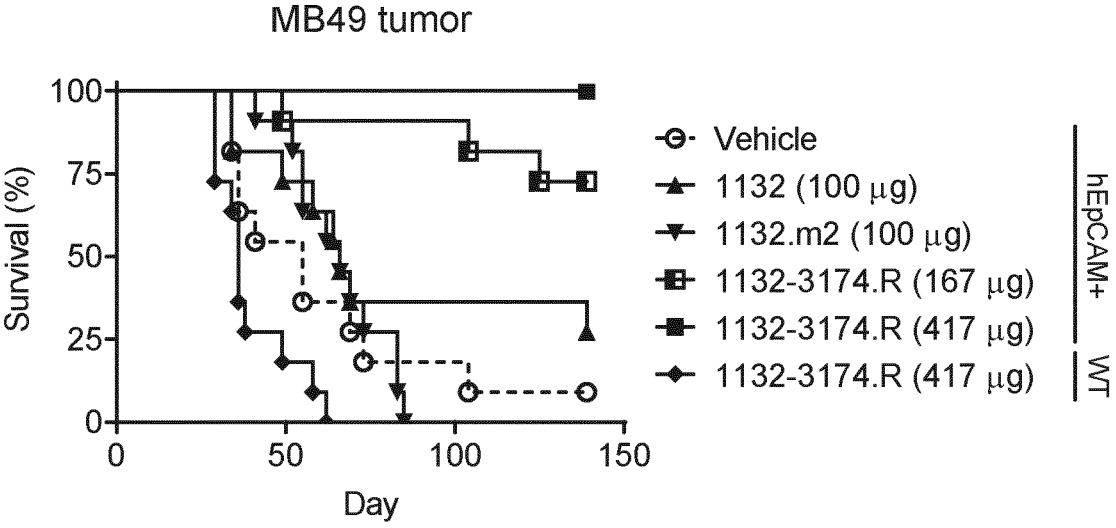

FIG. 16. Survival of MB49 tumour-bearing mice. hCD40tg mice inoculated with MB49 tumours, which were either hEpCAM positive or negative, were dosed with the indicated treatments on days 10, 13 and 16 post-inoculation. Mice were kept in the study until their tumour volume reached the ethical limit of 2000 mm3, at which point the mice were sacrificed.

EXAMPLES

Example 1—Generation and Manufacturability Evaluation of 20 Variants in IgG-Fab Architecture

Material and Methods

Design

Novel bispecific constructs consisting of an immunoglobulin (IgG) coupled to two Fab fragments connected via a polypetide linker between the C-terminal end of the IgG and the N-terminal end of the light chain of the Fab fragments (FIG. 1) were engineered in different variants. Variants were generated using different mutation combinations in the interface between VH-CH1 and VL-CKappa. The mutations used were such known in the public domain.

Manufacturability

Bispecific antibodies were expressed using transient HEK293 and Expi293 HEK (Life technologies) cultures at different volumes ranging from 600 μL-2 L according to manufacturer's instructions. Purification of bispecifics from supernatants was made on protein A using the NGC system (BioRad), the AKTA Avant system (GE Healthcare) or Predictor MabSelectSure 50 μl 96 well plates (GE Healthcare). Cells were transfected with three different vectors encoding separately for each of the three polypeptides chains (i.e. the immunoglobulin heavy chain linked to the Fab light chain, the immunoglobulin light chain and the Fab heavy chain). Different transfection ratios of the three vectors were tested. Aggregation was measured with SE-HPLC in a 1260 Infinity II system (Agilent Technologies) using a TSK gel Super SW mAB HTP 4 μm, 4.6×150 mm column (TOSOH Bioscience) and 100 mM Sodium Phosphate, pH 6.8, 300 mM NaCl as mobile phase at ambient temperature and a flow rate of 0.35 ml/min.

Results

A total of 20 different variants were generated and evaluated. Two different antibody combinations (Combo 1 (CD137-5T4 bispecific) and Combo 2 (CD40-EpCAM bispecific)) were tested. A description of the mutational strategies used, how these differed between the two different FAbs, and which mutations that were tested, are listed in Table 1, 2 and 3.

The expression and the aggregation levels after transient small-scale production in HEK cells and purification on protein A columns varied dramatically between bsAb variants that differed only in the mutations introduced between the CH1-CKappa and VH-VL interfaces as seen in Table 4. Variant 1 construct carrying no mutations aggregated severely during expression/purification. All mutations introduced improved the purity and quality of the expressed bispecific antibodies lowering the levels of aggregation. However, some mutation combinations such as in variants 6, 9, 10, 13, 17 and 19 generated constructs, where the produced bispecific antibody displayed surprisingly low levels of aggregation. The aggregation could further be reduced by changing the transfection ratio of the three vectors used to transform HEK cells for production of the bispecific antibody. Production of bispecific antibodies with optimized transfection ratios resulted in expression of bispecific constructs with a very high purity, displaying aggregation levels at less than 5%, which suggests that the method described would result in bispecific antibodies of high quality (Table 4).

The results are particularly surprising as data showed that it was not possible to predict in beforehand which combination of mutations and an in which domain (the IgG or the Fab) that would be most beneficial.

TABLE 1

Mutational strategies to avoid pairing of the long heavy chain with itself and pairing of L1 with H2 short and promote correct chain pairing in the Fab domain and immunoglobulin.

| | Immunoglobulin | | Fab | |
| --- | --- | --- | --- | --- |
| | CH1-CK | VH-VL | CH1-CK | VH-VL |
| Variant 1 | — | — | — | — |
| Variant 2 | Set 1 (steric) | — | — | — |
| Variant 3 | Set 1 (steric) | Set 5b (salt) | — | Set 5a (salt) |
| Variant 4 | Set 1 (steric) | Set 5b (salt) | — | Set 5a (salt) and Set 6 (SS) |
| Variant 5 | Set 2 (hydrophob) | — | Set 3 (salt) | — |
| Variant 6 | Set 2 (hydrophob) | Set 5b (salt) | Set 3 (salt) | Set 5a (salt) |
| Variant 7 | Set 2 (hydrophob) | Set 5b (salt) | Set 3 (salt) | Set 5a (salt) and Set 6 (SS) |
| Variant 8 | — | — | Set 4 (SS) | — |
| Variant 9 | Set 1 (steric) | Set 5b (salt) | Set 3 (salt) | Set 5a (salt) |
| Variant 9' | Set 1 (steric) | Set 5b (salt) | Set 3' (charge-Alanine) | Set 5a (salt) |
| Variant 10 | Set 1 (steric) | Set 5b (salt) | Set 3 (salt) | Set 5a (salt) and Set 6 (SS) |
| Variant 11 | Set 3 (salt) | Set 5b (salt) | Set 1 (steric) | Set 5a (salt) |
| Variant 12 | Set 3 (salt) | Set 5b (salt) | Set 1 (steric) | Set 5a (salt) and Set 6 (SS) |

TABLE 1-continued

Mutational strategies to avoid pairing of the long heavy chain with itself and pairing of L1 with H2 short and promote correct chain pairing in the Fab domain and immunoglobulin.

| | Immunoglobulin | | Fab | |
| --- | --- | --- | --- | --- |
| | CH1-CK | VH-VL | CH1-CK | VH-VL |
| Variant 13 | — | Set 7 (2 x salt) | Set 1 (steric) | Set 5a (salt) |
| Variant 14 | — | Set 7 (2 x salt) | Set 1 (steric) | Set 5a (salt) and Set 6 (SS) |
| Variant 15 | Set 3 (salt) | Set 7 (2 x salt) | Set 1 (steric) | Set 5a (salt) |
| Variant 16 | Set 3 (salt) | Set 7 (2 x salt) | Set 1 (steric) | Set 5a (salt) and Set 6 (SS) |
| Variant 17 | Set 2 (hydrophob) | Set 5b (salt) | Set 1 (steric) and Set 3 (salt) | Set 5a (salt) |
| Variant 18 | Set 2 (hydrophob) | Set 5b (salt) | Set 1 (steric) and Set 3 (salt) | Set 5a (salt) and Set 6 (SS) |
| Variant 19 | Set 1 (steric) and Set 3 (salt) | Set 5b (salt) | Set 2 (hydrophob) | Set 5a (salt) |
| Variant 20 | Set 1 (steric) and Set 3 (salt) | Set 5b (salt) | Set 2 (hydrophob) | Set 5a (salt) and Set 6 (SS) |

TABLE 2

Mutations introduced between CH1 and CKappa interface and VL and VH interface.

| | Domain | Mutation* |
| --- | --- | --- |
| Set 1 | CH1 | H168A, F170G |
| | CKappa | L135Y, S176W |
| Set 2 | CH1 | L145Q, S183V |
| | CKappa | V133T, S176V |
| Set 3 | CH1 | T187E |
| | CKappa | S114A, N137K |
| Set 3' | CH1 | T187E |
| | CKappa | S114A |
| Set 4 | CH1 | F126C |
| | CKappa | S121C |
| Set 5a | VL | Q44R |
| | VH | Q44E |
| Set 5b | VL | Q44E |
| | VH | Q44R |
| Set 6 | VL | Q120C or A120C |
| | VH | G49C |
| Set 7 | VL | Q44D, A49D |
| | VH | Q44K, Q120K |

* Mutation in CH1 and CKappa interface are in the EU numbering system, Mutations in VL (variable light) and VH (variable heavy) are in IMGT numbering system.

TABLE 3a

Mutations‡ included in the different variatns generated.

| | H1 long | L1 | H2 short |
| --- | --- | --- | --- |
| Variant 1 | VH$_A$-CH1$_A$-FC-linker-VL$_B$-CKappa1$_B$ | VL$_A$-CKappa$_A$ | VH$_B$-CH1$_B$ |
| Variant 2 | VH$_A$-CH1$_A$ (H172A, F174G)-FC-linker-VL$_B$-CKappa1$_B$ | VL$_A$-CKappa$_A$ (L135Y, S176W) | VH$_B$-CH1$_B$ |
| Variant 3 | VH$_A$ (Q44R)-CH1$_A$ (H172A, F174G)-FC-linker VL$_B$ (Q44R)-CKappa1$_B$ | VL$_A$ (Q44E)-CKappa$_A$ (L135Y, S176W) | VHR$_B$ (Q44E)-CH1$_B$ |
| Variant 4 | VH$_A$ (Q44R)-CH1$_A$ (H172A, F174G)-FC-linker-VL$_B$ (Q44R, G49C)-CKappa1$_B$ | VL$_A$ (Q44E)-CKappa$_A$ (L135Y, S176W) | VH$_B$ (Q44E, Q120C)-CH1$_B$ |

TABLE 3a-continued

Mutations‡ included in the different variatns generated.

| | H1 long | L1 | H2 short |
|---|---|---|---|
| Variant 5 | VH$_A$-CH1$_A$ (L145Q, S183V)-FC-linker-VL$_B$-CKappa1$_B$ (S114A, N137K) | VL$_A$-CKappa$_A$ (V133T, S176V) | VH$_B$-CH1$_B$ (T187E) |
| Variant 6 | VH$_A$ (Q44R)-CH1$_A$ (L145Q, S183V)-FC-linker-VL$_B$ (Q44R)-CKappa1$_B$ (S114A, N137K) | VL$_A$ (Q44E)-CKappa$_A$ (V133T, S176V) | VH$_B$ (Q44E)-CH1$_B$ (T187E) |
| Variant 7 | VH$_A$ (Q44R)-CH1$_A$ (L145Q, S183V)-FC-linker-VL$_B$ (Q44R, G49C)-CKappa1$_B$ (S114A, N137K) | VL$_A$ (Q44E)-CKappa$_A$ (V133T, S176V) | VH$_B$ (Q44E, Q120C)-CH1$_B$ (T187E) |
| Variant 8 | VH$_A$-CH1$_A$-FC-linker-VL$_B$-CKappa1$_B$ (S121C) | VL$_A$-CKappa$_A$ | VH$_B$-CH1$_B$ (F126C) |
| Variant 9 | VH$_A$ (Q44R)-CH1$_A$ (H172A, F174G)-FC-linker-VL$_B$ (Q44R)-CKappa1$_B$ (S114A, N137K) | VL$_A$ (Q44E)-CKappa$_A$ (L135Y, S176W) | VH$_B$ (Q44E)-CH1$_B$ (T187E) |
| Variant 9' | VH$_A$ (Q44R)-CH1$_A$ (H168A, F170G)-FC-linker-VL$_B$ (Q44R)-CKappa1$_B$ (S114$_A$) | VL$_A$ (Q44E)-CKappa$_A$ (L135Y, S176W) | VH$_B$ (Q44E)-CH1$_B$ (T187E) |
| Variant 10 | VH$_A$ (Q44R)-CH1$_A$ (H172A, F174G)-FC-linker-VL$_B$ (Q44R, Q120C)-CKappa1$_B$ (S114A, N137K) | VL$_A$ (Q44E)-CKappa$_A$ (L135Y, S176W) | VH$_B$ (Q44E, G49C)-CH1$_B$ (T187E) |
| Variant 11 | VH$_A$ (Q44R)-CH1$_A$ (T187E)-FC-linker-VL$_B$ (Q44R)-CKappa1$_B$ (L135Y, S176W) | VL$_A$ (Q44E)-CKappa$_A$ (S114A, N137K) | VH$_B$ (Q44E)-CH1$_B$ (H172A, F174G) |
| Variant 12 | VH$_A$ (Q44R)-CH1$_A$ (T187E)-FC-linker-VL$_B$ (Q44R, Q120C)-CKappa1$_B$ (L135Y, S176W) | VL$_A$ (Q44E)-CKappa$_A$ (S114A, N137K) | VH$_B$ (Q44E, G49C)-CH1$_B$ (H172A, F174G) |
| Variant 13 | VH$_A$ (Q44K, Q120K)-CH1$_A$-FC-linker-VL$_B$ (Q44R)-CKappa1$_B$ (L135Y, S176W) | VL$_A$ (Q44D, A49D)-CKappa$_A$ | VH$_B$ (Q44E)-CH1$_B$ (H172A, F174G) |
| Variant 14 | VH$_A$ (Q44K, Q120K)-CH1$_A$-FC-linker-VL$_B$ (Q44R, Q120C)-CKappa1$_B$ (L135Y, S176W) | VL$_A$ (Q44D, A49D)-CKappa$_A$ | VH$_B$ (Q44E, G49C)-CH1$_B$ (H172A, F174G) |
| Variant 15 | VH$_A$ (Q44K, Q120K)-CH1$_A$ (T187E)-FC-linker-VL$_B$ (Q44R)-CKappa1$_B$ (L135Y, S176W) | VL$_A$ (Q44D, A49D)-CKappa$_A$ (S114A, N137K) | VH$_B$ (Q44E)-CH1$_B$ (H172A, F174G) |
| Variant 16 | VH$_A$ (Q44K, Q120K)-CH1$_A$ (T187E)-FC-linker-VL$_B$ (Q44R, Q120C)-CKappa1$_B$ (L135Y, S176W) | VL$_A$ (Q44D, A49D)-CKappa$_A$ (S114A, N137K) | VH$_B$ (Q44E, G49C)-CH1$_B$ (H172A, F174G) |
| Variant 17 | VH$_A$ (Q44R)-CH1$_A$ (L145Q, S183V)-FC-linker-VL$_B$ (Q44R)-CKappa1$_B$ (L135Y, S176W, S114A, N137K) | VL$_A$ (Q44E)-CKappa$_A$ (V133T, S176V) | VH$_B$ (Q44E)-CH1$_B$ (H172A, F174G, T187E) |
| Variant 18 | VH$_A$ (Q44R)-CH1$_A$ (L145Q, S183V)-FC-linker-VL$_B$ (Q44R, Q120C)-CKappa1$_B$ (L135Y, S176W, S114A, N137K) | VL$_A$ (Q44E)-CKappa$_A$ (V133T, S176V) | VH$_B$ (Q44E, G49C)-CH1$_B$ (H172A, F174G, T187E) |
| Variant 19 | VH$_A$ (Q44R)-CH1$_A$ (H172A, F174G, T187E)-FC-linker-VL$_B$ (Q44R)-CKappa1$_B$ (V133T, S176V) | VL$_A$ (Q44E)-CKappa$_A$ (L135Y, S176W, S114A, N137K) | VH$_B$ (Q44E)-CH1$_B$ (L145Q, S183V) |

TABLE 3a-continued

Mutations‡ included in the different variatns generated.

| | H1 long | L1 | H2 short |
|---|---|---|---|
| Variant 20 | VH$_A$ (Q44R)-CH1$_A$ (H172A, F174G, T187E)-FC-linker-VL$_B$ (Q44R, Q120C)-CKappa1$_B$ (V133T, S176V) | VL$_A$ (Q44E)-CKappa$_A$ (L135Y, S176W, S114A, N137K) | VH$_B$ (Q44E, G49C)-CH1$_B$ (L145Q, S183V) |

‡Mutation in CH1 and CKappa interface are in the EU numbering system, except for mutations H172A and F174G that are in the Kabat numbering system.
Mutations in VL (variable light) and VH (variable heavy) are in IMGT numbering system.

TABLE 3b

Mutations‡ included in the different variatns generated.

| | H1 long | L1 | H2 short |
|---|---|---|---|
| Variant 1 | VH$_A$-CH1$_A$-FC-linker-V$_B$-CKappa1$_B$ | VL$_A$-CKappa$_A$ | VH$_B$-CH1$_B$ |
| Variant 2 | VH$_A$-CH1$_A$ (H168A, F170G)-FC-linker-VL$_B$-CKappa1$_B$ | VLA-CKappa$_A$ (L135Y, S176W) | VH$_B$-CH1$_B$ |
| Variant 3 | VH$_A$ (Q44R)-CH1$_A$ (H168A, F170G)-FC-linker-VL$_B$ (Q44R)-CKappa1$_B$ | VL$_A$ (Q44E)-CKappa$_A$ (L135Y, S176W) | VH$_B$ (Q44E)-CH1$_B$ |
| Variant 4 | VH$_A$ (Q44R)-CH1$_A$ (H168A, F170G)-FC-linker-VL$_B$ (Q44R, G49C)-CKappa1$_B$ | VL$_A$ (Q44E)-CKappa$_A$ (L135Y, S176W) | VH$_B$ (Q44E, Q120C)-CH1$_B$ |
| Variant 5 | VH$_A$-CH1$_A$ (L145Q, S183V)-FC-linker-VL$_B$-CKappa1$_B$ (S114A, N137K) | VL$_A$-CKappa$_A$ (V133T, S176V) | VH$_B$-CH1$_B$ (T187E) |
| Variant 6 | VH$_A$ (Q44R)-CH1$_A$ (L145Q, S183V)-FC-linker-VL$_B$ (Q44R)-CKappa1$_B$ (S114A, N137K) | VL$_A$ (Q44E)-CKappa$_A$ (V133T, S176V) | VH$_B$ (Q44E)-CH1$_B$ (T187E) |
| Variant 7 | VH$_A$ (Q44R)-CH1$_A$ (L145Q, S183V)-FC-linker VL$_B$ (Q44R, G49C)-CKappa1$_B$ (S114A, N137K) | VL$_A$ (Q44E)-CKappa$_A$ (V133T, S176V) | VH$_B$ (Q44E, Q120C)-CH1$_B$ (T187E) |
| Variant 8 | VH$_A$-CH1$_A$-FC-linker-VL$_B$-CKappa1$_B$ (S121C) | VL$_A$-CKappa$_A$ | VH$_B$-CH1$_B$ (F126C) |
| Variant 9 | VH$_A$ (Q44R)-CH1$_A$ (H168A, F170G)-FC-linker-VL$_B$ (Q44R)-CKappa1$_B$ (S114A, N137K) | VL$_A$ (Q44E)-CKappa$_A$ (L135Y, S176W) | VH$_B$ (Q44E)-CH1$_B$ (T187E) |
| Variant 9' | VH$_A$ (Q44R)-CH1$_A$ (H168A, F170G)-FC-linker-VL$_B$ (Q44R)-CKappa1$_B$ (S114$_A$) | VL$_A$ (Q44E)-CKappa$_A$ (L135Y, S176W) | VH$_B$ (Q44E)-CH1$_B$ (T187E) |
| Variant 10 | VH$_A$ (Q44R)-CH1$_A$ (H168A, F170G)-FC-linker VL$_B$ (Q44R, Q120C)-CKappa1$_B$ (S114A, N137K) | VL$_A$ (Q44E)-CKappa$_A$ (L135Y, S176W) | VH$_B$ (Q44E, G49C)-CH1$_B$ (T187E) |
| Variant 11 | VH$_A$ (Q44R)-CH1$_A$ (T187E)-FC-linker-VL$_B$ (Q44R)-CKappa1$_B$ (L135Y, S176W) | VL$_A$ (Q44E)-CKappa$_A$ (S114A, N137K) | VH$_B$ (Q44E)-CH1$_B$ (H168A, F170G) |
| Variant 12 | VH$_A$ (Q44R)-CH1$_A$ (T187E)-FC-linker-VL$_B$ (Q44R, Q120C)-CKappa1$_B$ (L135Y, S176W) | VL$_A$ (Q44E)-CKappa$_A$ (S114A, N137K) | VH$_B$ (Q44E, G49C)-CH1$_B$ (H168A, F170G) |

TABLE 3b-continued

Mutations‡ included in the different variatns generated.

| | H1 long | L1 | H2 short |
|---|---|---|---|
| Variant 13 | VH$_A$ (Q44K, Q120K)-CH1$_A$-FC-linker-VL$_B$ (Q44R)-CKappa1$_B$ (L135Y, S176W) | VL$_A$ (Q44D, A49D)-CKappa$_A$ | VH$_B$ (Q44E)-CH1$_B$ (H168A, F170G) |
| Variant 14 | VH$_A$ (Q44K, Q120K)-CH1$_A$-FC-linker-VL$_B$ (Q44R, Q120C)-CKappa1$_B$ (L135Y, S176W) | VL$_A$ (Q44D, A49D)-CKappa$_A$ | VH$_B$ (Q44E, G49C)-CH1$_B$ (H168A, F170G) |
| Variant 15 | VH$_A$ (Q44K, Q120K)-CH1$_A$ (T187E)-FC-linker VL$_B$ (Q44R)-CKappa1$_B$ (L135Y, S176W) | VL$_A$ (Q44D, A49D)-CKappa$_A$ (S114A, N137K) | VH$_B$ (Q44E)-CH1$_B$ (H168A, F170G) |
| Variant 16 | VH$_A$ (Q44K, Q120K)-CH1$_A$ (T187E)-FC-linker VL$_B$ (Q44R, Q120C or A120C-CKappa1$_B$ (L135Y, S176W) | VL$_A$ (Q44D, A49D)-CKappa$_A$ (S114A, N137K) | VH$_B$ (Q44E, G49C)-CH1$_B$ (H168A, F170G) |
| Variant 17 | VH$_A$ (Q44R)-CH1$_A$ (L145Q, S183V)-FC-linker-VL$_B$ (Q44R)-CKappa1$_B$ (L135Y, S176W, S114A, N137K) | VL$_A$ (Q44E)-CKappa$_A$ (V133T, S176V) | VH$_B$ (Q44E)-CH1$_B$ (H168A, F170G, T187E) |
| Variant 18 | VH$_A$ (Q44R)-CH1$_A$ (L145Q, S183V)-FC-linker-VL$_B$ (Q44R, Q120C or A120C)-CKappa1$_B$ (L135Y, S176W, S114A, N137K) | VL$_A$ (Q44E)-CKappa$_A$ (V133T, S176V) | VH$_B$ (Q44E, G49C) CH1$_B$ (H168A, F170G, T187E) |
| Variant 19 | VH$_A$ (Q44R)-CH1$_A$ (H168A, F170G, T187E)-FC-linker-VL$_B$ (Q44R)-CKappa1$_B$ (V133T, S176V) | VL$_A$ (Q44E)-CKappa$_A$ (L135Y, S176W, S114A, N137K) | VH$_B$ (Q44E)-CH1$_B$ (L145Q, S183V) |
| Variant 20 | VH$_A$ (Q44R)-CH1$_A$ (H168A, F170G, T187E)-FC-linker-VL$_B$ (Q44R, Q120C or A120C)-CKappa1$_B$ | VL$_A$ (Q44E)-CKappa$_A$ (L135Y, S176W, S114A, N137K) | VH$_B$ (Q44E, G49C)-CH1$_B$ (L145Q, S183V) |

‡Mutation in CH1 and CKappa interface are in the EU numbering system, Mutations in VL (variable light) and VH (variable heavy) are in IMGT numbering system.

TABLE 4

Aggregation after expression and protein A purification as measured with SE-HPLC

| Variant | % aggregates, chains transfected at ratios 1:1:1 | % aggregates, chain transfection ratio optimized |
|---|---|---|
| Combo 1 v1 (no mutations) | 29.8 | |
| Combo 1 v2 | 10.4 | |
| Combo 1 v3 | 5.5 | 1.8 |
| Combo 1 v4 | 5.6 | 1.8 |
| Combo 1 v5 | 13.5 | |
| Combo 1 v6 | 6.1 | 1.6 |
| Combo 1 v7 | 7 | |
| Combo 1 v8 | 15.5 | |
| Combo 1 v9' | 6.2 | 2 |
| Combo 1 v10 | 6.8 | 1.8 |
| Combo 1 v11 | 12.6 | |
| Combo 1 v12 | 12.5 | |
| Combo 1 v13 | 13.6 | |
| Combo 1 v14 | 10.2 | |
| Combo 1 v15 | 15.2 | |
| Combo 1 v16 | 13.6 | |

TABLE 4-continued

Aggregation after expression and protein A purification as measured with SE-HPLC

| Variant | % aggregates, chains transfected at ratios 1:1:1 | % aggregates, chain transfection ratio optimized |
|---|---|---|
| Combo 1 v17 | 6.5 | 1.8 |
| Combo 1 v18 | 6.8 | 2.6 |
| Combo 1 v19 | 5.9 | 2.3 |
| Combo 1 v20 | 9.9 | |
| Combo 2 v1 (no mutations) | 48.7 | |
| Combo 2 v2 | 35.4 | |
| Combo 2 v3 | 11.1 | |
| Combo 2 v4 | 7.9 | |
| Combo 2 v5 | 38.9 | |
| Combo 2 v6 | 16.4 | |
| Combo 2 v7 | 11 | |
| Combo 2 v8 | 28.8 | |
| Combo 2 v9 | 8.6 | 1.8 |
| Combo 2 v10 | 7 | 2.1 |
| Combo 2 v11 | 25.3 | |
| Combo 2 v12 | 23.5 | |
| Combo 2 v13 | 13.2 | 3.5 |
| Combo 2 v14 | 16.3 | |
| Combo 2 v15 | 21.8 | |
| Combo 2 v16 | 19.8 | |
| Combo 2 v17 | 11.7 | 1.9 |
| Combo 2 v18 | 7.3 | |
| Combo 2 v19 | 8.7 | 2.5 |
| Combo 2 v20 | 11.8 | |

Example 2—Stability and Solubility

Material and Methods

Thermostability

The melting temperatures were measured with the UNCle system (UNchained labs). The intrinsic fluorescence was measured during linear temperature ramping from 20° C. to 95° C. at a rate of 0.4° C./minute. The data analysis was performed with the UNcle Analysis software version 2.0 using default settings.

Stability

Samples in non-optimized buffer (PBS) at low (<1 mg/mL) or high (10 mg/mL) protein concentration were incubated at 2-8° C., room temperature and 40° C. for 1, 2 and 4 weeks or 1 and 2 weeks or subjected to 3 rounds of freeze thawing. Protein degradation was measured with SE-HPLC, SDS-PAGE, A280, dual ELISA and by visual inspection.

Shear Stress Stability

Samples in duplicates were subjected to shear stress in the form of heavy agitation at 2000 rpm on the 96-well plate shaker MixMate (Eppendorf) for at least 30 minutes. Protein precipitates were removed by centrifugation at 3000 g for 10 minutes and the absorbance at 280 nm was measured using a Clariostar.

Colloidal Stability

Samples were mixed with PBS/PEG solutions with different PEG concentrations ranging from 8%-36%, added to 96-well filter plates in triplicates and incubated over night at room temperature. Filtrates obtained by centrifugation at 12000 g for 15 minutes were collected and spun down before the absorbance at 280 nm was measured (to determine loss of protein) and compared to controls.

Low pH Stability

Stability at low pH was analysed, in conjunction with protein A purification, in two ways, by exposing bsAb samples to low pH (3.5) during 30, 60, 90 or 120 minutes, either during elution from protein A or after elution and an intermediate neutralization.

Serum Stability

The stability in serum was tested by incubating samples in 50% serum/50% PBS or PBS/0.1% bovine serum albumin at 37° C. for 2 hours, 1, 2 and 7 days before analysing binding in dual ELISA.

Solubility

The solubility in PBS or 20 mM Histidine/150 mM Arginine/pH 6.0 at 10 mg/mL was measured by concentrating the samples in ultrafiltration centrifugal units (Vivaspin 6, 10 kDa MWCO, GE Healthcare). Degradation was analysed with HPLC, SDS-PAGE, A280 and by visual inspection.

bispecific) and >69° C. for Combo 1 constructs (CD137-5T4 bispecific) (Table 6) indicating that the thermostability of these constructs is high.

Samples were also concentrated to 10 mg/mL in PBS or Histidine buffer. No degradation, either due to change in buffer or to increase in concentration was observed, as measured with SE-HPLC, SDS-PAGE, A280 and by visual inspection, indicating that the constructs have a solubility of at least around 10 mg/mL in both tested buffers.

Binding to both targets remained unaltered even after incubation of constructs at 37° C. in human serum compared to samples incubated in PBS with BSA as measured in dual ELISA (FIG. 4; 7 days incubation). This showed that the constructs likely have good serum stability.

TABLE 5

Changes in degradation after different treatments to evaluate stability.

| bsAb | 25 C., 4 weeks | | 40 C., 4 weeks | | Freeze/thaw, 1 round | | Freeze/thaw, 3 rounds | | Protein loss % after shear |
|---|---|---|---|---|---|---|---|---|---|
| | Δ % HMWs | Δ % LMWs | Δ % HMWs | Δ % LMWs | Δ % HMWs | Δ % LMWs | Δ % HMWs | Δ % LMWs | stress treatment |
| Combo 1 V3 | 0 | −1 | 1 | 2 | 1 | −1 | 0 | −1 | 2 |
| Combo 1 V4 | 1 | −1 | 2 | 1 | 1 | 0 | 1 | −1 | 7 |
| Combo 1 V6 | 0 | 0 | 0 | 2 | 0 | 0 | 0 | 0 | 10 |
| Combo 1 V7 | 0 | 0 | 1 | 2 | 1 | 0 | 1 | −1 | 4 |
| Combo 1 V9' | 0 | 0 | 0 | 2 | 0 | 0 | 0 | 0 | 6 |
| Combo 1 V10 | 1 | 1 | 1 | 3 | 0 | 0 | 1 | 0 | 1 |
| Combo 1 V13* | 0 | 0 | −1 | 1 | 0 | 0 | 1 | 0 | 10 |
| Combo 1 V17 | 0 | 0 | 0 | 2 | 1 | 0 | 1 | 0 | 9 |
| Combo 1 V18 | 1 | 1 | 3 | 3 | 0 | 0 | 0 | 0 | 11 |
| Combo 2 V3 | 0 | 0 | −1 | 2 | 0 | 0 | 0 | 0 | 9 |
| Combo 2 V4 | −1 | 0 | −1 | 2 | −1 | 0 | −1 | 0 | 4 |
| Combo 2 V6 | 0 | 0 | −1 | 2 | −1 | 0 | 0 | 0 | 4 |
| Combo 2 V7 | 0 | 0 | −1 | 2 | −1 | 0 | 0 | 0 | 0 |
| Combo 2 V9 | 0 | 0 | 0 | 1 | 0 | 0 | 0 | 0 | 5 |
| Combo 2 V10 | 0 | 0 | 0 | 1 | 0 | 0 | 0 | 0 | −1 |
| Combo 2 V13* | 0 | 1 | 0 | 1 | 1 | 0 | 2 | 0 | 6 |
| Combo 2 V17 | 0 | 0 | 0 | 1 | 1 | 0 | 1 | 0 | 3 |
| Combo 2 V18 | 0 | 0 | 0 | 1 | 0 | 0 | 0 | 0 | 5 |
| Combo 3 V13* | 0 | 0 | 1 | −2 | 0 | 0 | 0 | 0 | 7 |
| Positive shear stress assay control | | | | | | | | | 86 |

*Stability for the constructs was assessed after incubation at 25 and 40° C. for only 2 weeks.

Results

All variants displayed excellent stability. Incubation at elevated temperatures in a non-optimized buffer (PBS) resulted only in minor degradation, <3% increase in aggregation and <3% increase in fragmentation as measured by SE-HPLC (Table 5), SDS-PAGE, dual ELISA, A280 and visual inspection, indicating a good storage stability. In addition, freeze/thawing treatments of 1 or 3 rounds showed minimal degradation as measured by SE-HPLC, indicating again that the stability of the construct is high. Shear stress stability studies showed low loss of protein (<20%) after severe agitation for all of the tested constructs (Table 5) indicating that the bsAb are not sensitive to shear stress. Evaluation of the colloidal stability showed to reach 50% loss of the protein concentrations >9% of PEG were required (FIG. 2), which indicates that all tested constructs have good colloidal stability. Further, in a study to evaluate the sensitivity to low pH, constructs were incubated at pH 3.5 either during protein A elution or after elution and eluate neutralization.

The melting temperatures measured with UNcle were found to be >64° C. for Combo 2 constructs (CD40-EpCAM

TABLE 6

Melting temperatures determined with Uncle.

| bsAb | Tm (° C.) |
|---|---|
| Combo 1 v2 | 70 |
| Combo 1 v3 | 69 |
| Combo 1 v4 | 69 |
| Combo 1 v5 | 72 |
| Combo 1 v6 | 70 |
| Combo 1 v7 | 70 |
| Combo 1 v8 | 69 |
| Combo 1 v9' | 69 |
| Combo 1 v10 | 67 |
| Combo 1 v13 | 68 |
| Combo 1 v17 | 70 |
| Combo 1 v18 | 70 |
| Combo 2 v3 | 66 |
| Combo 2 v4 | 68 |
| Combo 2 v6 | 66 |
| Combo 2 v7 | 68 |
| Combo 2 v9 | 66 |
| Combo 2 v10 | 68 |
| Combo 2 v13 | 65 |

TABLE 6-continued

| Melting temperatures determined with Uncle. | |
| --- | --- |
| bsAb | Tm (° C.) |
| Combo 2 v17 | 64 |
| Combo 2 v18 | 66 |

Example 3—Binding Studies

Material and Methods

Dual ELISA

Plates were coated with 0.5 µg/mL antigen, Ag1 or Ag2, in PBS over night at 4° C. After washing in PBS/0.05% Tween 20 (PBST), the plates were blocked with PBS/2% BSA for at least 30 minutes at room temperature before being washed again. Samples serially diluted in PBS/0.5% BSA were then added and allowed to bind for at least 1 hour at room temperature. After washing, plates were incubated with 0.5 µg/mL biotinylated Ag1 or Ag2, whichever of the antigens that was not used for coating, for at least 1 hour at room temperature. Dual complexed bsAb with Ag1 and Ag2 were detected with HRP-labelled streptavidin. SuperSignal Pico Luminescent was used as substrate and luminescence signals were measured using Fluostar Optima.

Octet

Kinetic measurements were performed using the Octet RED96 platform (ForteBlo). Antigens, either biotinylated or Fc labelled, were coupled to either Streptavidin or Amine reactive Second generation sensors (ForteBio) at antigen concentrations of 0.4, 1.5, 0.25 or 0.5 µg/mL. Tested bsAb and mAbs (serially diluted ½ in 1×Kinetic buffer (ForteBio) with start concentrations of 20, 15, 10 or 25 nM) were analysed for binding to antigen-coupled sensors. The association was followed for 300, 1000 or 600 seconds and the dissociation in 1× Kinetic buffer for 1000, 2000, 600 or 300 seconds. Sensor tips were regenerated using 10 mM glycine, pH 2.2. Data generated were referenced by subtracting a parallel buffer blank, the baseline was aligned with the y-axis, inter-step correlation by alignment against dissociation was performed and the data were smoothed by a Savitzky-Golay filter in the data analysis software (v.9.0.0.14). The processed data were fitted using a 1:1 Langmuir binding model.

Results

Binding studies showed good binding to both targets for each combination as analysed by Octet and dual ELISA. Octet measurements showed similar KD values for the bsAb constructs in the new format compared to monoclonal or bispecific antibody controls (Table 7). In dual ELISA assays where simultaneous binding to each target combination was evaluated it was shown that indeed all novel bsAb constructs regardless of variant displayed dual binding. This was observed for bsAb constructs against different target combination as shown in representative ELISAs in FIG. 3.

TABLE 7

| Binding kinetics of bsAb and mAb constructs. | | | | |
| --- | --- | --- | --- | --- |
| Construct | Target | KD (nM) | kon (1/Ms) | kdis (1/s) |
| Combo 1 v6 | Combo 1 Ag1 | 0.02 | 4E+6 | 6E−5 |
| Combo 1 v9' | Combo 1 Ag1 | 0.02 | 3E+6 | 6E−5 |
| mAb Combo 1 Ag1 | Combo 1 Ag1 | 0.03 | 4E+6 | 1E−4 |

TABLE 7-continued

| Binding kinetics of bsAb and mAb constructs. | | | | |
| --- | --- | --- | --- | --- |
| Construct | Target | KD (nM) | kon (1/Ms) | kdis (1/s) |
| bsAb control Combo 1 | Combo 1 Ag1 | 0.03 | 3E+6 | 7E−5 |
| Combo 1 V6 | Combo 1 Ag2 | 0.2 | 1E+5 | 3E−5 |
| Combo 1 V9' | Combo 1 Ag2 | 1.0 | 7E+4 | 7E−5 |
| mAb Combo 1 Ag 2 | Combo 1 Ag2 | 0.2 | 5E+5 | 8E−5 |
| Combo 2 V9 | Combo 2 Ag1 | 1 | 1E+6 | 1E−3 |
| Combo 2 V10 | Combo 2 Ag1 | 1 | 1E+6 | 1E−3 |
| Combo 2 V19 | Combo 2 Ag1 | 2 | 7E+5 | 1E−3 |
| mAb Combo 2 Ag1 | Combo 2 Ag1 | 1 | 1E+6 | 1E−3 |
| bsAB control Combo 2 | Combo 2 Ag1 | 1 | 9E+5 | 7E−4 |
| Combo 2 V9 | Combo 2 Ag2 | 8 | 1E+5 | 1E−3 |
| Combo 2 V10 | Combo 2 Ag2 | 9 | 2E+5 | 2E−3 |

Example 4—Functional Assay T Cell Activation

Material and Methods

T Cell Activation Assay

The functional activity of the Combo 1 bsAbs (CD137-5T4 bispecific) was evaluated in a CD8+ T cell assay, where cells were cultured in microtiter plates coated with Combo 1 Ag2-Fc and CD3 antibody. Peripheral blood mononuclear cells (PBMC) were isolated by density gradient centrifugation using Ficoll-Paque (p 1.077 g/ml) (GE Healthcare #17-1440-02) from leucocyte concentrates obtained from healthy donors (Clinical Immunology and Transfusion Medicine, Labmedicin Region Skåne, Lund Sweden). CD8+ T cells were enriched by negative selection using the CD8+ T cell isolation kit (Miltenyi 130-096-495). Plates were coated overnight at 4° C. with 3 µg/ml αCD3, clone OKT3 (Affymetrix eBioscience #16-0037-85), washed and coated with 5 µg/ml 5T4-Fc for 2 h at 37° C. After the Ag2-Fc coating, plates were washed and blocked for a minimum of 30 minutes with RPMI (Gibco #61870010) containing 10% FCS (Heat inactivated, Gibco #10270-106 lot 41Q9248K) and 10 mM HEPES (Gibco #15630056). Combo 1 bsAbs (CD137-5T4 bispecific) bsAbs were diluted in RPMI containing 10% FCS and 10 mM HEPES and added to the plates 30 minutes before addition of CD8+ T cells (0.07×10^6 cells/well). Assay plates were incubated for 68 h at 37° C., and culture supernatant harvested. IFN-γ levels in the supernatants were measured by ELISA (ED OptiEIA #555142).

Results

Constructs were shown to have good T cell activation function. The functional activity of Combo 1 constructs (CD137-5T4 bispecific antibodies) was determined using human CD8+ T cells cultured in 5T4-Fc coated plates and was based on sets of experiments with a total of 4 donors for each set. CD8+ T cell activation of the bispecific antibodies was assessed both in the presence and absence of 5T4-Fc, to verify a 5T4 crosslinking dependency of CD137 activation. As shown in FIG. 5, the bispecific CD137-5T4 antibodies induced a high functional T cell activity with EC50 values ranging between 0.69-1.74 nM. Absolute mean IFN-γ values from one representative donor in the presence or absence of 5T4 is shown in FIG. 6. The results show that all CD137-5T4 targeting bispecific antibodies evaluated induced a potent T cell activation, measured by a dose-dependent increase in IFN-γ release in the presence of 5T4. In the absence of 5T4, there was no dose-dependent increase in T cell activity of the bispecific constructs.

Example 5—B Cell Activation Function

Material and Methods

B Cell Activation Assay

Transfected CHO cells expressing Combo 2 (CD40-Ep-CAM bispecific) Ag2 and CHO cells transfected with an empty vector were UV irradiated, seeded in 96-well flat-bottom tissue culture-treated plates and incubated at 37° C. overnight. PBMCs were isolated from healthy donors as described above. B cells were enriched using human B cell isolation kit II (Miltenyi Biotec) and cultured with the irradiated CHO-Ag2 or CHO-ctrl cells and Combo 2 bsAbs in RPMI 1640 (Gibco) supplemented with 10% FCS, 10 mM HEPES (Gibco) and ng/ml IL-4 (Gibco). After 48 h, cells were harvested and stained with CD19-PE-Cy7, CD86-APC and Fixable Viability Stain 450 (all ED Biosciences). Expression of CD86 on CD19+ B cells was analyzed by flow cytometry.

Results

As shown in FIG. 7, all tested Combo 2 constructs (CD40-EpCAM bispecific) induced a dose-dependent B cell activation in the presence of Combo 2 Ag2 (EpCAM) as measured by upregulation of the costimulatory molecule CD86. Little or no B cell activation was seen in the absence of Combo 2 Ag2 (EpCAM), indicating that B cell activation is crosslinking-dependent, requiring the presence of Combo 2 Ag2 (EpCAM).

Example 6—Dendritic Cell Activation Function

Material and Methods

DC Activation Assay

PBMCs were isolated as described above. Monocytes were enriched by positive selection using CD14 microbeads (Miltenyi Biotec) and cultured in the presence of GM-CSF (150 ng/ml, Gibco) and IL-4 (50 ng/ml, Gibco) for 7 days to generate monocyte-derived DCs. Transfected CHO cells expressing Combo 2 (CD40-EpCAM bispecific) Ag2 and CHO cells transfected with an empty vector were UV irradiated, seeded in 96-well flat-bottom tissue culture-treated plates and incubated at 37° C. overnight. DCs were cocultured with CHO-Ag2 or CHO-ctrl cells and Combo 2 bsAbs in medium supplemented with GM-CSF and IL-4 for 48 h, followed by flow cytometry analysis of CD86 and HLA-DR expression on DCs.

Results

Both Combo 2 constructs (CD40-EpCAM bispecific) variant 9 and variant 10 (v9 and v10 respectively) induced dose-dependent DC activation in the presence but not absence of Combo 2 Ag2 (EpCAM), measured as % of CD86+ HLA-DR+ cells among CD1a+ CD14− DCs (FIG. 8).

Example 7—Internalization Function

Material and Methods

A tumor cell line expressing Combo 2 (CD40-EpCAM bispecific) Ag2 was stained with the fluorescent membrane dye PKH26 (Sigma-Aldrich) followed by heat shock at 45° C. for 10 min to induce cell death. Heat-shocked tumor cells were incubated at 37° C. overnight, spun down and supernatant containing tumor cell debris was collected. Raji cells were labelled with the nuclear stain Hoechst 33342 (0.045 μg/ml, Thermo Fisher) and seeded in 96-well flat-bottom plates (Costar). Tumor cell debris and Combo 2 bsAbs or control mAb were added, and cells were imaged using Cytation5 (BioTek) every hour. Gen5 software was used to analyse the number of colocalized tumor debris and Raji cells.

Results

Combo 2 constructs (CD40-EpCAM bispecific) were shown to induce internalization of tumour cell debris. A CD40-expressing cell line was incubated with fluorescently cell debris from a necrotic tumour cell line expressing Combo 2 Ag2. Different Combo 2 bsAbs or a control mAb were added, and the localization of tumour cell debris in CD40+ cells was analysed using a live cell imaging system. All bispecific constructs enhanced internalization of tumour debris in a dose-dependent manner (FIG. 9).

Example 8—Fc Gamma Receptor Interaction Measured by Octet

Material and Methods

Binding towards soluble human and mouse Fcγ receptors (FcγR) of either novel IgG-Fab bsAb constructs with different Fc isotype variants or monoclonal isotype controls were evaluated using the Octet RED96 platform (ForteBlo). Samples consisting of variant 9 IgG-Fab bsAb constructs carrying IgG1, IgG1 LALA, IgG2 or IgG4 S228P Fc domains were diluted in 200 nM 1× Kinetic buffer and captured on 8 parallel sensors for 300 seconds. After setting a new baseline, the captured antibodies were assayed against any of the FcγR (hFcγRI (1257-FC-050, R&D Systems), hFcγRIIa (1330-CD-050, R&D Systems), hFcγRIIb (1875-CD-050, R&D Systems), hFcγRIIIa (4325-FC-050, R&D Systems), hFcγRIIIa V176F (8894-FC-050, R&D Systems), mFcγRI (2074-FC-050, R&D Systems), mFcγRIIb (1460-CD-050, R&D Systems), mFcγRIII (1960-FC-050, R&D Systems) mFcγRIV (50036-M27H-50, Sino Biologicals) for 60 seconds followed by dissociation for 60 seconds in Kinetic buffer. The FcgRs were ran in seven 1:2 dilutions starting at 100 nM. Sensor regeneration using 10 mM Glycine pH 1.7 was performed before capturing of the next bsAb/mAb. Data generated were referenced by subtracting a parallel buffer blank, the baseline was aligned with the y-axis, inter-step correlation by alignment against dissociation was performed and the data were smoothed by a Savitzky-Golay filter in the data analysis software (v.9.0.0.14). The processed data were fitted using a 1:1 Langmuir binding model.

Results

Octet measurement show similar Fcγ receptor interaction for novel bsAb constructs compared to mAb isotype controls regardless of Fc isotype as demonstrated by similar measured affinities as shown in FIG. 10 of representative chromatograms and as listed in Table 8. This indicates that the novel IgG-Fab bsAb constructs can engage Fc gamma receptors and may also have similar Fc functions compare to natural antibodies.

TABLE 8

Octet measurements of Fcgamma receptor interaction with novel constructs compared to monoclonal antibodies

| Construct | hFcgRI | | | hFcgRIIa | | | hFcγRIIIa 176V | | |
|---|---|---|---|---|---|---|---|---|---|
| | $K_D$ (M) | $K_{on}$ (1/Ms) | $K_{dis}$ (1/s) | $K_D$ (M) | $K_{on}$ (1/Ms) | $K_{dis}$ (1/s) | $K_D$ (M) | $K_{on}$ (1/Ms) | $K_{dis}$ (1/s) |
| IgG1 bsAb | <1E-12 | 5E+05 | <1E-07 | 2E-07 | 2E+06 | 4E-01 | 3E-08 | 1E+06 | 3E-02 |
| IgG1 mAb | <1E-12 | 3E+05 | <1E-07 | 3E-07 | 1E+06 | 4E-01 | 5E-08 | 6E+05 | 3E-02 |
| IgG1 LALA bsAb | 4E-08 | 7E+05 | 3E-02 | <LOD | <LOD | <LOD | <LOD | <LOD | <LOD |
| IgG1 LALA mAb | 5E-08 | 5E+05 | 2E-02 | <LOD | <LOD | <LOD | <LOD | <LOD | <LOD |
| IgG4 bsAb | 3E-09 | 8E+05 | 2E-03 | <LOD | <LOD | <LOD | <LOD | <LOD | <LOD |
| IgG4 mAb | 2E-09 | 7E+05 | 1E-03 | <LOD | <LOD | <LOD | <LOD | <LOD | <LOD |
| IgG2 bsAb | <LOD | <LOD | <LOD | <LOD | <LOD | <LOD | <LOD | <LOD | <LOD |
| IgG2 mAb | <LOD | <LOD | <LOD | <LOD | <LOD | <LOD | <LOD | <LOD | <LOD |

Example 9—Interaction to Fc Gamma Receptors Expressed on Cells Measured by FACS

Material and Methods

CHO K1 cells (ATCC) transfected with FcγRI, FcγRIIa (R131), FcγRIIa (H131) and FcγRIIb were used, as a pool or single cell sorted, for the analysis of binding of novel bispecific antibody constructs with different Fc isotypes to the above mentioned Fcγ receptors using flow cytometry. Cells were incubated with variant 9 IgG-Fab bsAb constructs carrying IgG1, IgG1 LALA or IgG2 Fc domains or a monoclonal isotype controls (at 50, 10, 2 or 0.4 μg/mL), followed by secondary staining with PE-conjugated goat anti-human IgG (F(ab')2) antibody (Jackson ImmunoResearch Inc. PA, US). Cells were analyzed using a FACS-Verse™ (BD Biosciences, US), and data was analyzed using the FlowJo software (BD Bioscience).

Results

Results from repeated studies show that novel bsAb contructs of different isotypes bind to Fc gamma receptors expressed on cells in a similar manner as is observed for monoclonal antibodies. Experiments with hFcγRI expressing cells shows dose dependent response with IgG1 RUBYs and IgG1 mAb. Neither RUBYs with IgG1 LALA or IgG2 nor monoclonal antibodies with these isotypes appear to interact with these cells as expected and shown in FIG. 11. This demonstrates that the bsAbs constructs can engage Fc gamma receptors and have likely retained Fc gamma receptor functions.

Example 10—IgG Like bsAb

Material and Methods

Design

To evaluate if the combination of mutations found to be beneficial for the generation of functional and developable IgG-Fab bispecific antibody constructs could also be used to promote correct chain pairing in other bispecific antibody architectures, constructs containing the combination of mutations in variants 9 (or 9'), 13, and 19 were generated in an IgG like architecture. These were compared to variant 1 IgG like bsAbs. Using Knob-in-Hole mutations, IgG like bsAbs of variants 1, 9', 13, and 19 were generated for Combo 1 constructs (CD137-5T4 bispecific) and variants 1, 9, 13, and 19 for Combo 2 constructs (CD40-EpCAM bispecific).

Production of IgG like bsAbs. Bispecific antibodies were expressed using transient Expi293 HEK (Life technologies) cultures at 30 mL according to manufacturer's instructions. Purification of bispecifics from supernatants was made on protein A using the NGC system (BioRad). Cells were transfected with four different vectors encoding separately for each of the four polypeptides chains (i.e. the immunoglobulin heavy chain of a first antibody carrying also the Knob mutations, the immunoglobulin heavy chain of a second antibody, the immunoglobulin light chain the first antibody and the immunoglobulin light chain of the second antibody). The same transfection ratio (non-optimized) was used for all constructs.

ELISA

IgG like bsAb were analyzed in dual ELISA to investigate binding differences that can indicate differences in amount of light chain mispairing. Plates were coated with 0.5 μg/mL antigen Ag1 in PBS over night at 4° C. After washing in PBS/0.05% Tween 20 (PBST), the plates were blocked with PBS/2% BSA for at least 30 minutes at room temperature before being washed again. Samples serially diluted in PBS/0.5% BSA were then added and allowed to bind for at least 1 hour at room temperature. After washing, plates were incubated with 0.5 μg/mL biotinylated Ag2 for at least 1 hour at room temperature. Dual complexed bsAb with Ag1 and Ag2 were detected with HRP-labelled streptavidin. SuperSignal Pico Luminescent was used as substrate and luminescence signals were measured using Fluostar Optima.

Generation of Fab Fragments

To be able to analyse amount of light chain mispairing with ESI-LC-MS purified Fab fragments from IgG like bsAbs were generated using the GingisKHAN Fab kit (Genovis, B0-GFK-020) under manufacturer's recommended conditions. The kit mainly involves two steps, GingisKHAN digestion of IgG and purification of the fragments on an IgG-CH1 specific affinity spin column. Briefly, 2000 U GingisKHAN was reconstituted in 200 μL ddH2O, and the 10× reducing agent (supplied by the vendor) was freshly prepared in 50 μL ddH2O before each digestion. 150 μg antibody in 100 mM Tris, pH 8.0 were digested with the reconstituted GingisKHAN and freshly prepared 10× reducing agent at 37° C. for 1 hour. The digests were analyzed by SE-HPLC and LC-ESI-MS.

Molecular Weight Determination with LC-ESI-MS

Determination of the Molecular Weight (MW) of intact proteins was performed by Liquid Chromatography coupled to Electrospray Ionization Mass Spectrometry (LC-ESI-MS). LC-measurement were made with an Agilent 1200 system (Agilent, Santa Clara, CA). A; Poroshell 300SB-C8

2.1×75 mm, 5 μm column (Agilent) was used for chromatographic separation. Mobile phases A and B were 0.1% TFA in water and acetonitrile, respectively. Mass spectra were collected with a maXis Impact mass spectrometer (Bruker Daltonics, Germany) at a mass-to-charge ratio range of 500-4500. Molecular mass was determined by deconvolution of the mass spectra data using the MaxEnt I software package. The determined MW was compared to the theoretical MW calculated from the protein amino acid sequence.

Results

Dual ELISA demonstrates higher binding for constructs carrying combination of mutations compare to constructs without mutations to promote correct light chain pairing. As shown in FIG. 12 variant 1 IgG-like construct gives much lower luminescence signals compared to all other three tested IgG-like variants (variant 9, 13 and 19). Variant 1 construct does not carry any mutations to promote correct light chain pairing. The amount of wrongly paired light chains of the variant 1 sample is likely high (in theory 50% of the sample can be mispaired) and wrongly paired products could have lower binding. Since higher binding is elicited by variant 9, 13 and 19 constructs this demonstrates that the combination of mutations are beneficial and indicates that these combinations of mutations are advantageous for correct chain pairing not only for the IgG-Fab architecture but also for IgG like architecture.

Further, mass spectrometry analysis was used to detect the amount of correctly paired light chains. Samples of Fab fragments generated by enzymatic cleavage from IgG-like bsAb constructs and purified on CH1 columns were tested on LC-ESI-MS. Determined masses were compared with theoretical molecular weight values. Results show the mutations can greatly improve correct pairing of heavy and light chains. As observed in Table 10 the amount of mis-paired Fab species in the samples from IgG-like bsAb with no mutations (variant 1 constructs) is as expected very high (close to 50% for Combo 2 construct). The variant 19 mutations decrease the amount of mispaired Fab species substantially to as little as 6% (for the Combo 1 construct). In all, this demonstrates that the combination of mutations discovered for IgG-Fab bispecific may be beneficial in the generation of other bispecific antibody of other architectures as well, as observed for IgG-like bsAb in this example.

TABLE 10

Relative amount of correctly paired and mispaired Fab fragment species in Combo 1 and Combo 2 variants 1 and 19.

| | Relative amount (%) of correctly paired Fab species | Relative amount (%) of mispaired Fab species |
|---|---|---|
| Combo 1 variant 1 | 63 | 38 |
| Combo 1 variant 19 | 94 | 6 |
| Combo 2 variant 1 | 53 | 47 |
| Combo 2 variant 19 | 92 | 8 |

Example 11—BsAbs with Truncated Light Chain

Material and Methods

Design

To evaluate if the linker position could be moved in the IgG-Fab constructs bispecific antibodies with truncated Fab fragments fused to the C terminal end of IgGs were also engineered. Variants with differently truncated Fabs were included in the study. The truncation was made in the N-terminal end of the Fab fragment by deleting nucleotides coding for the first 3 (variant 21), 6 (variant 22) or 9 (variant 23) amino acids of the light chain of variant 9 IgG-Fab bsAb constructs.

Thermostability

The melting temperatures were measured with the UNcle system (UNchained labs). The intrinsic fluorescence was measured during linear temperature ramping from 20° C. to 95° C. at a rate of 0.4° C./minute. The data analysis was performed with the UNcle Analysis software version 2.0 using default settings.

Stability

Samples in non-optimized buffer (PBS) at low (<1 mg/mL) were incubated at 2-8° C., room temperature and 40° C. 2 weeks or subjected to 3 rounds of freeze thawing. Protein degradation was measured with SE-HPLC, SDS-PAGE, A280, dual ELISA and by visual inspection.

Shear Stress Stability

Samples in duplicates were subjected to shear stress in the form of heavy agitation at 2000 rpm on the 96-well plate shaker MixMate (Eppendorf) for at least 30 minutes. Protein precipitates were removed by centrifugation at 3000 g for 10 minutes and the absorbance at 280 nm was measured using Big Lunatic.

Colloidal Stability

Samples were mixed with PBS/PEG solutions with different PEG concentrations ranging from 8%-36%, added to 96-well filter plates in triplicates and incubated over night at room temperature. Filtrates obtained by centrifugation at 12000 g for 15 minutes were collected and spun down before the absorbance at 280 nm was measured (to determine loss of protein) and compared to controls.

Production and Manufacturing

Bispecific antibodies were expressed using transient Expi293 HEK (Life technologies) cultures at different volumes ranging from high through put to 30 mL according to manufacturer's instructions. Purification of bispecifics from supernatants was made on protein A using the NGC system (BioRad), the AKTA Avant system (GE Healthcare) or Predictor MabSelectSure 50 μl 96 well plates (GE Healthcare). Cells were transfected with three different vectors encoding separately for each of the three polypeptides chains (i.e. the immunoglobulin heavy chain linked to the Fab light chain, the immunoglobulin light chain and the Fab heavy chain). Aggregation was measured with SE-HPLC in a 1260 Infinity II system (Agilent Technologies) using a TSK gel Super SW mAB HTP 4 μm, 4.6×150 mm column (TOSOH Bioscience) and 100 mM Sodium Phosphate, pH 6.8, 300 mM NaCl as mobile phase at ambient temperature and a flow rate of 0.35 ml/min.

Dual ELISA

Plates were coated with 0.5 μg/mL antigen Ag1 in PBS over night at 4° C. After washing in PBS/0.05% Tween 20 (PBST), the plates were blocked with PBS/2% BSA for at least 30 minutes at room temperature before being washed again. Samples serially diluted in PBS/0.5% BSA were then added and allowed to bind for at least 1 hour at room temperature. After washing, plates were incubated with 0.5 μg/mL biotinylated Ag2 for at least 1 hour at room temperature. Dual complexed bsAb with Ag1 and Ag2 were detected with HRP-labelled streptavidin. SuperSignal Pico Luminescent was used as substrate and luminescence signals were measured using Fluostar Optima.

Results

The expression yields of constructs varied substantially depending of the combination of IgG and Fab domains. Combo 1 constructs could be expressed regardless of truncation variant.

Binding tested in dual ELISA with variant 21 and 22 constructs showed that variant 21 constructs display higher target interaction as observed in FIG. 13.

Further, the developability of variant 21 constructs was evaluated. All variants displayed high stability. Incubation at elevated temperatures in a non-optimized buffer (PBS) resulted only in low degradation, <10% increase in aggregation and <5% increase in fragmentation as measured by SE-HPLC (Table 12), SDS-PAGE, dual ELISA, A280 and visual inspection, indicating a good storage stability. In addition, freeze/thawing treatments of 1 or 3 rounds showed minimal degradation <3% degradation as measured by SE-HPLC, indicating again that the stability of the constructs is high.

Shear stress stability studies showed low loss of protein (<25%) after severe agitation for all of the tested constructs (Table 11 indicating that the bsAb are not sensitive to shear stress. Evaluation of the colloidal stability showed to reach 50% loss of the protein concentrations >9% of PEG were required (FIG. 13), which indicates that all tested constructs have good colloidal stability.

The melting temperatures measured with UNcle were found to be >65° C. for the variant 21 constructs as shown in Table 13 indicating that the thermostability of these constructs is high.

In all the experiments with truncated light chains show that removal of some amino acids, in particular 3 as in variant 21, results in constructs that are both stable and display excellent binding. Furthermore, this strategy was shown to be compatible with variant 9 combination of mutations and will likely work with other IgG-Fab bsAb variants.

TABLE 11

| Expression yields for Combo 1 (5T4-CD137 bispecific) variants 21, 22 and 23 | |
| --- | --- |
| Combo ID | Yield(mg/L) |
| Combo 1 v21 | 127 |
| Combo 1 v22 | 85 |
| Combo 1 v23 | 144 |

TABKE 12

| | 25 C., 2 weeks | | 40 C., 2 weeks | | Freeze/thaw, 1 round | | Freeze/thaw, 3 rounds | | Protein loss % after shear |
| --- | --- | --- | --- | --- | --- | --- | --- | --- | --- |
| bsAb | Δ % HMWs | Δ % LMWs | Δ % HMWs | Δ % LMWs | Δ % HMWs | Δ % LMWs | Δ % HMWs | Δ % LMWs | stress treatment |
| Combo 1 V21 | 1.7 | −0.1 | 9.5 | 0.7 | 0.1 | 0.2 | 0.8 | −0.1 | 22.2 |

Changes in degradation after different treatments to evaluate stability.

96

TABLE 13

| Melting temperatures determined with Uncle. | |
| --- | --- |
| Construct | Tm (° C.) |
| Combo 1 v21 | 67 |

Example 12—Strategy to Remove Protein a Site in Unwanted Fab by-Products

Material and Methods

Design

To investigate if the protein A purification of unwanted Fab by-product, could be decreased, mutations at position 65, which is close to the protein A site for variable heavy chains of framework group IGHV3, were introduced. Constructs with mutations T65E or T65A in the variable FAb heavy chain were compared with constructs without mutations in this position Production Bispecific antibodies were expressed using transient Expi293 HEK (Life technologies) cultures in 700 μl according to manufacturer's instructions. Purification of bispecifics from supernatants was made on protein A Predictor Mab-SelectSure 50 μl 96 well plates (GE Healthcare). Cells were transfected with three different vectors encoding separately for each of the three polypeptides chains (i.e. the immunoglobulin heavy chain linked to the Fab light chain, the immunoglobulin light chain and the Fab heavy chain).

HPLC Analysis

Aggregation was measured with SE-HPLC in a 1260 Infinity II system (Agilent Technologies) using a TSK gel Super SW mAB HTP 4 μm, 4.6×150 mm column (TOSOH Bioscience) and 100 mM Sodium Phosphate, pH 6.8, 300 mM NaCl as mobile phase at ambient temperature and a flow rate of 0.35 ml/min.

Results

Mutations in position 65 showed improved purity after protein A purification as observed from HPLC measurements. The investigated mutations were shown to decrease the amount of purified Fab substantially with close to 100% reduction of amount of purified Fab in the majority of tested constructs (Table 14)

TABLE 14

Relative reduction of amount (%) of
by-product FAb after protein A purification
compared to constructs with no mutation in position 65.

| BsAb construct | Reduction of amount of by-product FAb after protein A purification compared to constructs with no mutation in position 65 (%) |
|---|---|
| Combo 4, V9 T65E | 88 |
| Combo 4, V9 T65A | 96 |
| Combo 5, V9 T65E | 98 |
| Combo 5, V9 T65A | 98 |

Example 13: Anti-Tumour Effect of the Combo 2 Variant 9 (CD40-EpCAM) Bispecific Antibody (Also Known as 1132-3174.R in RUBY™ Format)

Background and Aim 1132-3174.R is a CD40-EpCAM bispecific antibody in the novel IgG-Fab bispecific format (as described herein) wherein 1132 refers to its CD40 agonist domain and 3174 to its EpCAM-binding, tumour-targeting domain. The antibody has been LALA-mutated to silence Fcγ receptor binding.

The aim of this study was to evaluate the anti-tumour effect of 1132-3174.R in human CD40 transgenic (hCD40tg) mice inoculated with murine MB49 tumours transfected with human EpCAM (MB49-hEpCAM) or MB49-wt (hEp-CAM negative) tumours.

Materials and Methods

Female hCD40tg mice of 13-16 weeks of age were inoculated with either $2.5 \times 10^5$ MB49-wt or MB49-hEp-CAM cells s.c. in the right flank. On days 10, 13 and 16 after inoculation, the mice were administered i.p. with 100 μg of wildtype CD40 monospecific antibody, 1132, or 250 μg of the LALA-mutated equivalent, 1132.m2. Alternatively, the mice received 417 μg of 1132-3174.R. A group of vehicle-treated mice was also included. The tumours were frequently measured with a caliper in width (w), length (1) and height (h) and the tumour volume was calculated using the formula: $(w/2 \times l/2 \times h/2 \times \pi \times (4/3))$.

In an alternative experimental set-up, hCD40tg mice were inoculated with MB49-wt or MB49-hEpCAM cells s.c. as previously and, instead, mice were administered i.p. with 100 μg 1132, 100 μg 1132.m2 or 167 μg (dose of molecular mass equivalence to the monospecific antibodies) or 417 μg (dose 2.5 fold higher in terms of molecular mass, compared to monospecific antibodies) 1132-3174.R on days 10, 13 and 16 after inoculation. A group of vehicle-treated mice was also included. Tumours were frequently measured as previously.

Results

The data (shown in FIG. 15) demonstrate that treatment with 1132-3174.R significantly reduces the tumour volume compared to vehicle-treated mice, as well as mice treated with 1132. Additionally, in mice bearing MB49-wt tumours administered the same dosage of 1132-3174.R, the anti-tumour effect of 1132-3174.R is almost completely diminished. Thus, 1132-3174.R has a potent, EpCAM-dependent anti-tumour effect in the MB49 tumour model.

Example 14: Anti-Tumour Effect of Combo 2 Variant (CD40-EpCAM) Bispecific Antibody (Also Known as 1132-3174.R)

Background and Aim 1132-3174.R is a CD40-EpCAM bispecific antibody in the novel IgG-Fab bispecific format (as described herein) wherein 1132 refers to its CD40 agonist domain and 3174 to its EpCAM-binding, tumour-targeting domain. The antibody has been LALA-mutated to silence Fcγ receptor binding.

The aim of this study was to evaluate the anti-tumour effect of 1132-3174.R in human CD40 transgenic (hCD40tg) mice inoculated with murine MB49 tumours transfected with human EpCAM (MB49-hEpCAM) or MB49-wt (hEp-CAM negative) tumours.

Materials and Methods

Female hCD40tg mice of 13-16 weeks of age were inoculated with either 2.5×105 MB49-wt or MB49-hEp-CAM cells s.c. in the right flank. On days 10, 13 and 16 after inoculation, the mice were administered i.p. with 100 μg of wildtype CD40 monospecific antibody 1132 or 100 μg of the LALA-mutated equivalent 1132.m2. Alternatively, the mice received 167 μg 1132-3174.R (dose of molecular mass equivalence to the monospecific antibodies) or 417 μg 1132-3174.R (dose 2.5 fold higher in terms of molecular mass, compared to monospecific antibodies). A group of vehicle-treated mice was also included. The mice were kept in the study until the individual tumour volume reached the ethical limit of 2000 mm3, at which point the mice were sacrificed.

Results and Conclusions

The data (shown in FIG. 16) demonstrate that treatment with 1132-3174.R significantly improves the survival compared to vehicle-treated mice, as well as mice treated with a molecular mass equivalent dose of 1132. A 2.5-fold higher dose of 1132-3174.R results in complete tumour eradication, and 100% survival of the mice. Additionally, in mice bearing MB49-wt tumours administered the same high dose of 1132-3174.R, the anti-tumour effect of 1132-3174.R is completely diminished. Thus, 1132-3174.R has a potent, EpCAM-dependent anti-tumour effect in the MB49 tumour model.

The invention is further defined by the following numbered paragraphs:

1. A bispecific antibody comprising:
   (a) an immunoglobulin molecule having specificity for a first antigen, the immunoglobulin molecule comprising a first heavy chain polypeptide and a first light chain polypeptide; and
   (b) at least one Fab fragment having specificity for a second antigen, the Fab fragment comprising a second heavy chain polypeptide and a second light chain polypeptide
   wherein the second light chain polypeptide is fused to the C-terminus of the first heavy chain polypeptide
   and wherein the bispecific antibody comprises one or more mutations to promote association of the first heavy chain polypeptide with the first light chain polypeptide and/or to promote association of the second heavy chain polypeptide with the second light chain polypeptide.

2. A bispecific antibody according to paragraph 1, wherein the immunoglobulin molecule comprises two copies of the first heavy chain polypeptide and/or two copies of the first light chain polypeptide.

3. A bispecific antibody according to paragraph 1 or 2, wherein the antibody comprises two Fab fragments according to (b).

4. A bispecific antibody according to any one of the preceding paragraphs, wherein the immunoglobulin molecule comprises two copies of the first heavy chain polypeptide and two copies of the first light chain polypeptide, and the bispecific antibody further comprises two Fab fragments according to (b), and the first Fab fragment is fused to the C-terminus of the first copy of the first heavy chain polypeptide via the light chain polypeptide of the Fab fragment; and the second Fab fragment is fused to the C-terminus of the second copy of the first heavy chain polypeptide via the light chain polypeptide of the Fab fragment.

5. A bispecific antibody according to any one of the preceding paragraphs, wherein the immunoglobulin molecule comprises a human Fc region or a variant of a said region, where the region is an IgG1, IgG2, IgG3 or IgG4 region, preferably an IgG1 or IgG4 region.

6. A bispecific antibody according to paragraph 5 wherein the Fc region is a naturally occurring (i.e. wildtype) human Fc region.

7. A bispecific antibody according to paragraph 5 wherein the Fc region is a non-naturally occurring (e.g. mutated) human Fc region.

8. A bispecific antibody according to any one of paragraphs 5 to 7 wherein the Fc region has modified glycosylation, for example wherein the Fc region is afucosylated.

9. A bispecific antibody according to any one of the preceding paragraphs wherein the one or more mutations are in one or more of the following regions:
   (i) the CH1 region of the first heavy chain polypeptide and/or
   (ii) the VH region of the first heavy chain polypeptide, and/or
   (iii) the CH1 region of the second heavy chain polypeptide and/or
   (iv) the VH region of the second heavy chain polypeptide, and/or
   (v) the CKappa or CLambda region of the first light chain polypeptide and/or
   (vi) the VL region of the first light chain polypeptide, and/or
   (vii) the CKappa or CLambda region of the second light chain polypeptide, and/or
   (viii) the VL region of the second light chain polypeptide.

10. A bispecific antibody according to any one of the preceding paragraphs wherein the one or more mutations prevent the binding of the second heavy chain polypeptide to the first light chain polypeptide and/or prevent self-aggregation of the first heavy chain polypeptide fused to the second light chain polypeptide.

11. A bispecific antibody according to any one of the preceding paragraphs wherein the one or more mutations prevent the formation of aggregates and a Fab by-product.

12. A bispecific antibody according to any one of the preceding paragraphs, wherein the mutations prevent formation of aggregates by generating steric hindrance and/or incompatibility between charges.

13. A bispecific antibody according to any one of the preceding paragraphs, wherein the mutations prevent for-mation of a Fab by-product by generating steric hindrance and/or incompatibility between charges.

14. A bispecific antibody according to any one of the preceding paragraphs wherein the antibody comprises one or more mutation pairs each comprising two functionally compatible mutations.

15. A bispecific antibody according to paragraph 14, wherein the functionally compatible mutations are selected from:
   (a) cavity and protruding surface mutations (i.e. steric mutations); and/or
   (b) hydrophobic swap mutations; and/or
   (c) charged mutations (i.e. salt mutations); and/or
   (d) double charged mutations; and/or
   (e) mutations resulting in the formation of a disulphide bridge.

16. A bispecific antibody according to paragraph 15, wherein the bispecific antibody comprises one or more mutation pairs in one or more of the following region groups:
   (a) the CH1 and CKappa or CLambda region of the immunoglobulin; and/or
   (b) the CH1 and CKappa or CLambda region of the Fab; and/or
   (c) the VL and VH regions of the immunoglobulin; and/or
   (d) the VL and VH regions of the Fab.

17. A bispecific antibody according to paragraph 16 wherein the mutation pairs are in the CH1 and CKappa or CLambda regions of the Fab and/or the immunoglobulin, and wherein the mutation pairs are selected from:
   (a) cavity and protruding surface mutations (i.e. steric mutations); and/or
   (b) hydrophobic swap mutations; and/or
   (c) charged mutations (i.e. salt mutations); and/or
   (d) mutations resulting in the formation of a disulphide bridge.

18. A bispecific antibody according to any one of paragraphs 15 to 17 wherein the mutation pairs are in the VH and VL regions of the Fab and/or the immunoglobulin, and wherein the mutation pairs are selected from:
   (a) charged mutations (i.e. salt mutations); and/or
   (b) double charged mutations; and/or
   (c) mutations resulting in the formation of a disulphide bridge.

19. A bispecific antibody according to any one of paragraphs 16 to 18 wherein the bispecific antibody comprises one or more mutation pairs selected from:
   (a) steric mutations in the CH1 and CKappa or CLambda regions of the immunoglobulin;
   (b) steric mutations in the CH1 and CKappa or CLambda regions of the immunoglobulin, salt mutations in the VH and VL regions of the immunoglobulin, and salt mutations in the VH and VL regions of the Fab;
   (c) steric mutations in the CH1 and CKappa or CLambda regions of the immunoglobulin, salt mutations in the VH and VL regions of the immunoglobulin, salt mutations and disulphide bridge-forming mutations in the VH and VL regions of the Fab;
   (d) hydrophobic mutations in the CH1 and CKappa or CLambda regions of the immunoglobulin and salt mutations in the CH1 and CKappa or CLambda regions of the Fab;
   (e) hydrophobic mutations in the CH1 and CKappa or CLambda regions of the immunoglobulin, salt mutations in the VH and VL regions of the immunoglobulin, salt mutations in the CH1 and CKappa or CLambda regions of the Fab, and salt mutations in the VH and VL regions of the Fab;

(f) hydrophobic mutations in the CH1 and CKappa or CLambda regions of the immunoglobulin, salt mutations in the VH and VL regions of the immunoglobulin, salt mutations in the CH1 and CKappa or CLambda regions of the Fab, and salt mutations and disulphide bridge-forming mutations in the VH and VL regions of the Fab;

(g) disulphide bridge-forming mutations in the CH1 and CKappa or CLambda regions of the Fab;

(h) steric mutations in the CH1 and CKappa or CLambda regions of the immunoglobulin, salt mutations in the VH and VL regions of the immunoglobulin, salt mutations in the CH1 and CKappa or CLambda regions of the Fab, and salt mutations in the VH and VL regions of the Fab;

(i) steric mutations in the CH1 and CKappa or CLambda regions of the immunoglobulin, salt mutations in the VH and VL regions of the immunoglobulin, salt mutations in the CH1 and CKappa or CLambda regions of the Fab, and salt mutations and disulphide bridge-forming mutations in the VH and VL regions of the Fab;

(j) salt mutations in the CH1 and CKappa or CLambda regions of the immunoglobulin, salt mutations in the VH and VL regions of the immunoglobulin, steric mutations in the CH1 and CKappa or CLambda regions of the Fab, and salt mutations in the VH and VL regions of the Fab;

(k) salt mutations in the CH1 and CKappa or CLambda regions of the immunoglobulin, salt mutations in the VH and VL regions of the immunoglobulin, steric mutations in the CH1 and CKappa or CLambda regions of the Fab, and salt mutations and disulphide bridge-forming mutations in the VH and VL regions of the Fab;

(l) salt mutations in the VH and VL regions of the immunoglobulin, steric mutations in the CH1 and CKappa or CLambda regions of the Fab, and salt mutations in the VH and VL regions of the Fab;

(m) salt mutations in the VH and VL regions of the immunoglobulin, steric mutations in the CH1 and CKappa or CLambda regions of the Fab, and salt mutations and disulphide bridge-forming mutations in the VH and VL regions of the Fab;

(n) hydrophobic mutations in the CH1 and CKappa or CLambda regions of the immunoglobulin, salt mutations in the VH and VL regions of the immunoglobulin, steric mutations and salt mutations in the CH1 and CKappa or CLambda regions of the Fab, and salt mutations in the VH and VL regions of the Fab;

(o) hydrophobic mutations in the CH1 and CKappa or CLambda regions of the immunoglobulin, salt mutations in the VH and VL regions of the immunoglobulin, steric mutations and salt mutations in the CH1 and CKappa or CLambda regions of the Fab, and salt mutations and disulphide bridge forming mutations in the VH and VL regions of the Fab;

(p) steric mutations and salt mutations in the CH1 and CKappa or CLambda regions of the immunoglobulin, salt mutations in the VH and VL regions of the immunoglobulin, hydrophobic mutations in the CH1 and CKappa or CLambda regions of the Fab, and salt mutations in the VH and VL regions of the Fab; or (q) steric mutations and salt mutations in the CH1 and CKappa or CLambda regions of the immunoglobulin, salt mutations in the VH and VL regions of the immunoglobulin, hydrophobic mutations in the CH1 and CKappa or CLambda regions of the Fab, and salt mutations and disulphide bridge-forming mutations in the VH and VL regions of the Fab.

(r) steric mutations in the CH1 and CKappa or CLambda regions of the immunoglobulin, salt mutations in the VH and VL regions of the immunoglobulin, salt mutation in the CH1 and alanine mutation in the CKappa or CLambda regions of the Fab, and salt mutations in the VH and VL regions of the Fab;

20. A bispecific antibody according to any one of the preceding paragraphs, wherein the mutations are at positions selected from the group consisting of:

(a) one or more of the following positions in the CH1 domain: H168, F170, L145, S183 and T187 (according to EU numbering); and/or (b) a position selected from the one or more of the following position ranges in the CKappa or CLambda domain: position 132 to 138, position 173 to 179, position 130 to 136, position 111 to 117 and position 134 to 140 (according to Kabat numbering); and/or (c) a position selected from one or more of the following position ranges in the VL: position 41 to 47, position 117 to 123 and position 46 to 52 (according to IMGT numbering); and/or (d) a position selected from one or more of the following position ranges in the VH: position 41 to 47, position 46 to 52 and position 117 to 123 (according to IMGT numbering).

21. A bispecific antibody according to any one of the preceding paragraphs, wherein the mutations are at positions selected from the group consisting of:

(a) one or more of the following positions in the CH1 domain: H168, F170, L145, S183 and T187 (according to EU numbering); and/or (b) one or more of the following positions in the CKappa or CLambda domain: 135, 176, 133, 114 and 137 (according to Kabat numbering); and/or (c) one or more of the following positions in the VL: 44, 120 and 49 (according to IMGT numbering); and/or (d) one or more of the following positions in the VH: 44, 49 and 120 (according to IMGT numbering).

22. A bispecific antibody according to any one of the preceding paragraphs, wherein the mutations are at positions selected from the group consisting of:

(a) one or more of the following positions in the CH1 domain: H168, F170, L145, S183 and T187 (according to EU numbering); and/or (b) one or more of the following positions in the CKappa or CLambda domain: L135, S176, V133, S114 and N137 (according to Kabat numbering); and/or (c) one or more of the following positions in the VL: Q44, Q120 or A120 and A49 (according to IMGT numbering); and/or (d) one or more of the following positions in the VH: Q44, G49 and Q120 (according to IMGT numbering).

23. A bispecific antibody according to paragraph 22, wherein the mutations are selected from the group consisting of:

(a) one or more of the following mutations in the CH1 domain: H168A, F170G, L145Q, S183V and T187E (according to EU numbering); and/or (b) one or more of the following mutations in the CKappa or CLambda domain: L135Y, S176W, V133T, S176V, S114A and N137K (according to Kabat numbering); and/or (c) one or more of the following mutations in the VL: Q44R, Q44E, Q120C or A120C, Q44D and A49D (according to IMGT numbering); and/or (d) one or more of the following mutations in the VH: Q44E, Q44R, G49C, Q44K and Q120K (according to IMGT numbering).

24. A bispecific antibody according to any one of the preceding paragraphs, wherein the bispecific antibody is tetravalent, with dual binding to each of the two antigens.

25. A bispecific antibody according to any one of the preceding paragraphs, wherein the Fab fragment(s) is linked to the C terminal end of the immunoglobulin via a linker.

26. A bispecific antibody according to paragraph 25, wherein the linker is a peptide with the amino acid sequence SGGGGSGGGGS (SEQ ID NO: 5), SGGGGSGGGGSAP (SEQ ID NO: 6), NFSQP (SEQ ID NO: 7), KRTVA (SEQ ID NO: 8), GGGGSGGGGSGGGGS (SEQ ID NO: 9), (SG)m, where m=1 to 7 or GGGGSGGGGS (SEQ ID NO: 34).

27. A bispecific antibody according to any one of the preceding paragraphs, wherein the first and/or second antigen is an immunomodulator.

28. A bispecific antibody according to paragraph 27, wherein the immunomodulator is a checkpoint molecule.

29. A bispecific antibody according to paragraph 28, wherein the checkpoint molecule is a stimulatory checkpoint molecule, optionally wherein the stimulatory checkpoint molecule is selected from CD40, CD137, GITR, CD27, ICOS and OX40.

30. A bispecific antibody according to paragraph 28, wherein the checkpoint molecule is an inhibitory checkpoint molecule, optionally wherein the inhibitory checkpoint molecule is selected from CTLA-4, PD-1, Tim3, Lag3, Tigit and VISTA.

31. A bispecific antibody according to any one of the preceding paragraphs, wherein the first and/or second antigen is a tumour cell-associated antigen.

32. A bispecific antibody according to paragraph 31 wherein the tumour cell-associated antigen is selected from the group consisting of:

(m) products of mutated oncogenes and tumour suppressor genes;

(n) overexpressed or aberrantly expressed cellular proteins;

(o) tumour antigens produced by oncogenic viruses;

(p) oncofetal antigens;

(q) altered cell surface glycolipids and glycoproteins;

(r) cell type-specific differentiation antigens;

(s) hypoxia-induced antigens;

(t) tumour peptides presented by MHC class I;

(u) epithelial tumour antigens;

(v) haematological tumour-associated antigens;

(w) cancer testis antigens; and (x) melanoma antigens.

33. A bispecific antibody according to paragraph 32 wherein the tumour cell-associated antigen is selected from the group consisting of 5T4, CD20, CD19, MUC 1, CA-125, CO17-1A, EpCAM, HER2, EphA2, EphA3, DR5, FAP, OGD2, VEGFR, Her3, mesothelin and EGFR.

34. A bispecific antibody according to any one of the preceding paragraphs wherein the first and second antigen are selected from the group consisting of: CD40, EpCAM, 5T4, CD137, OX40, CTLA-4, GITR, EGFR and HER2.

35. A bispecific antibody according to any one of the preceding paragraphs wherein the bispecific antibody targets a pair of antigens selected from: OX40 and CTLA-4, OX40 and CD137, GITR and CTLA-4, CD137 and CTLA-4, OX40 and 5T4.

36. A bispecific antibody according to paragraph 35, wherein the first and second antigen are selected from CD40 and EpCAM.

37. A bispecific antibody according to paragraph 36 comprising one or more CDR sequences selected from:

```
a) CDRH1: GFTFSSYA (SEQ ID NO: 10); and/or b) CDRH2: IGSYGGGT (SEQ ID NO: 11); and/or c) CDRH3: ARYVNFGMDY (SEQ ID NO: 12); and/or d) CDRL1: QSISSY (SEQ ID NO: 13); and/or e) CDRL2: AAS (SEQ ID NO: 14); and/or f) CDRL3: QQYGRNPPT (SEQ ID NO: 15); and/or g) CDRH1: GYAFTNYW (SEQ ID NO: 18); and/or h) CDRH2: IFPGSGNI (SEQ ID NO: 19); and/or i) CDRH3: ARLRNWDEPMDY (SEQ ID NO: 20); and/or j) CDRL1: QSLLNSGNQKNY (SEQ ID NO: 21); and/or k) CDRL2: WAS (SEQ ID NO: 22); and/or

I) CDRL3: QNDYSYPLT (SEQ ID NO: 23)
```

38. A bispecific antibody according to paragraph 37 comprising one or more variable region sequences selected from:

```
(a) VH of SEQ ID NO: 16
(EVQLLESGGGLVQPGGSLRLSCAASGFTFSSYAMSWVRQAPGKGLEWV

SGIGSYGGGTYYADSVKGRFTISRDNSKNTLYLQMNSLRAEDTAVYYCA

RYVNFGMDYWGQGTLVTVSS); and/or (b) VL of SEQ ID NO: 17
(DIQMTQSPSSLSASVGDRVTITCRASQSISSYLNWYQQKPGKAPKLLI

YAASSLQSGVPSRFSGSGSGTDFTLTISSLQPEDFATYYCQQYGRNPPT

FGQGTKLEIK); and/or (c) VH of SEQ ID NO: 24
(EVQLLEQSGAELVRPGTSVKISCKASGYAFTNYWLGWVKQRPGHGLEW

IGDIFPGSGNIHYNEKFKGKATLTADKSSSTAYMQLSSLTFEDSAVYFC

ARLRNWDEPMDYWGQGTTVTVSS); and/or (d) VL of SEQ ID NO: 25
(ELVMTQSPSSLTVTAGEKVTMSCKSSQSLLNSGNQKNYLTWYQQKPGQ

PPKLLIYWASTRESGVPDRFTGSGSGTDFTLTISSVQAEDLAVYYCOND

YSYPLTFGAGTKLEIK)
```

39. A bispecific antibody according to paragraph 38, wherein:

(a) the first heavy chain polypeptide comprises or consists of the amino acid sequence of SEQ ID NO: 16; and/or (b) the first light chain polypeptide comprises or consists of the amino acid sequence of SEQ ID NO: 17; and/or (c) the second heavy chain polypeptide comprises or consists of the amino acid sequence of SEQ ID NO: 24; and/or (d) the second light chain polypeptide comprises or consists of the amino acid sequence of SEQ ID NO: 25.

40. A bispecific antibody according to any one of the preceding paragraphs, wherein the bispecific antibody is capable of inducing antibody dependent cell cytotoxicity (ADCC), antibody-dependent cellular phagocytosis (ADCP), complement-dependent cytotoxicity (CDC), and/ or apoptosis.

41. A bispecific antibody according to any one of the preceding paragraphs, wherein the bispecific antibody is capable of inducing:

(a) activation of B cells; and/or (b) activation of dendritic cells; and/or (c) activation of cytotoxic T cells, i.e. CD8+ T cells; and/or (d) activation of helper T cells, i.e. CD4+ T cells; and/or (e) improved tumour antigen cross-presentation by dendritic cells; and/or (f) expansion of tumour antigen-specific cytotoxic T cells; and/or (g) direct tumour cell killing via ADCC and/or via inhibition of tumour growth and survival signals; and/or (h) anti-angiogenic effects via interaction with endothelial and/or stromal cells; and/or (i) activation of natural killer cells; and/or (j) Treg depletion; and/or (k) reprograming of Tregs into effector T cells; and/or (l) depletion of tumour myeloid cell populations; and/or (m) reprogramming of tumour myeloid cell populations; and/or (n) internalisation of tumour debris by antigen-presenting cells; and/or (o) internalisation of tumour extracellular vesicles, e.g. exosomes, by antigen-presenting cells; and/or (p) localization to tumour tissue by binding to tumour cells.

42. A bispecific antibody according to any one of the preceding paragraphs, which induces an increase in the activity of an effector T cell, optionally wherein said increase is at least 1.5-fold, 4.5-fold or 7-fold higher than the increase in activity of an effector T cell induced by a combination of the immunoglobulin molecule and Fab fragment administered to the T cell as separate molecules.

43. A bispecific antibody according to paragraph 42, wherein said increase in T cell activity is an increase in proliferation and/or IFNγ or IL-2 production by the T cell.

44. A bispecific antibody according to any one of the preceding paragraphs, which induces an increase in the activation of an antigen-presenting cell, such as a B cell or dendritic cell.

45. A bispecific antibody according to paragraph 44, wherein said increase in activation is an increase in the expression of the co-stimulatory molecules CD80 or CD86 by the antigen-presenting cell.

46. A bispecific antibody according to any one of the preceding paragraphs, which induces an increase in the uptake of tumour debris or tumour extracellular vesicles by an antigen-presenting cell, such as a B cell or dendritic cell.

47. A bispecific antibody according to paragraph 46, wherein said increase in uptake is measured by the co-localization or internalization of the tumour debris or tumour extracellular vesicles by the antigen-presenting cell.

48. A bispecific antibody according to any one of the preceding paragraphs, wherein the bispecific antibody binds to the first and/or the second antigen with a $K_D$ of less than $100 \times 10^{-9}$M or less than $50 \times 10^{-9}$M or less than $25 \times 10^{-9}$M, preferably less than 10, 9, 8, 7, or $6 \times 10^{-9}$M, more preferably less than 5, 4, 3, 2, or $1 \times 10^{-9}$M, most preferably less than $9 \times 10^{10}$M.

49. An isolated nucleic acid molecule encoding a bispecific antibody according to any one of the preceding paragraphs, or a component polypeptide chain thereof.

50. A nucleic acid molecule according to paragraph 49 wherein the molecule is a cDNA molecule.

51. A nucleic acid molecule according to paragraph 49 or 50 encoding an antibody heavy chain or variable region thereof.

52. A nucleic acid molecule according to paragraph 49 or 50 encoding an antibody light chain or variable region thereof.

53. A vector comprising a nucleic acid molecule according to any one of paragraphs 49 to 52.

54. A vector according to paragraph 53 wherein the vector is an expression vector.

55. A recombinant host cell comprising a nucleic acid molecule according to any one of paragraphs 49 to 52 or a vector according to paragraph 53 or 54.

56. A host cell according to paragraph 55 wherein the host cell is a bacterial cell.

57. A host cell according to paragraph 55 wherein the host cell is a mammalian cell.

58. A host cell according to paragraph 55 wherein the host cell is a human cell.

59. A method for producing bispecific antibody according to any one of paragraphs 1 to 48, the method comprising culturing a host cell as defined in any of paragraphs 55 to 58 under conditions which permit expression of the bispecific antibody or component polypeptide chain thereof.

60. A pharmaceutical composition comprising an effective amount of a bispecific antibody according to any one of the paragraphs 1 to 48 and a pharmaceutically-acceptable diluent, carrier or excipient.

61. A pharmaceutical composition according to paragraph 60 adapted for parenteral delivery.

62. A pharmaceutical composition according to paragraph 60 adapted for intravenous delivery.

63. A bispecific antibody according to any one of the paragraphs 1 to 48 for use in medicine.

64. A bispecific antibody according to any one of the paragraphs 1 to 48 for use in treating or preventing a neoplastic disorder in a subject.

65. An antibody for use according to paragraph 64 wherein the neoplastic disorder is associated with the formation of solid tumours within the subject's body.

66. An antibody for use according to paragraph 65 wherein the solid tumour is selected from the group consisting of prostate cancer, breast cancer, lung cancer, colorectal cancer, melanomas, bladder cancer, brain/CNS cancer, cervical cancer, oesophageal cancer, gastric cancer, head/neck cancer, kidney cancer, liver cancer, lymphomas, ovarian cancer, pancreatic cancer and sarcomas.

67. An antibody for use according to paragraph 66 wherein the solid tumour is selected from the groups consisting of renal cell carcinoma, colorectal cancer, lung cancer, prostate cancer and breast cancer.

68. An antibody for use according to any one of paragraphs 64 to 67 wherein the antibody is for use in combination with one or more additional therapeutic agents.

69. An antibody for use according to paragraph 68 wherein the one or more additional therapeutic agents is/are an immunotherapeutic agent that binds a target selected from the group consisting of PD-1/PD-L1, CTLA-4, CD137, CD40, GITR, LAG3, TIM3, CD27, VISTA, OX40 and KIR.

70. Use of a bispecific antibody according to any one of paragraphs 1 to 48 in the preparation of a medicament for treating or preventing a neoplastic disorder in a subject.

71. A use according to paragraph 70 wherein the neoplastic disorder is associated with the formation of solid tumours within the subject's body.

72. A use according to paragraph 71 wherein the solid tumour is selected from the group consisting of prostate cancer, breast cancer, lung cancer, colorectal cancer, melanomas, bladder cancer, brain/CNS cancer, cervical cancer, oesophageal cancer, gastric cancer, head/neck cancer, kidney cancer, liver cancer, lymphomas, ovarian cancer, pancreatic cancer and sarcomas.

73. A use according to paragraph 72 wherein the solid tumour is selected from the groups consisting of renal cell carcinoma, colorectal cancer, lung cancer, prostate cancer and breast cancer.

74. A use according to any one of paragraphs 70 to 73 wherein the antibody is for use in combination with one or more additional therapeutic agents.

75. An antibody for use according to paragraph 74 wherein the one or more additional therapeutic agents is/are an immunotherapeutic agent that binds a target selected from the group consisting of PD-1/PD-L1, CTLA-4, CD137, CD40, GITR, LAG3, TIM3, CD27, VISTA, OX40 and KIR.

76. A method for the treatment or diagnosis of a neoplastic disorder in a subject, comprising the step of administering to the subject an effective amount of a bispecific antibody according to any one of the paragraphs 1 to 48.

77. A method according to paragraph 76 wherein the neoplastic disorder is associated with the formation of solid tumours within the subject's body.

78. A method according to paragraph 77 wherein the solid tumour is selected from the group consisting of prostate cancer, breast cancer, lung cancer, colorectal cancer, melanomas, bladder cancer, brain/CNS cancer, cervical cancer, oesophageal cancer, gastric cancer, head/neck cancer, kidney cancer, liver cancer, lymphomas, ovarian cancer, pancreatic cancer and sarcomas.

79. A method according to paragraph 78 wherein the solid tumour is selected from the groups consisting of renal cell carcinoma, colorectal cancer, lung cancer, prostate cancer and breast cancer.

80. A method according to any one of paragraphs 76 to 79 wherein the subject is human.

81. A method according to any one of paragraphs 76 to 80 wherein the method comprises administering the bispecific antibody systemically.

82. A method according to any one of paragraphs 76 to 81 further comprising administering to the subject one or more additional therapeutic agents.

83. A method according to paragraph 82 wherein the one or more additional therapeutic agents is/are an immunotherapeutic agent that binds a target selected from the group consisting of PD-1/PD-1L, CTLA-4, CD137, CD40, GITR, LAG3, TIM3, CD27, VISTA, OX40 and KIR.

84. A method of producing a bispecific antibody according to any one of paragraphs 1 to 48 comprising expressing three polypeptide chains in the same host cell, wherein the three polypeptide chains are:

(d) an immunoglobulin heavy chain (the first heavy chain) fused via a polypeptide linker to a second light chain;

(e) a first light chain; and (f) a second heavy chain

85. A method of producing a bispecific antibody according to paragraph 84 further comprising the step of modifying the ratios of the chains (a), (b) and (c) to optimise formation of a bispecific antibody.

---

The invention claimed is:

1. A bispecific antibody comprising:
(a) an immunoglobulin G (IgG) molecule comprising an antigen binding domain having specificity for a first antigen, the IgG molecule comprising a first heavy chain polypeptide and a first light chain polypeptide; and
(b) at least one appended IgG Fab fragment having specificity for a second antigen, the appended IgG Fab fragment comprising a second heavy chain polypeptide and a second light chain polypeptide;
wherein the second light chain polypeptide is fused to the C-terminus of the first heavy chain polypeptide;
wherein the IgG molecule and the appended IgG Fab fragment comprise an antibody VL region, an antibody VH region, a CH1 region and a CKappa or CLambda region,
wherein the bispecific antibody comprises mutations to promote association of the heavy chain with the light chain,
wherein the VL region of the IgG molecule comprises a Q44E mutation according to IMGT numbering,
wherein the VH region of the IgG molecule comprises Q44R mutation according to IMGT numbering,
wherein the VL region of the appended IgG Fab fragment comprises a Q44R mutation according to IMGT numbering,
wherein the VH region of the appended IgG Fab fragment comprises a Q44E mutation according to IMGT numbering,
wherein the CH1 region of the IgG molecule comprises a H168A mutation and an F170G mutation according to EU numbering, and
wherein the CKappa or CLambda region of the IgG molecule comprises a L135Y mutation and an S176W mutation according to Kabat numbering,
wherein the CH1 region of the appended IgG Fab fragment comprises a T187E mutation according to EU numbering, and
wherein the CKappa or CLambda region of the appended IgG Fab fragment comprises a T/S114A mutation and an N/S137K mutation according to Kabat numbering.

2. The bispecific antibody according to claim 1, wherein at least one of the VL regions and/or the VH regions further comprises one or more mutation at a position selected from 49 and 120 according to IMGT numbering;
optionally,
wherein a mutation at position 49 is at position G49 or A49 and/or a mutation at position 120 is at position Q120 or A120 according to IMGT numbering;
optionally,
wherein a mutation at position 49 is a G49C or A49D mutation and/or a mutation at position 120 is a Q120C, A120C or Q120K mutation according to IMGT numbering.

3. The bispecific antibody according to claim 1, wherein the bispecific antibody is tetravalent, with dual binding to each of the two antigens.

4. The bispecific antibody according to claim 1, wherein the immunoglobulin molecule comprises two copies of the first heavy chain polypeptide and two copies of the first light chain polypeptide,
and the bispecific antibody further comprises two Fab fragments according to (b),
and the first Fab fragment is fused to the C-terminus of the first copy of the first heavy chain polypeptide via the light chain polypeptide of the Fab fragment;
and the second Fab fragment is fused to the C-terminus of the second copy of the first heavy chain polypeptide via the light chain polypeptide of the Fab fragment.

5. The bispecific antibody according to claim 1, wherein the immunoglobulin molecule comprises a human Fc region or a variant of a said region, where the region is an IgG1, IgG2, IgG3 or IgG4 region.

6. The bispecific antibody according to claim 1, wherein the Fab fragment(s) is linked to the C terminal end of the immunoglobulin via a linker;
optionally,
wherein the linker is a peptide with the amino acid sequence SGGGGSGGGGS (SEQ ID NO: 5), SGGGGSGGGGSAP (SEQ ID NO: 6, NFSQP (SEQ ID NO: 7), KRTVA (SEQ ID NO: 8), GGGGSGGGGSGGGGS (SEQ ID NO: 9), (SG)m, where m=1 to 7, or GGGGSGGGGS (SEQ ID NO: 34).

7. The bispecific antibody according to claim 1, wherein the first and/or second antigen is an immunomodulator;
optionally,
wherein the immunomodulator is a checkpoint molecule,
optionally,
wherein the checkpoint molecule is a stimulatory checkpoint molecule, optionally wherein the stimulatory checkpoint molecule is selected from CD40, CD137, GITR, CD27, ICOS and OX40;
optionally,
wherein the checkpoint molecule is an inhibitory checkpoint molecule, optionally wherein the inhibitory checkpoint molecule is selected from CTLA-4, PD-1, Tim3, Lag3, Tigit and VISTA; or
wherein the first and/or second antigen is a tumour cell-associated antigen;
optionally,
wherein the tumour cell-associated antigen is selected from the group consisting of:
(a) products of mutated oncogenes and tumour suppressor genes;
(b) overexpressed or aberrantly expressed cellular proteins;
(c) tumour antigens produced by oncogenic viruses;

(d) oncofetal antigens;

(e) altered cell surface glycolipids and glycoproteins;

(f) cell type-specific differentiation antigens;

(g) hypoxia-induced antigens;

(h) tumour peptides presented by MHC class I;

(i) epithelial tumour antigens;

(j) haematological tumour-associated antigens;

(k) cancer testis antigens; and (l) melanoma antigens;

optionally, wherein the tumour cell-associated antigen is selected from the group consisting of 5T4, CD20, CD19, MUC 1, CA-125, CO17-1A, EpCAM, HER2, EphA2, EphA3, DR5, FAP, OGD2, VEGFR, Her3, mesothelin and EGFR.

8. The bispecific antibody according to claim 1, wherein one or more amino acids are removed from the N-terminus or termini of the at least one appended Fab light chain of (b);

optionally, wherein:

three amino acids are removed from the N-terminus or termini of the at least one appended Fab light chain of (b); or six amino acids are removed from the N-terminus or termini of the at least one appended Fab light chain of (b); or nine amino acids are removed from the N-terminus or termini of the at least one appended Fab light chain of (b).

9. A method for the treatment or diagnosis of a neoplastic disorder in a subject, comprising the step of administering to the subject an effective amount of a bispecific antibody according to claim 1, optionally wherein the subject is human.

10. The method according to claim 9 wherein the neoplastic disorder is associated with the formation of solid tumours within the subject's body;

optionally, wherein the solid tumour is selected from the group consisting of prostate cancer, breast cancer, lung cancer, colorectal cancer, melanoma, bladder cancer, brain and/or CNS cancer, cervical cancer, oesophageal cancer, gastric cancer, head and neck cancer, kidney cancer, liver cancer, ovarian cancer, renal cell carcinoma, pancreatic cancer and sarcoma.

11. The method according to claim 9, wherein the method comprises administering the bispecific antibody systemically.

12. The method according to claim 9, further comprising administering to the subject one or more additional therapeutic agent;

optionally, wherein the one or more additional therapeutic agent is an immunotherapeutic agent that binds a target selected from the group consisting of PD-1, PD-L1, CTLA-4, CD137, CD40, GITR, LAG3, TIM3, CD27, VISTA, OX40 and KIR.

13. A method of producing a bispecific antibody according to claim 1, comprising expressing three polypeptide chains in the same host cell, wherein the three polypeptide chains are:

(a) the first heavy chain fused via a polypeptide linker to the second light chain;

(b) the first light chain; and (c) the second heavy chain;

optionally, further comprising the step of modifying the ratios of the chains (a), (b) and (c) to optimise formation of a bispecific antibody.

14. The bispecific antibody of claim 1, wherein the IgG molecule and the appended IgG Fab fragment comprise a CKappa region.

\* \* \* \* \*

SEQUENCE LISTING

```
<160> NUMBER OF SEQ ID NOS: 72

<210> SEQ ID NO 1
<211> LENGTH: 117
<212> TYPE: PRT
<213> ORGANISM: Artificial Sequence
<220> FEATURE:
<223> OTHER INFORMATION: VH

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Val Asn Phe Gly Met Asp Tyr Trp Gly Gln Gly Thr Leu
            100                 105                 110

Val Thr Val Ser Ser
        115
```

<210> SEQ ID NO 2
<211> LENGTH: 107
<212> TYPE: PRT
<213> ORGANISM: Artificial Sequence
<220> FEATURE:
<223> OTHER INFORMATION: VL

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 3
<211> LENGTH: 103
<212> TYPE: PRT
<213> ORGANISM: Artificial Sequence
<220> FEATURE:
<223> OTHER INFORMATION: CH1

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 4
<211> LENGTH: 107
<212> TYPE: PRT
<213> ORGANISM: Artificial Sequence
<220> FEATURE:
<223> OTHER INFORMATION: CKappa

<400> SEQUENCE: 4

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln

```
              35              40              45
Ser Gly Asn Ser Gln Glu Ser Val Thr Glu Gln Asp Ser Lys Asp Ser
   50              55              60

Thr Tyr Ser Leu Ser Ser Thr Leu Thr Leu Ser Lys Ala Asp Tyr Glu
65              70              75              80

Lys His Lys Val Tyr Ala Cys Glu Val Thr His Gln Gly Leu Ser Ser
              85              90              95

Pro Val Thr Lys Ser Phe Asn Arg Gly Glu Cys
           100             105
```

```
<210> SEQ ID NO 5
<211> LENGTH: 11
<212> TYPE: PRT
<213> ORGANISM: Artificial Sequence
<220> FEATURE:
<223> OTHER INFORMATION: linker

<400> SEQUENCE: 5

Ser Gly Gly Gly Gly Ser Gly Gly Gly Gly Ser
1               5               10
```

```
<210> SEQ ID NO 6
<211> LENGTH: 13
<212> TYPE: PRT
<213> ORGANISM: Artificial Sequence
<220> FEATURE:
<223> OTHER INFORMATION: linker

<400> SEQUENCE: 6

Ser Gly Gly Gly Gly Ser Gly Gly Gly Gly Ser Ala Pro
1               5               10
```

```
<210> SEQ ID NO 7
<211> LENGTH: 5
<212> TYPE: PRT
<213> ORGANISM: Artificial Sequence
<220> FEATURE:
<223> OTHER INFORMATION: linker

<400> SEQUENCE: 7

Asn Phe Ser Gln Pro
1               5
```

```
<210> SEQ ID NO 8
<211> LENGTH: 5
<212> TYPE: PRT
<213> ORGANISM: Artificial Sequence
<220> FEATURE:
<223> OTHER INFORMATION: linker

<400> SEQUENCE: 8

Lys Arg Thr Val Ala
1               5
```

```
<210> SEQ ID NO 9
<211> LENGTH: 15
<212> TYPE: PRT
<213> ORGANISM: Artificial Sequence
<220> FEATURE:
<223> OTHER INFORMATION: linker

<400> SEQUENCE: 9

Gly Gly Gly Gly Ser Gly Gly Gly Gly Ser Gly Gly Gly Gly Ser
1               5               10              15
```

-continued

```
<210> SEQ ID NO 10
<211> LENGTH: 8
<212> TYPE: PRT
<213> ORGANISM: Artificial Sequence
<220> FEATURE:
<223> OTHER INFORMATION: CDRH1

<400> SEQUENCE: 10

Gly Phe Thr Phe Ser Ser Tyr Ala
1               5

<210> SEQ ID NO 11
<211> LENGTH: 8
<212> TYPE: PRT
<213> ORGANISM: Artificial Sequence
<220> FEATURE:
<223> OTHER INFORMATION: CDRH2

<400> SEQUENCE: 11

Ile Gly Ser Tyr Gly Gly Gly Thr
1               5

<210> SEQ ID NO 12
<211> LENGTH: 10
<212> TYPE: PRT
<213> ORGANISM: Artificial Sequence
<220> FEATURE:
<223> OTHER INFORMATION: CDRH3

<400> SEQUENCE: 12

Ala Arg Tyr Val Asn Phe Gly Met Asp Tyr
1               5                   10

<210> SEQ ID NO 13
<211> LENGTH: 6
<212> TYPE: PRT
<213> ORGANISM: Artificial Sequence
<220> FEATURE:
<223> OTHER INFORMATION: CDRL1

<400> SEQUENCE: 13

Gln Ser Ile Ser Ser Tyr
1               5

<210> SEQ ID NO 14

<400> SEQUENCE: 14

000

<210> SEQ ID NO 15
<211> LENGTH: 9
<212> TYPE: PRT
<213> ORGANISM: Artificial Sequence
<220> FEATURE:
<223> OTHER INFORMATION: CDRL3

<400> SEQUENCE: 15

Gln Gln Tyr Gly Arg Asn Pro Pro Thr
1               5

<210> SEQ ID NO 16
<211> LENGTH: 117
<212> TYPE: PRT
<213> ORGANISM: Artificial Sequence
<220> FEATURE:
<223> OTHER INFORMATION: VH
```

<400> SEQUENCE: 16

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Gly Ser Tyr Gly Gly Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Val Asn Phe Gly Met Asp Tyr Trp Gly Gln Gly Thr Leu
            100                 105                 110

Val Thr Val Ser Ser
        115
```

<210> SEQ ID NO 17
<211> LENGTH: 107
<212> TYPE: PRT
<213> ORGANISM: Artificial Sequence
<220> FEATURE:
<223> OTHER INFORMATION: VL

<400> SEQUENCE: 17

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Arg Asn Pro Pro
                85                  90                  95

Thr Phe Gly Gln Gly Thr Lys Leu Glu Ile Lys
            100                 105
```

<210> SEQ ID NO 18
<211> LENGTH: 8
<212> TYPE: PRT
<213> ORGANISM: Artificial Sequence
<220> FEATURE:
<223> OTHER INFORMATION: CDRH1

<400> SEQUENCE: 18

```
Gly Tyr Ala Phe Thr Asn Tyr Trp
1               5
```

<210> SEQ ID NO 19
<211> LENGTH: 8
<212> TYPE: PRT
<213> ORGANISM: Artificial Sequence
<220> FEATURE:
<223> OTHER INFORMATION: CDRH2

<400> SEQUENCE: 19

Ile Phe Pro Gly Ser Gly Asn Ile
1               5

<210> SEQ ID NO 20
<211> LENGTH: 12
<212> TYPE: PRT
<213> ORGANISM: Artificial Sequence
<220> FEATURE:
<223> OTHER INFORMATION: CDRH3

<400> SEQUENCE: 20

Ala Arg Leu Arg Asn Trp Asp Glu Pro Met Asp Tyr
1               5                   10

<210> SEQ ID NO 21
<211> LENGTH: 12
<212> TYPE: PRT
<213> ORGANISM: Artificial Sequence
<220> FEATURE:
<223> OTHER INFORMATION: CDRL1

<400> SEQUENCE: 21

Gln Ser Leu Leu Asn Ser Gly Asn Gln Lys Asn Tyr
1               5                   10

<210> SEQ ID NO 22

<400> SEQUENCE: 22

000

<210> SEQ ID NO 23
<211> LENGTH: 9
<212> TYPE: PRT
<213> ORGANISM: Artificial Sequence
<220> FEATURE:
<223> OTHER INFORMATION: CDRL3

<400> SEQUENCE: 23

Gln Asn Asp Tyr Ser Tyr Pro Leu Thr
1               5

<210> SEQ ID NO 24
<211> LENGTH: 120
<212> TYPE: PRT
<213> ORGANISM: Artificial Sequence
<220> FEATURE:
<223> OTHER INFORMATION: VH

<400> SEQUENCE: 24

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
                20                  25                  30

Tyr Trp Leu Gly Trp Val Lys Gln Arg Pro Gly His Gly Leu Glu Trp
            35                  40                  45

Ile Gly Asp Ile Phe Pro Gly Ser Gly Asn Ile His Tyr Asn Glu Lys
        50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Phe
                85                  90                  95

Cys Ala Arg Leu Arg Asn Trp Asp Glu Pro Met Asp Tyr Trp Gly Gln
            100                 105                 110

Gly Thr Thr Val Thr Val Ser Ser
        115                 120

<210> SEQ ID NO 25
<211> LENGTH: 113
<212> TYPE: PRT
<213> ORGANISM: Artificial Sequence
<220> FEATURE:
<223> OTHER INFORMATION: VL

<400> SEQUENCE: 25

Glu Leu Val Met Thr Gln Ser Pro Ser Ser Leu Thr Val Thr Ala Gly
1                   5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys

<210> SEQ ID NO 26
<211> LENGTH: 351
<212> TYPE: DNA
<213> ORGANISM: Artificial Sequence
<220> FEATURE:
<223> OTHER INFORMATION: VH

<400> SEQUENCE: 26
gaagtgcagc tgctggaaag cggcggcggc ctggtgcagc cgggcggcag cctgcgcctg      60
agctgcgcgg cgagcggctt tacctttagc agctatgcga tgagctgggt gcgccaggcg     120
ccgggcaaag cctggaatgg gtgagcgcg attagcggca cgcggcggcag cacctattat     180 gcggatagcg tgaaaggccg ctttaccatt agccgcgata acagcaaaaa caccctgtat     240
ctgcagatga acagcctgcg cgcggaagat accgcggtgt attattgcgc gcgctatgtg     300
aactttggca tggattattg gggccagggc accctggtga ccgtgagcag c              351

<210> SEQ ID NO 27
<211> LENGTH: 321
<212> TYPE: DNA
<213> ORGANISM: Artificial Sequence
<220> FEATURE:
<223> OTHER INFORMATION: VL

<400> SEQUENCE: 27
gatattcaga tgacccagag cccgagcagc ctgagcgcga gcgtgggcga tcgcgtgacc      60
attacctgcc gcgcgagcca gagcattagc agctatctga actggtatca gcagaaaccg     120
ggcaaagcgc cgaaactgct gatttatgcg gcgagcagcc tgcagagcgg cgtgccgagc     180
cgctttagcg gcagcggcag cggcaccgat tttaccctga ccattagcag cctgcagccg     240

-continued

```
gaagattttg cgacctatta ttgccagcag agctatagca ccccgtatac ctttggccag        300
ggcaccaaac tggaaattaa a                                                    321

<210> SEQ ID NO 28
<211> LENGTH: 309
<212> TYPE: DNA
<213> ORGANISM: Artificial Sequence
<220> FEATURE:
<223> OTHER INFORMATION: CH1

<400> SEQUENCE: 28
gcgagcacca aaggcccgag cgtgtttccg ctggcgccga gcagcaaaag caccagcggc         60
ggcaccgcgg cgctgggctg cctggtgaaa gattattttc cggaaccggt gaccgtgagc        120
tggaacagcg gcgcgctgac cagcggcgtg catacctttc cggcggtgct gcagagcagc        180
ggcctgtata gcctgagcag cgtggtgacc gtgccgagca gcagcctggg cacccagacc        240
tatatttgca acgtgaacca taaaccgagc aacaccaaag tggataaaaa agtggaaccg        300
aaaagctgc                                                                 309

<210> SEQ ID NO 29
<211> LENGTH: 321
<212> TYPE: DNA
<213> ORGANISM: Artificial Sequence
<220> FEATURE:
<223> OTHER INFORMATION: CKappa

<400> SEQUENCE: 29
cgcaccgtgg cggcgccgag cgtgtttatt tttccgccga cgatgaaca gctgaaaagc          60 ggcaccgcga gcgtggtgtg cctgctgaac aacttttatc cgcgcgaagc gaaagtgcag        120
tggaaagtgg ataacgcgct gcagagcggc aacagccagg aaagcgtgac cgaacaggat        180
agcaaagata gcacctatag cctgagcagc accctgaccc tgagcaaagc ggattatgaa        240
aaacataaag tgtatgcgtg cgaagtgacc catcagggcc tgagcagccc ggtgaccaaa        300
agctttaacc gcggcgaatg c                                                    321

<210> SEQ ID NO 30
<211> LENGTH: 351
<212> TYPE: DNA
<213> ORGANISM: Artificial Sequence
<220> FEATURE:
<223> OTHER INFORMATION: VH

<400> SEQUENCE: 30
gaagtgcagc tgctggaaag cggcggcggc ctggtgcagc cgggcggcag cctgcgcctg         60
agctgcgcgg cgagcggctt tacctttagc agctatgcga tgagctgggt gcgccaggcg        120
ccgggcaaag cctggaatgg ggtgagcggc attggcagct atggcggcgg cacctattat        180
gcggatagcg tgaaaggccg ctttaccatt agccgcgata acagcaaaaa caccctgtat        240
ctgcagatga acagcctgcg cgcggaagat accgcggtgt attattgcgc gcgctatgtg        300
aactttggca tggattattg gggccagggc accctggtga ccgtgagcag c                  351

<210> SEQ ID NO 31
<211> LENGTH: 321
<212> TYPE: DNA
<213> ORGANISM: Artificial Sequence
<220> FEATURE:
<223> OTHER INFORMATION: VL

<400> SEQUENCE: 31
```

```
gatattcaga tgacccagag cccgagcagc ctgagcgcga gcgtgggcga tcgcgtgacc      60
attacctgcc gcgcgagcca gagcattagc agctatctga actggtatca gcagaaaccg     120
ggcaaagcgc cgaaactgct gatttatgcg gcgagcagcc tgcagagcgg cgtgccgagc     180
cgctttagcg gcagcggcag cggcaccgat tttaccctga ccattagcag cctgcagccg     240
gaagattttg cgacctatta ttgccagcag tatggccgca acccgccgac ctttggccag     300
ggcaccaaac tggaaattaa a                                                321

<210> SEQ ID NO 32
<211> LENGTH: 360
<212> TYPE: DNA
<213> ORGANISM: Artificial Sequence
<220> FEATURE:
<223> OTHER INFORMATION: VH

<400> SEQUENCE: 32
gaagtgcagc tgctggaaca gagcggcgcg gaactggtgc gcccgggcac cagcgtgaaa      60
attagctgca aagcgagcgg ctatgcgttt accaactatt ggctgggctg ggtgaaacag     120
cgcccgggcc atggcctgga atggattggc gatattttc cgggcagcgg caacattcat     180
tataacgaaa aatttaaagg caaagcgacc ctgaccgcgg ataaaagcag cagcaccgcg     240
tatatgcagc tgagcagcct gacctttgaa gatagcgcgg tgtatttttg cgcgcgcctg     300
cgcaactggg atgaaccgat ggattattgg ggccagggca ccaccgtgac cgtgagcagc     360

<210> SEQ ID NO 33
<211> LENGTH: 339
<212> TYPE: DNA
<213> ORGANISM: Artificial Sequence
<220> FEATURE:
<223> OTHER INFORMATION: VL

<400> SEQUENCE: 33
gaactggtga tgacccagag cccgagcagc ctgaccgtga ccgcgggcga aaaagtgacc      60
atgagctgca aaagcagcca gagcctgctg aacagcggca accagaaaaa ctatctgacc     120
tggtatcagc agaaaccggg ccagccgccg aaactgctga tttattgggc gagcacccgc     180
gaaagcggcg tgccggatcg ctttaccggc agcggcagcg gcaccgattt taccctgacc     240
attagcagcg tgcaggcgga agatctggcg gtgtattatt gccagaacga ttatagctat     300
ccgctgacct ttggcgcggg caccaaactg gaaattaaa                             339

<210> SEQ ID NO 34
<211> LENGTH: 10
<212> TYPE: PRT
<213> ORGANISM: Artificial Sequence
<220> FEATURE:
<223> OTHER INFORMATION: linker

<400> SEQUENCE: 34

Gly Gly Gly Gly Ser Gly Gly Gly Gly Ser
1               5                   10

<210> SEQ ID NO 35
<211> LENGTH: 8
<212> TYPE: PRT
<213> ORGANISM: Artificial Sequence
<220> FEATURE:
<223> OTHER INFORMATION: CDRH1

<400> SEQUENCE: 35
```

Gly Phe Thr Phe Ser Tyr Gly Ser
1               5

<210> SEQ ID NO 36
<211> LENGTH: 8
<212> TYPE: PRT
<213> ORGANISM: Artificial Sequence
<220> FEATURE:
<223> OTHER INFORMATION: CDRH2

<400> SEQUENCE: 36

Ile Ser Ser Gly Ser Gly Ser Thr
1               5

<210> SEQ ID NO 37
<211> LENGTH: 14
<212> TYPE: PRT
<213> ORGANISM: Artificial Sequence
<220> FEATURE:
<223> OTHER INFORMATION: CDRH3

<400> SEQUENCE: 37

Ala Arg Ser Ser Tyr Tyr Gly Ser Tyr Tyr Ser Ile Asp Tyr
1               5                   10

<210> SEQ ID NO 38
<211> LENGTH: 9
<212> TYPE: PRT
<213> ORGANISM: Artificial Sequence
<220> FEATURE:
<223> OTHER INFORMATION: CDRL3

<400> SEQUENCE: 38

Gln Gln Tyr Tyr Asp Asn Leu Pro Thr
1               5

<210> SEQ ID NO 39
<211> LENGTH: 121
<212> TYPE: PRT
<213> ORGANISM: Artificial Sequence
<220> FEATURE:
<223> OTHER INFORMATION: VH

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Gly
            20                  25                  30

Ser Met Tyr Trp Val Arg Gln Ala Pro Gly Lys Gly Leu Glu Trp Val
        35                  40                  45

Ser Ser Ile Ser Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Ser Tyr Tyr Ser Ile Asp Tyr Trp Gly
            100                 105                 110

Gln Gly Thr Leu Val Thr Val Ser Ser
        115                 120

<210> SEQ ID NO 40

```
<211> LENGTH: 107
<212> TYPE: PRT
<213> ORGANISM: Artificial Sequence
<220> FEATURE:
<223> OTHER INFORMATION: VL

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Asn Leu Pro
                85                  90                  95

Thr Phe Gly Gln Gly Thr Lys Leu Glu Ile Lys
            100                 105

<210> SEQ ID NO 41
<211> LENGTH: 9
<212> TYPE: PRT
<213> ORGANISM: Artificial Sequence
<220> FEATURE:
<223> OTHER INFORMATION: CDRH1

<400> SEQUENCE: 41

Gly Phe Thr Phe Ser Ser Tyr Ala Met
1               5

<210> SEQ ID NO 42
<211> LENGTH: 8
<212> TYPE: PRT
<213> ORGANISM: Artificial Sequence
<220> FEATURE:
<223> OTHER INFORMATION: CDRH2

<400> SEQUENCE: 42

Ile Ser Gly Ser Gly Gly Ser Thr
1               5

<210> SEQ ID NO 43
<211> LENGTH: 14
<212> TYPE: PRT
<213> ORGANISM: Artificial Sequence
<220> FEATURE:
<223> OTHER INFORMATION: CDRH3

<400> SEQUENCE: 43

Ala Arg Tyr Tyr Gly Gly Tyr Tyr Ser Ala Trp Met Asp Tyr
1               5                   10

<210> SEQ ID NO 44
<211> LENGTH: 9
<212> TYPE: PRT
<213> ORGANISM: Artificial Sequence
<220> FEATURE:
<223> OTHER INFORMATION: CDRL3

<400> SEQUENCE: 44

Gln Gln Thr Tyr Gly Tyr Leu His Thr
```

1                    5

<210> SEQ ID NO 45
<211> LENGTH: 121
<212> TYPE: PRT
<213> ORGANISM: Artificial Sequence
<220> FEATURE:
<223> OTHER INFORMATION: VH

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Gly Tyr Tyr Ser Ala Trp Met Asp Tyr Trp Gly
            100                 105                 110

Gln Gly Thr Leu Val Thr Val Ser Ser
        115                 120

<210> SEQ ID NO 46
<211> LENGTH: 107
<212> TYPE: PRT
<213> ORGANISM: Artificial Sequence
<220> FEATURE:
<223> OTHER INFORMATION: VL

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Gly Tyr Leu His
                85                  90                  95

Thr Phe Gly Gln Gly Thr Lys Leu Glu Ile Lys
            100                 105

<210> SEQ ID NO 47
<211> LENGTH: 9
<212> TYPE: PRT
<213> ORGANISM: Artificial Sequence
<220> FEATURE:
<223> OTHER INFORMATION: CDRH1

<400> SEQUENCE: 47

Gly Phe Thr Phe Gly Gly Tyr Tyr Met
1               5

<210> SEQ ID NO 48
<211> LENGTH: 8
<212> TYPE: PRT
<213> ORGANISM: Artificial Sequence
<220> FEATURE:
<223> OTHER INFORMATION: CDRH2

<400> SEQUENCE: 48

Ile Pro Gly Ser Gly Gly Ser Thr
1               5

<210> SEQ ID NO 49
<211> LENGTH: 10
<212> TYPE: PRT
<213> ORGANISM: Artificial Sequence
<220> FEATURE:
<223> OTHER INFORMATION: CDRH3

<400> SEQUENCE: 49

Ala Arg Tyr Asp Tyr Tyr Trp Met Asp Tyr
1               5                   10

<210> SEQ ID NO 50
<211> LENGTH: 10
<212> TYPE: PRT
<213> ORGANISM: Artificial Sequence
<220> FEATURE:
<223> OTHER INFORMATION: CDRL3

<400> SEQUENCE: 50

Gln Gln Gly His Gly Ser Tyr Pro His Thr
1               5                   10

<210> SEQ ID NO 51
<211> LENGTH: 117
<212> TYPE: PRT
<213> ORGANISM: Artificial Sequence
<220> FEATURE:
<223> OTHER INFORMATION: VH

<400> SEQUENCE: 51

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Gly Tyr
            20                  25                  30

Tyr Met Ser Trp Val Arg Gln Ala Pro Gly Lys Gly Leu Glu Trp Val
        35                  40                  45

Ser Tyr Ile Pro Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asp Tyr Tyr Trp Met Asp Tyr Trp Gly Gln Gly Thr Leu
            100                 105                 110

Val Thr Val Ser Ser
        115

<210> SEQ ID NO 52
<211> LENGTH: 108
<212> TYPE: PRT
<213> ORGANISM: Artificial Sequence

```
<220> FEATURE:
<223> OTHER INFORMATION: VL

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Gly Ser Tyr Pro
                85                  90                  95

His Thr Phe Gly Gln Gly Thr Lys Leu Glu Ile Lys
            100                 105

<210> SEQ ID NO 53
<211> LENGTH: 9
<212> TYPE: PRT
<213> ORGANISM: Artificial Sequence
<220> FEATURE:
<223> OTHER INFORMATION: CDRH1

<400> SEQUENCE: 53

Gly Phe Thr Phe Ser Ser Tyr Tyr Met
1               5

<210> SEQ ID NO 54
<211> LENGTH: 8
<212> TYPE: PRT
<213> ORGANISM: Artificial Sequence
<220> FEATURE:
<223> OTHER INFORMATION: CDRH2

<400> SEQUENCE: 54

Ile Gly Ser Tyr Tyr Gly Tyr Thr
1               5

<210> SEQ ID NO 55
<211> LENGTH: 16
<212> TYPE: PRT
<213> ORGANISM: Artificial Sequence
<220> FEATURE:
<223> OTHER INFORMATION: CDRH3

<400> SEQUENCE: 55

Ala Arg Ala Tyr Tyr Asp Tyr Asn Tyr Tyr Ala Tyr Phe Asp Tyr
1               5                   10                  15

<210> SEQ ID NO 56
<211> LENGTH: 10
<212> TYPE: PRT
<213> ORGANISM: Artificial Sequence
<220> FEATURE:
<223> OTHER INFORMATION: CDRL3

<400> SEQUENCE: 56

Gln Gln Ser Val Pro His Tyr Pro Phe Thr
1               5                   10
```

```
<210> SEQ ID NO 57
<211> LENGTH: 123
<212> TYPE: PRT
<213> ORGANISM: Artificial Sequence
<220> FEATURE:
<223> OTHER INFORMATION: VH

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Gly Trp Val Arg Gln Ala Pro Gly Lys Gly Leu Glu Trp Val
        35                  40                  45

Ser Gly Ile Gly Ser Tyr Tyr Gly Tyr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Tyr Tyr Asp Tyr Asn Tyr Tyr Ala Tyr Phe Asp Tyr
            100                 105                 110

Trp Gly Gln Gly Thr Leu Val Thr Val Ser Ser
        115                 120

<210> SEQ ID NO 58
<211> LENGTH: 108
<212> TYPE: PRT
<213> ORGANISM: Artificial Sequence
<220> FEATURE:
<223> OTHER INFORMATION: VL

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Pro His Tyr Pro
                85                  90                  95

Phe Thr Phe Gly Gln Gly Thr Lys Leu Glu Ile Lys
            100                 105

<210> SEQ ID NO 59
<211> LENGTH: 106
<212> TYPE: PRT
<213> ORGANISM: Artificial Sequence
<220> FEATURE:
<223> OTHER INFORMATION: CLambda 1

<400> SEQUENCE: 59

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30
```

```
Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
                100                 105

<210> SEQ ID NO 60
<211> LENGTH: 106
<212> TYPE: PRT
<213> ORGANISM: Artificial Sequence
<220> FEATURE:
<223> OTHER INFORMATION: CLambda 2

<400> SEQUENCE: 60

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
                100                 105

<210> SEQ ID NO 61
<211> LENGTH: 106
<212> TYPE: PRT
<213> ORGANISM: Artificial Sequence
<220> FEATURE:
<223> OTHER INFORMATION: CLambda 3

<400> SEQUENCE: 61

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
                100                 105
```

```
<210> SEQ ID NO 62
<211> LENGTH: 318
<212> TYPE: DNA
<213> ORGANISM: Artificial Sequence
<220> FEATURE:
<223> OTHER INFORMATION: CLambda 1

<400> SEQUENCE: 62
ggccagccga aagcgaaccc gaccgtgacc ctgtttccgc cgagcagcga agaactgcag        60
gcgaacaaag cgaccctggt gtgcctgatt agcgattttt atccgggcgc ggtgaccgtg       120
gcgtggaaag cggatggcag cccggtgaaa gcgggcgtgg aaaccaccaa accgagcaaa       180
cagagcaaca acaaatatgc ggcgagcagc tatctgagcc tgaccccgga acagtggaaa       240
agccatcgca gctatagctg ccaggtgacc catgaaggca gcaccgtgga aaaaaccgtg       300
gcgccgaccg aatgcagc                                                     318

<210> SEQ ID NO 63
<211> LENGTH: 318
<212> TYPE: DNA
<213> ORGANISM: Artificial Sequence
<220> FEATURE:
<223> OTHER INFORMATION: CLambda 2

<400> SEQUENCE: 63
ggccagccga aagcggcgcc gagcgtgacc ctgtttccgc cgagcagcga agaactgcag        60
gcgaacaaag cgaccctggt gtgcctgatt agcgattttt atccgggcgc ggtgaccgtg       120
gcgtggaaag cggatagcag cccggtgaaa gcgggcgtgg aaaccaccac cccgagcaaa       180
cagagcaaca acaaatatgc ggcgagcagc tatctgagcc tgaccccgga acagtggaaa       240
agccatcgca gctatagctg ccaggtgacc catgaaggca gcaccgtgga aaaaaccgtg       300
gcgccgaccg aatgcagc                                                     318

<210> SEQ ID NO 64
<211> LENGTH: 321
<212> TYPE: DNA
<213> ORGANISM: Artificial Sequence
<220> FEATURE:
<223> OTHER INFORMATION: CLambda 3

<400> SEQUENCE: 64
ggccagccga aagcggcgcc gagcgtgacc ctgtttccgc cgagcagcga agaactgcag        60
gcgaacaaag cgaccctggt gtgcctgatt agcgattttt atccgggcgc ggtgaccgtg       120
gcgtggaaag cggatagcag cccggtgaaa gcgggcgtgg aaaccaccac cccgagcaaa       180
cagagcaaca acaaatatgc ggcgagcagc tatctgagcc tgaccccgga acagtggaaa       240
agccataaaa gctatagctg ccaggtgacc catgaaggca gcaccgtgga aaaaaccgtg       300
gcgccgaccg aatgcagcag c                                                 321

<210> SEQ ID NO 65
<211> LENGTH: 363
<212> TYPE: DNA
<213> ORGANISM: Artificial Sequence
<220> FEATURE:
<223> OTHER INFORMATION: VH1

<400> SEQUENCE: 65
gaggtgcagc tgttggagag cgggggaggc ttggtacagc ctgggggtc cctgcgcctc         60 tcctgtgcag ccagcggatt cacctttttct tacggttcta tgtactgggt ccgccaggct     120
```

-continued

```
ccagggaagg ggctggagtg ggtctcatct atttcttctg gttctggttc tacatactat      180
gcagactccg tgaagggccg gttcaccatc tcccgtgaca attccaagaa cacgctgtat      240
ctgcaaatga acagcctgcg tgccgaggac acggctgtat attattgtgc gcgctcttct      300
tactacggtt cttactactc tattgactat tggggccagg gaaccctggt caccgtctcc      360
tca                                                                    363

<210> SEQ ID NO 66
<211> LENGTH: 321
<212> TYPE: DNA
<213> ORGANISM: Artificial Sequence
<220> FEATURE:
<223> OTHER INFORMATION: VL1

<400> SEQUENCE: 66
gacatccaga tgacccagtc tccatcctcc ctgagcgcat ctgtaggaga ccgcgtcacc       60
atcacttgcc gggcaagtca gagcattagc agctatttaa attggtatca gcagaaacca      120
gggaaagccc ctaagctcct gatctatgct gcatccagtt tgcaaagtgg ggtcccatca      180
cgtttcagtg gcagtggaag cgggacagat ttcactctca ccatcagcag tctgcaacct      240
gaagattttg caacttatta ctgtcaacag tactacgaca acctgcccac ttttggccag      300
gggaccaagc tggagatcaa a                                                321

<210> SEQ ID NO 67
<211> LENGTH: 364
<212> TYPE: DNA
<213> ORGANISM: Artificial Sequence
<220> FEATURE:
<223> OTHER INFORMATION: VH

<400> SEQUENCE: 67
gaggtgcagc tgctcgagag cggggggaggc ttggtacagc ctggggggtc cctgcgcctc       60
tcctgtgcag ccagcggatt caccttttagc agctatgcca tgagctgggt ccgccaggct      120
ccagggaagg ggctggagtg ggtctcagct attagtggta gtggtggtag cacatactat      180
gcagactccg tgaagggccg gttcaccatc tcccgtgaca attccaagaa cacgctgtat      240
ctgcaaatga acagcctgcg tgccgaggac acggctgtat attattgtgc gcgctactac      300
ggtggttact actctgcttg gatggactat tggggccagg gaaccctggt caccgtctcc      360
tcag                                                                   364

<210> SEQ ID NO 68
<211> LENGTH: 321
<212> TYPE: DNA
<213> ORGANISM: Artificial Sequence
<220> FEATURE:
<223> OTHER INFORMATION: VL

<400> SEQUENCE: 68
gacatccaga tgacccagtc tccatcctcc ctgagcgcat ctgtaggaga ccgcgtcacc       60
atcacttgcc gggcaagtca gagcattagc agctatttaa attggtatca gcagaaacca      120
gggaaagccc ctaagctcct gatctatgct gcatccagtt tgcaaagtgg ggtcccatca      180
cgtttcagtg gcagtggaag cgggacagat ttcactctca ccatcagcag tctgcaacct      240
gaagattttg caacttatta ctgtcaacag acttacggtt acctgcacac ttttggccag      300
gggaccaagc tggagatcaa a                                                321
```

-continued

```
<210> SEQ ID NO 69
<211> LENGTH: 351
<212> TYPE: DNA
<213> ORGANISM: Artificial Sequence
<220> FEATURE:
<223> OTHER INFORMATION: VH

<400> SEQUENCE: 69
gaggtgcagc tgttggagag cggggggaggc ttggtacagc ctggggggtc cctgcgcctc      60
tcctgtgcag ccagcggatt caccttggt ggttactaca tgtcttgggt ccgccaggct      120
ccagggaagg ggctggagtg ggtctcatac attcctggtt ctggtggttc tacatactat      180
gcagactccg tgaagggccg gttcaccatc tcccgtgaca attccaagaa cacgctgtat      240
ctgcaaatga acagcctgcg tgccgaggac acggctgtat attattgtgc gcgctacgac      300
tactactgga tggactattg gggccaggga accctggtca ccgtctcctc a              351

<210> SEQ ID NO 70
<211> LENGTH: 324
<212> TYPE: DNA
<213> ORGANISM: Artificial Sequence
<220> FEATURE:
<223> OTHER INFORMATION: VL

<400> SEQUENCE: 70
gacatccaga tgacccagtc tccatcctcc ctgagcgcat ctgtaggaga ccgcgtcacc      60
atcacttgcc gggcaagtca gagcattagc agctatttaa attggtatca gcagaaacca      120
gggaaagccc ctaagctcct gatctatgct gcatccagtt tgcaaagtgg ggtcccatca      180
cgtttcagtg gcagtggaag cgggacagat ttcactctca ccatcagcag tctgcaacct      240
gaagattttg caacttatta ctgtcaacag ggtcatggtt cttacccgca cacttttggc      300 cagggggacca agctggagat caaa                                          324

<210> SEQ ID NO 71
<211> LENGTH: 369
<212> TYPE: DNA
<213> ORGANISM: Artificial Sequence
<220> FEATURE:
<223> OTHER INFORMATION: VH2

<400> SEQUENCE: 71
gaggtgcagc tgttggagag cggggggaggc ttggtacagc ctggggggtc cctgcgcctc      60
tcctgtgcag ccagcggatt cacctttct tcttactaca tgggttgggt ccgccaggct      120
ccagggaagg ggctggagtg ggtctcaggt attggttctt actacggtta cacaggttat      180
gcagactccg tgaagggccg gttcaccatc tcccgtgaca attccaagaa cacgctgtat      240
ctgcaaatga acagcctgcg tgccgaggac acggctgtat attattgtgc gcgcgcttac      300
tacgactaca actactacta cgcttacttt gactattggg gccagggaac cctggtcacc      360
gtctcctca                                                          369

<210> SEQ ID NO 72
<211> LENGTH: 324
<212> TYPE: DNA
<213> ORGANISM: Artificial Sequence
<220> FEATURE:
<223> OTHER INFORMATION: VL2

<400> SEQUENCE: 72
gacatccaga tgacccagtc tccatcctcc ctgagcgcat ctgtaggaga ccgcgtcacc      60
```

-continued

```
atcacttgcc gggcaagtca gagcattagc agctatttaa attggtatca gcagaaacca    120
gggaaagccc ctaagctcct gatctatgct gcatccagtt tgcaaagtgg ggtcccatca    180
cgtttcagtg gcagtggaag cgggacagat ttcactctca ccatcagcag tctgcaacct    240
gaagattttg caacttatta ctgtcaacag tctgttccgc actacccgtt cacttttggc    300
caggggacca agctggagat caaa                                          324
```